United States Patent
Davis

(10) Patent No.: US 9,140,764 B2
(45) Date of Patent: Sep. 22, 2015

(54) PORTABLE SELF POWERED LINE MOUNTED DEVICE AND METHOD FOR MEASURING THE VOLTAGE OF ELECTRIC POWER LINE CONDUCTORS

(71) Applicant: Murray W. Davis, Gross Pointe Woods, MI (US)

(72) Inventor: Murray W. Davis, Gross Pointe Woods, MI (US)

(*) Notice: Subject to any disclaimer, the term of this patent is extended or adjusted under 35 U.S.C. 154(b) by 132 days.

(21) Appl. No.: 14/084,978

(22) Filed: Nov. 20, 2013

(65) Prior Publication Data
US 2014/0176164 A1 Jun. 26, 2014

Related U.S. Application Data

(60) Provisional application No. 61/740,517, filed on Dec. 21, 2012.

(51) Int. Cl.
*G01R 19/00* (2006.01)
*G01R 31/40* (2014.01)
(Continued)

(52) U.S. Cl.
CPC ............ *G01R 31/40* (2013.01); *A46B 9/028* (2013.01); *G01B 11/0616* (2013.01);
(Continued)

(58) Field of Classification Search
CPC ........ G01R 27/02; G01R 27/28; G01R 31/08; G01R 31/40; G01R 19/0084; G01R 19/0092; G01R 1/20; G01R 1/22; A46B 9/028; A46B 2200/3073; G01W 1/14; G01N 27/223; H01F 38/30; H01F 27/02; H01F 27/22; G01D 11/30; H01R 4/28; G01B 11/0616; H04N 5/2252; G01K 13/00; H02G 1/02; Y10T 29/49117
USPC .................................. 324/709, 691, 649, 600
See application file for complete search history.

(56) References Cited

U.S. PATENT DOCUMENTS 2,303,824 A  12/1942  Comins
2,306,117 A  12/1942  Dunlap
(Continued)

FOREIGN PATENT DOCUMENTS

CN  202041573  11/2011
JP  2003-061752  9/2004

OTHER PUBLICATIONS

Pradhan, et al., Fault Direction Estimation in Radial Distribution System Using Phase Change in Sequence Current, IEEE Transactions on Power Delivery, vol. 22, No. 4, pp. 2065-2071, Oct. 2007.
(Continued)

*Primary Examiner* — Hoai-An D Nguyen
(74) *Attorney, Agent, or Firm* — Carlson, Gaskey & Olds, P.C.

(57) ABSTRACT

A device for measuring a voltage of an electric power line conductor of a power system according to an exemplary aspect of the present disclosure includes, among other things, a first electrically conductive housing configured to be installed on a first power line conductor and a first virtual grounding member configured to electrically ground a first housing to a first power line conductor voltage. A first measuring resistor is electrically connected between the first virtual grounding member and an electrically isolated lead wire, the electrically isolated lead wire is electrically connected to a first voltage dropping device, the first voltage dropping device is configured to be electrically connected to a second power line conductor. A sensor electronics module is configured to measure a voltage drop across the first measuring resistor, the voltage drop being directly proportional to the voltage between the first power line conductor and the second power line conductor.

39 Claims, 36 Drawing Sheets

(51) Int. Cl.

| | |
|---|---|
| *A46B 9/02* | (2006.01) |
| *H02G 1/02* | (2006.01) |
| *G01B 11/06* | (2006.01) |
| *G01W 1/14* | (2006.01) |
| *G01R 1/20* | (2006.01) |
| *G01R 31/08* | (2006.01) |
| *G01N 27/22* | (2006.01) |
| *H01F 38/30* | (2006.01) |
| *H04N 5/225* | (2006.01) |
| *G01D 11/30* | (2006.01) |
| *G01K 13/00* | (2006.01) |
| *H01F 27/02* | (2006.01) |
| *H01F 27/22* | (2006.01) |
| *H01R 4/28* | (2006.01) |
| *G01R 1/22* | (2006.01) |

(52) U.S. Cl.
CPC ............. *G01D 11/30* (2013.01); *G01K 13/00* (2013.01); *G01N 27/223* (2013.01); *G01R 1/20* (2013.01); *G01R 1/22* (2013.01); *G01R 19/0084* (2013.01); *G01R 19/0092* (2013.01); *G01R 31/08* (2013.01); *G01W 1/14* (2013.01); *H01F 27/02* (2013.01); *H01F 27/22* (2013.01); *H01F 38/30* (2013.01); *H01R 4/28* (2013.01); *H02G 1/02* (2013.01); *H04N 5/2252* (2013.01); *A46B 2200/3073* (2013.01); *Y10T 29/49117* (2015.01)

(56) References Cited

U.S. PATENT DOCUMENTS

| | | | |
|---|---|---|---|
| 3,267,507 A | 8/1966 | Cox | |
| 3,622,867 A | 11/1971 | Topper et al. | |
| 3,678,372 A | 7/1972 | Elder | |
| 3,820,106 A | 6/1974 | Yamashita et al. | |
| 3,861,197 A | 1/1975 | Adler | |
| 4,032,842 A | 6/1977 | Green et al. | |
| 4,052,000 A | 10/1977 | Honikman | |
| 4,053,830 A | 10/1977 | Porter | |
| 4,061,963 A | 12/1977 | Green | |
| 4,234,863 A | 11/1980 | Shumway et al. | |
| 4,242,930 A | 1/1981 | Myers et al. | |
| 4,268,818 A | 5/1981 | Davis et al. | |
| 4,326,316 A | 4/1982 | Dolenti | |
| 4,420,752 A | 12/1983 | Davis et al. | |
| 4,499,417 A | 2/1985 | Wright et al. | |
| 4,546,340 A | 10/1985 | Kuchuris | |
| 4,728,887 A | 3/1988 | Davis | |
| 4,746,241 A | 5/1988 | Burbank | |
| 4,801,937 A | 1/1989 | Fernandes | |
| 4,806,855 A | 2/1989 | Davis | |
| 4,827,272 A | 5/1989 | Davis | |
| 5,029,101 A | 7/1991 | Fernandes | |
| 5,140,257 A | 8/1992 | Davis | |
| 5,181,026 A * | 1/1993 | Granville | 340/870.28 |
| 5,232,518 A | 8/1993 | Nath et al. | |
| 5,341,088 A | 8/1994 | Davis | |
| 5,351,359 A | 10/1994 | Golden | |
| 5,426,360 A | 6/1995 | Maraio et al. | |
| 5,594,359 A * | 1/1997 | Hashimoto | 324/762.02 |
| 5,703,568 A | 12/1997 | Hegyi | |
| 5,796,259 A | 8/1998 | Dickmander | |
| 5,838,526 A * | 11/1998 | Ishikawa et al. | 361/118 |
| 5,883,511 A | 3/1999 | Foster | |
| 6,144,017 A | 11/2000 | Millett et al. | |
| 6,151,065 A | 11/2000 | Steed et al. | |
| 6,157,160 A | 12/2000 | Okawa et al. | |
| 6,299,824 B1 | 10/2001 | Mayr et al. | |
| 6,713,670 B2 | 3/2004 | Stern et al. | |
| 6,741,069 B1 | 5/2004 | Klemar et al. | |
| 6,924,732 B2 | 8/2005 | Yahoo | |
| 6,983,508 B2 | 1/2006 | Saurer | |
| 7,030,593 B2 | 4/2006 | Pinkerton et al. | |
| 7,127,972 B2 | 10/2006 | Klein et al. | |
| 7,310,109 B2 | 12/2007 | Dottling et al. | |
| 7,412,338 B2 | 8/2008 | Wynans et al. | |
| 7,432,787 B2 | 10/2008 | Muench et al. | |
| 7,545,140 B2 | 6/2009 | Humphreys et al. | |
| 7,557,563 B2 | 7/2009 | Gunn et al. | |
| 7,570,045 B2 | 8/2009 | Wolfe et al. | |
| 7,579,824 B2 | 8/2009 | Rea | |
| 7,706,596 B2 | 4/2010 | Garvey | |
| 8,022,291 B2 | 9/2011 | Thomsen et al. | |
| 8,144,445 B2 | 3/2012 | Caggiano et al. | |
| 8,184,015 B2 | 5/2012 | Lilien et al. | |
| 8,203,328 B2 | 6/2012 | Bose et al. | |
| 8,300,922 B1 | 10/2012 | Garvey, III | |
| 8,320,146 B2 | 11/2012 | Haines et al. | |
| 8,322,332 B2 | 12/2012 | Rogers | |
| 8,400,504 B2 | 3/2013 | Al-Duwaish et al. | |
| RE44,256 E | 6/2013 | Bright et al. | |
| 8,536,857 B2 | 9/2013 | Nero, Jr. | |
| 8,628,211 B2 | 1/2014 | Jensen et al. | |
| 8,686,302 B2 | 4/2014 | Brasher et al. | |
| 2003/0052687 A1 | 3/2003 | McQueeney et al. | |
| 2004/0012678 A1 | 1/2004 | Li | |
| 2006/0060007 A1 | 3/2006 | Mekhanoshin | |
| 2006/0125469 A1 | 6/2006 | Hansen | |
| 2008/0077336 A1 | 3/2008 | Fernandes | |
| 2008/0136403 A1 | 6/2008 | Deck | |
| 2008/0297162 A1 | 12/2008 | Bright | |
| 2009/0009180 A1 | 1/2009 | Varghai et al. | |
| 2009/0207421 A1 | 8/2009 | Kelly et al. | |
| 2009/0212241 A1 | 8/2009 | McGeoch | |
| 2009/0243876 A1 | 10/2009 | Lilien et al. | |
| 2010/0039090 A1 | 2/2010 | Sykes | |
| 2010/0084920 A1 | 4/2010 | Banting et al. | |
| 2010/0085036 A1 | 4/2010 | Banting et al. | |
| 2010/0192975 A1 | 8/2010 | Schweikert | |
| 2011/0204879 A1 | 8/2011 | Peretto | |
| 2011/0267673 A1 | 11/2011 | Agrawal et al. | |
| 2011/0308566 A1 | 12/2011 | Johnson | |
| 2012/0086804 A1 | 4/2012 | Ishibashi et al. | |
| 2012/0152346 A1 | 6/2012 | Yang et al. | |
| 2013/0022078 A1 | 1/2013 | Phillips et al. | |
| 2013/0179079 A1 | 7/2013 | Lancaster | |
| 2013/0205900 A1 | 8/2013 | Nulty | |
| 2013/0221977 A1 | 8/2013 | Ukil et al. | |
| 2014/0110376 A1 | 4/2014 | Zahlmann et al. | |
| 2014/0123750 A1 | 5/2014 | Liu et al. | |
| 2014/0145858 A1 | 5/2014 | Miller et al. | |

OTHER PUBLICATIONS

Eissa, Evaluation of a New Current Directional Protection Technique Using Field Data, IEEE Transactions on Power Delivery, vol. 20, No. 2, pp. 566-572, Apr. 2005.
Ukil, et al., Smart Distribution Protection Using Current-Only Directional Overcurrent Relay, Innovative Smart Grid Technologies Conference Europe, 2010 IEEE PES, pp. 1-7, 2010.
Recloser, available at http://en.wikipedia.org/wiki/Recloser on Feb. 2, 2012.
Digital protective relay, available at http://en.wikipedia.org/wiki/Digital_protective_relay on Jun. 18, 2012.

* cited by examiner

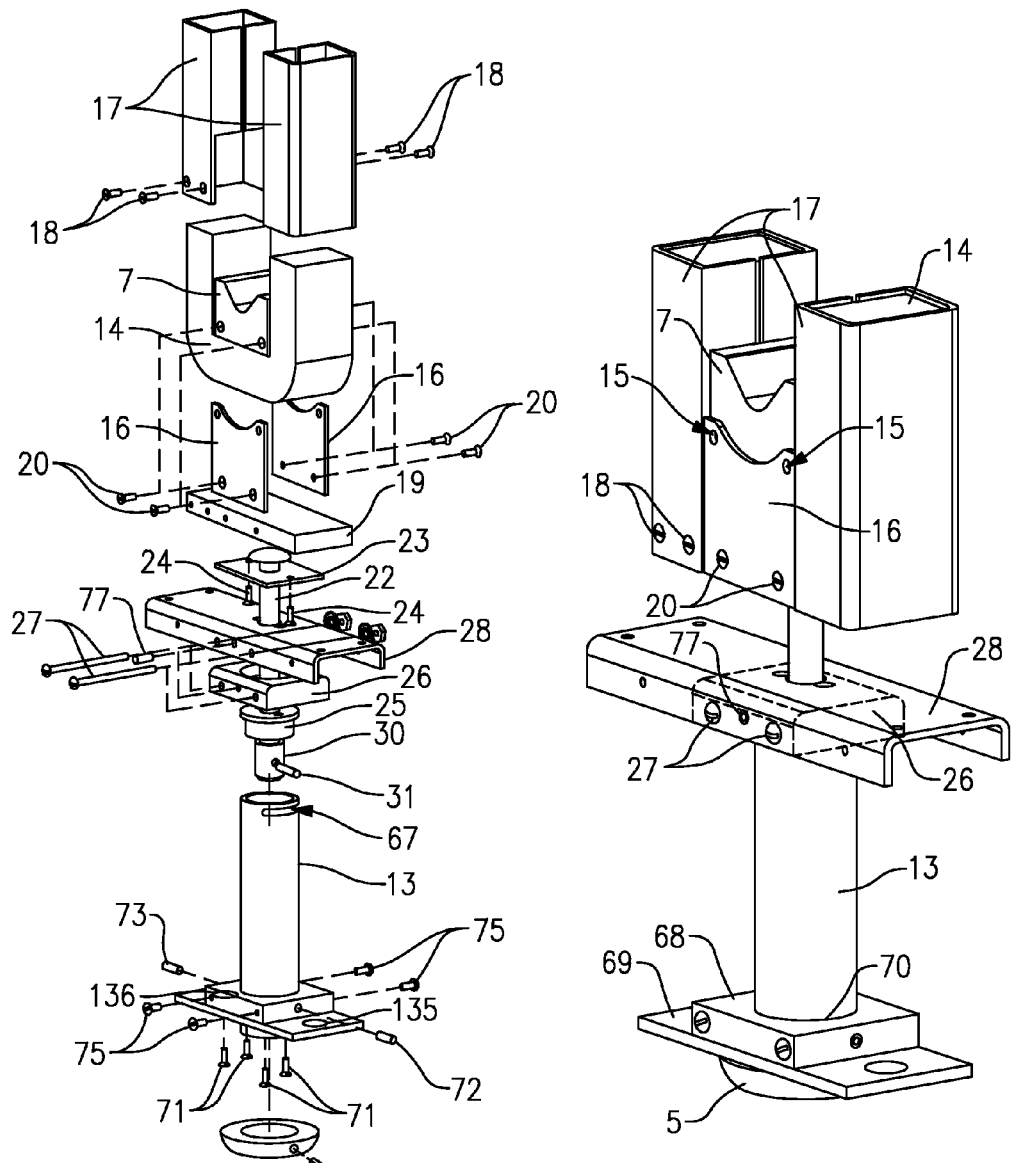

PORTABLE SELF POWERED LINE MOUNTED DEVICE AND METHOD FOR MEASURING THE VOLTAGE OF ELECTRIC POWER LINE CONDUCTORS

CROSS-REFERENCE TO RELATED APPLICATIONS

The application claims priority to U.S. Provisional Application No. 61/740,517 which was filed on Dec. 21, 2012.

BACKGROUND

The present disclosure relates to a multiple parameter sensor-transmitter/receiver unit which may be installed on or removed from an energized electric power line, such as an overhead power line. With the advent of Smart-Grid applications for electric power systems, there is an ever increasing need for a device that measures electric, mechanical, and environmental parameters of the power line.

In order to address the increasing need for monitoring power lines, devices have been developed that attach directly to the power line. These devices generally require a power source, such as batteries or solar panels. When utilizing batteries, regular maintenance must be performed to replace the batteries, which can become costly. When solar panels are used, the device may only be power during sunny weather conditions and during daylight hours. Therefore, there is a need for a device which is low maintenance and can be constantly powered independent of weather conditions.

The function of a voltage transformer is to produce a low secondary voltage output, typically 120 volts, which is representative of the high primary voltage of the electric power distribution line or transmission line. The low secondary voltage output is proportional to the turns ratio of the transformer and would be in phase with or in phase opposition to the primary voltage depending upon its connection to the primary phase wires. However, the secondary voltage could only be in phase with the primary voltage for an ideal transformer which has no leakage impedance, no excitation current, and no losses. But, actual voltage transformers require excitation current to magnetize the iron core which is supplied by the primary lines through the leakage impedance of the primary. Also, the load current in the transformer windings causes a voltage drop in the leakage impedance of the primary and secondary windings. The load current and excitation current cause a voltage drop which results in a turns ratio error and a phase angle shift other than a 180 degree phase shift between the primary voltage and the secondary voltage output. Therefore, a turns ratio correction factor and a phase angle correction factor must be applied to obtain the true ratio and the true phase angle between the measured voltage and the measured current on the primary, or the power factor.

Other methods of measuring the voltage have included (1) high voltage divider circuits, (2) voltage based on measurement of the electric field outside the conductor at some point, and (3) voltage based on measurement of the electric field using optics. The high voltage divider method normally involves a high value resistor or resistors being attached to one line or phase conductor at one end and the other end of this high value resistor or resistors being connected in series with a low value measuring resistor with its other end being attached to earth ground at zero voltage. The voltage measurement is then a measurement of the low value current flow from the high voltage line conductor to ground through these series connected resistors and the resultant voltage drop across the measurement resistor. This voltage drop can easily be measured with instruments at ground potential. The problems with this method are the resistors are dissipative and can result in overheating and it cannot be used to measure phase to phase voltages because of the high voltage that appears on the measurement resistor prevents the use of measuring instruments normally located at ground potential. The series connected resistors can be replaced with series connected capacitors which are non-dissipative, but then a phase shift occurs in the measured voltage.

Voltage is defined as the integral of the electric field between two points, the one point being the line or phase conductor itself and the other point being in space around this conductor. The problem with this method is the electric field in space around one phase conductor can be significantly affected by the presence of the other phase conductors of a three phase system and various structures which support these phase conductors may be steel towers or poles which are grounded, or wood poles which have ground leads connected to lightning arresters or other equipment grounds. Therefore, the measurements of the electric field and thus the voltages are very inaccurate. The use of optics has been employed, but their use thus far has resulted in flashovers across the fiber optic lead wires in high voltage transmission lines applications and the cost of such devices have been excessive, especially in high voltage measurement applications.

SUMMARY

A device for measuring a voltage of an electric power line conductor of a power system according to an exemplary aspect of the present disclosure includes, among other things, a first electrically conductive housing configured to be installed on a first power line conductor and a first virtual grounding member configured to electrically ground a first housing to a first power line conductor voltage. A first measuring resistor is electrically connected between the first virtual grounding member and an electrically isolated lead wire, the electrically isolated lead wire is electrically connected to a first voltage dropping device, the first voltage dropping device is configured to be electrically connected to a second power line conductor. A sensor electronics module is configured to measure a voltage drop across the first measuring resistor, the voltage drop being directly proportional to the voltage between the first power line conductor and the second power line conductor.

A device for measuring the voltage of an electric power line conductor for a power system according to another exemplary aspect of the present disclosure includes, among other things, a first electrically conductive housing configured to be installed on a first power line conductor and a first virtual grounding member configured to electrically ground the first housing to a first power line conductor voltage. A first measuring resistor is electrically connected between the first virtual ground member and an electrically isolated lead wire, the electrically isolated lead wire electrically connected to a first voltage dropping device, the first voltage dropping device configured to be electrically connected to an earth grounded neutral conductor. A sensor electronics module is configured to measure a voltage drop across the first measuring resistor, the voltage drop being directly proportional to a voltage between the first power line conductor and the earth grounded neutral conductor.

A device for measuring the voltage of an electric power line conductor for a power system according to another exemplary aspect of the present disclosure includes, among other things, a first electrically conductive housing configured to be installed on a first power line conductor and a first virtual grounding member configured to electrically ground the first housing to a first power line conductor voltage. A first measuring resistor is electrically connected between the first virtual ground member and an electrically isolated lead wire, the electrically isolated lead wire electrically connected to a first voltage dropping device, the first voltage dropping device configured to be electrically connected to an ungrounded neutral conductor. A sensor electronics module is configured to measure a voltage drop across the first measuring resistor, the voltage drop being directly proportional to a voltage between the first power line conductor and the ungrounded neutral conductor.

These and other features of the disclosed examples can be understood from the following description and the accompanying drawings, which can be briefly described as follows.

BRIEF DESCRIPTION OF THE DRAWINGS

FIG. 10 illustrates an expanded view of the lower magnetic core, example lead screw assembly, and an example hotstick guide tube.

FIG. 11 illustrates the collapsed view of the lower magnetic core, the lead screw assembly, and the hotstick guide tube.

DETAILED DESCRIPTION

Figure 1:
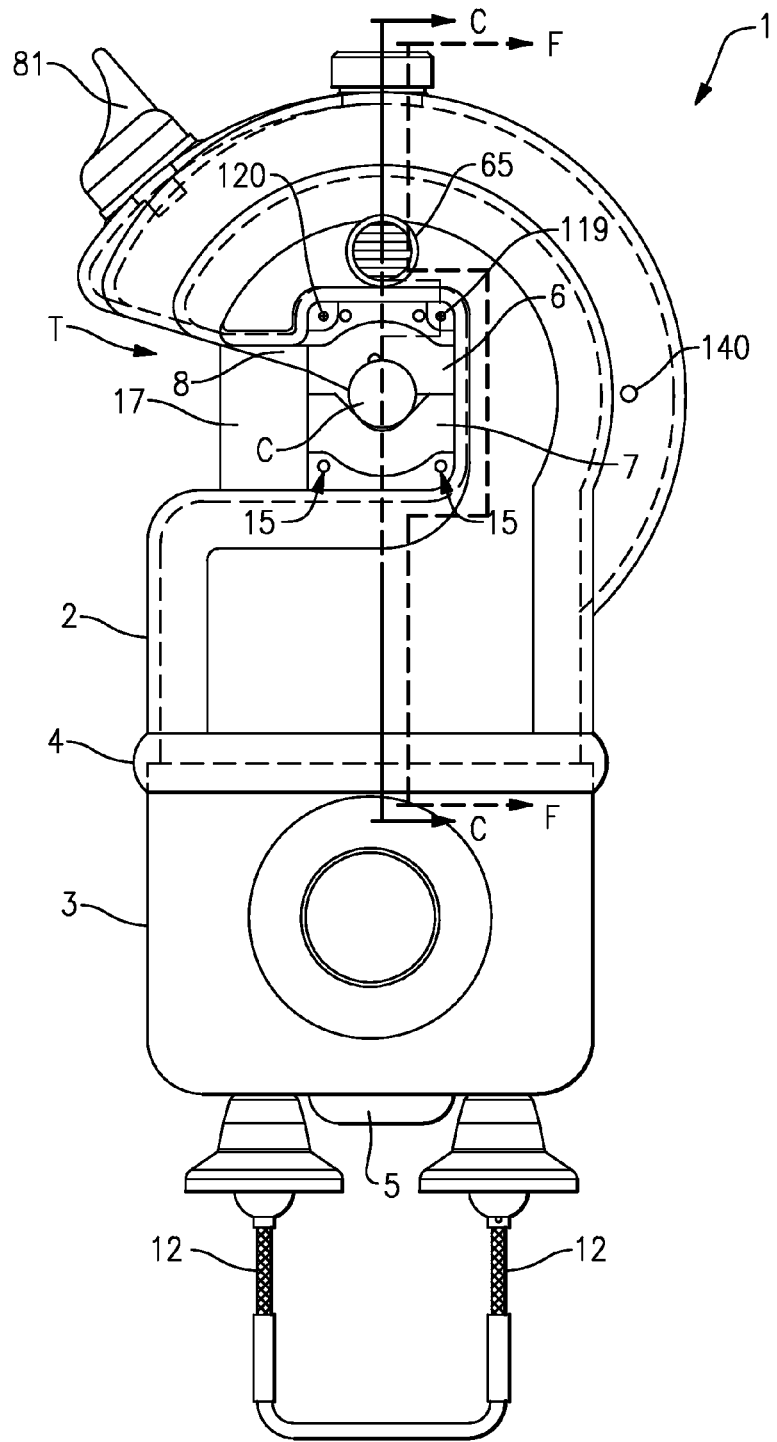
FIG. 1 illustrates a right side view of an example sensor transmitter receiver unit ("STR unit").
Figure 2:
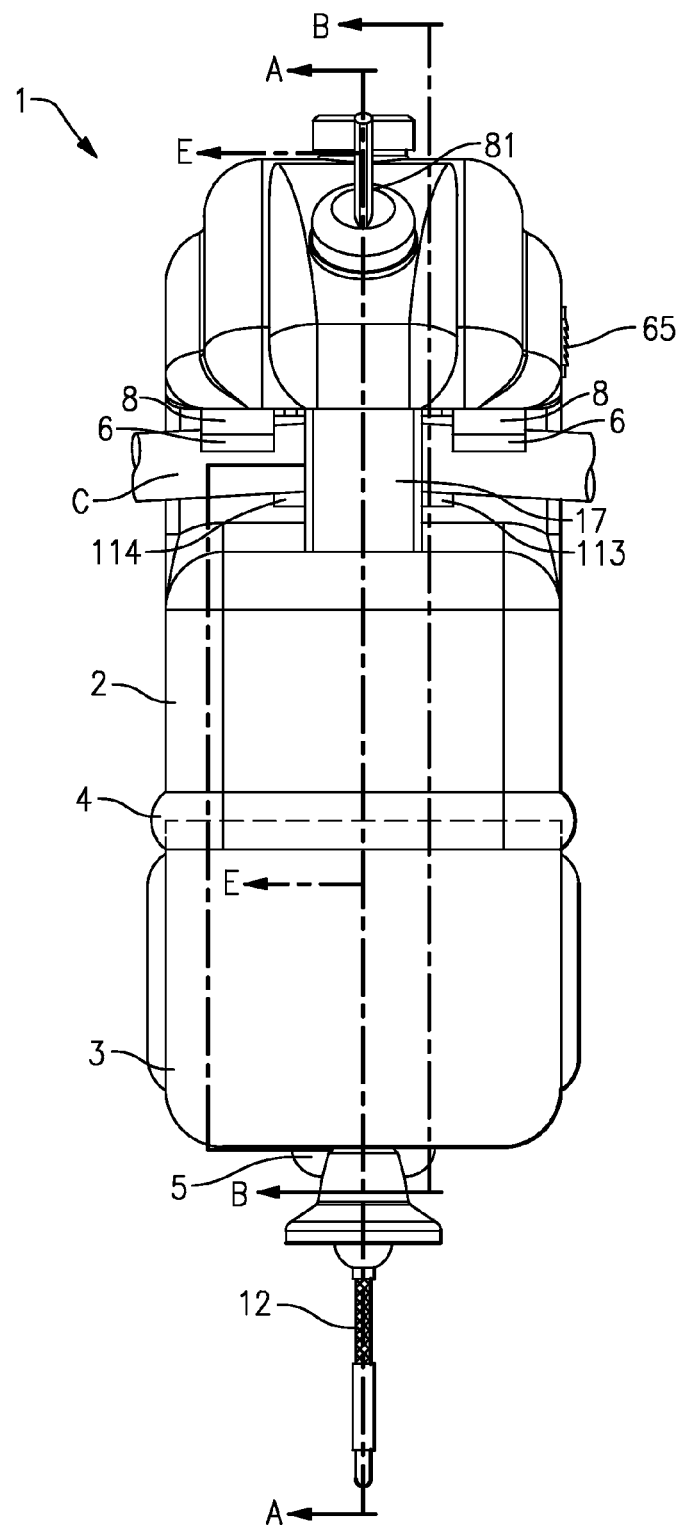
FIG. 2 illustrates a front view of the STR unit of FIG. 1.

FIGS. 1 and 2 illustrate an example sensor transmitter receiver unit ("STR unit") 1 installed on a power line conductor C for measuring and monitoring various parameters of the power line conductor C and its environment. The STR unit 1 is formed from a one piece upper housing 2 and a one piece lower housing 3. The lower housing 3 is accepted into a bead 4 formed on a distal end of the upper housing 2. In this example, the bead 4 which is an integral part of the upper housing 2 is formed by machining a portion of the upper housing 2 to form a groove on the inside of the bead 4. The lower housing 3 is secured to the bead 4 and the upper housing 2 by a collar 5. The collar 5 attaches to a hotstick guide tube 13 (FIG. 3) that is secured to the upper housing 2 and extends through the lower housing 3.

In one example, the upper housing 2 and the lower housing 3 are made of aluminum or other suitable electrically conductive material. The material chosen should accommodate subassembly installation without the use of external surface fasteners which could generate corona discharges due to high voltage being applied to the upper housing 2 and the lower housing 3. The upper housing 2 has the advantage of reducing the number of mating surfaces and eliminating mismatches between multiple cast parts which can generate corona discharges and audible noise due to slightly offset sharp edges of the mating surfaces of the adjacent castings.

Figure 3:
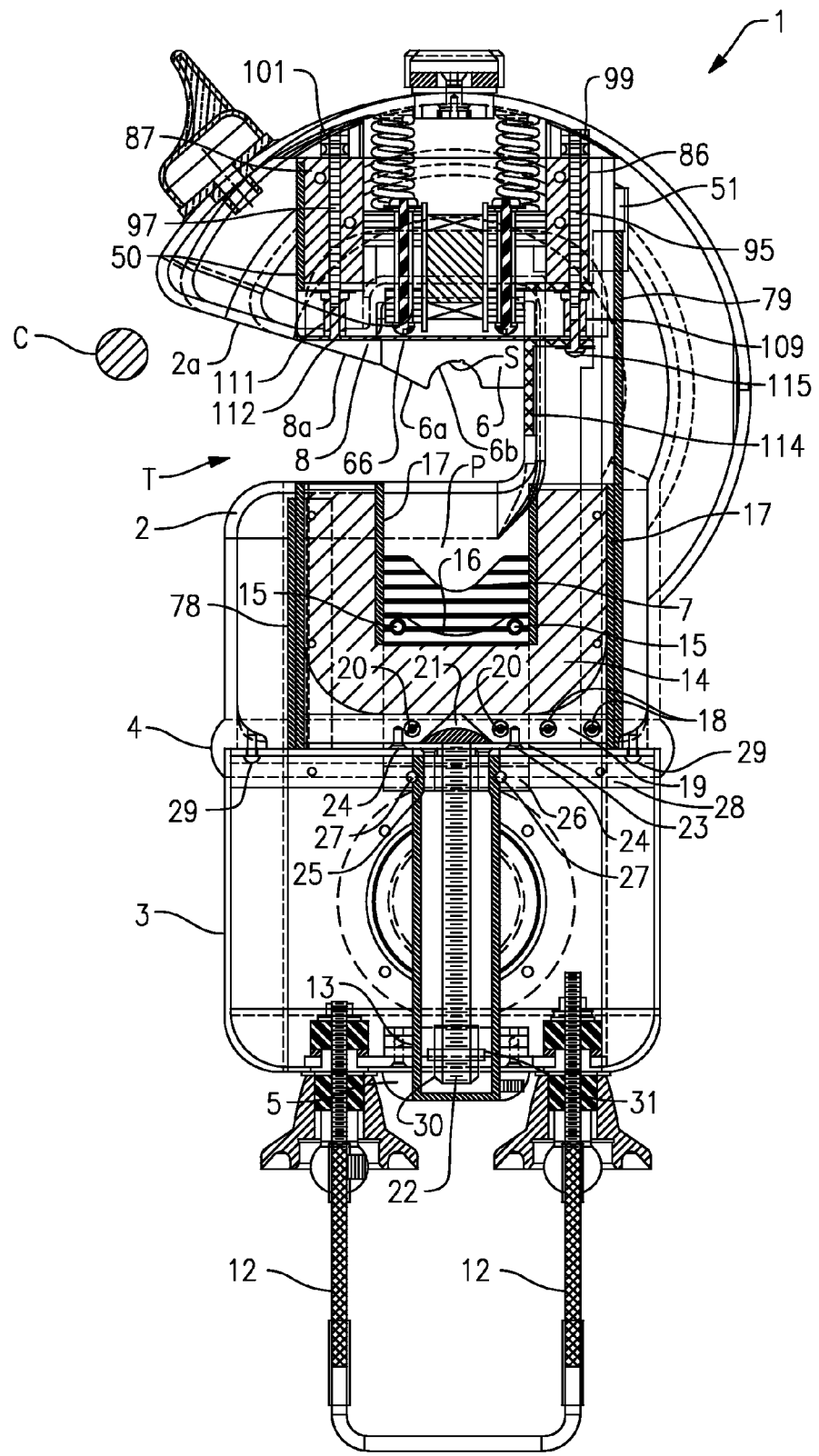
FIG. 3 illustrates a cross-sectional view taken along line A-A of FIG. 2.
Figure 4:
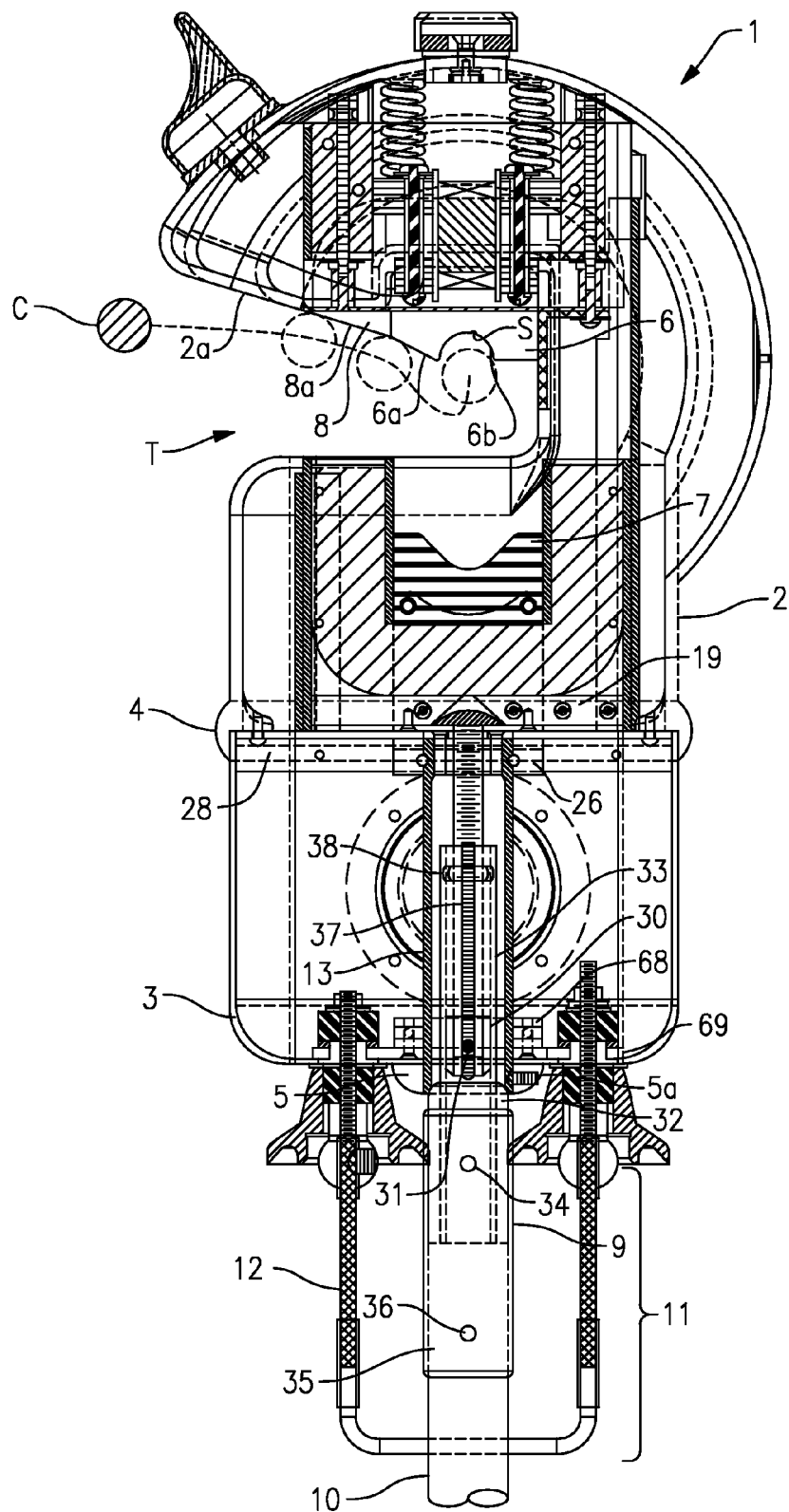
FIG. 4 illustrates a cross-sectional view taken along line A-A of FIG. 2 with an example hotstick.

Referring to FIGS. 3 and 4, before the STR unit 1 is clamped onto the conductor C, a lower jaw 7 is moved to its fully lowered position spaced from upper jaws 6. This allows the conductor C to pass from position "A" of FIG. 3 through a throat T on the left side of the upper housing 2 and onto the upper jaws 6 in position "B" as shown in FIG. 5.

With the lower jaw 7 of the STR unit 1 in its fully lowered position, a specially designed hotstick 10 is inserted into the bottom of the STR unit 1 and inside the hotstick guide tube 13. In this example, the hotstick 10 is made of an electrically insulated material such as fiberglass. The hotstick 10 includes a hotstick driver assembly 9 (FIG. 4) attached to the hotstick 10 with a pin 36. The hotstick 10 provides the required electrical insulation between the hands of the linemen and the energized conductor C. A flexible stirrup assembly 11 (FIG. 4) contains a flexible braided conductor 12 which bends out of the way to allow the hotstick driver assembly 9 to enter a hole in the collar 5. As mentioned earlier, the collar 5 secures the lower housing 3 to the bead 4 on the upper housing 2. The collar 5 is fastened to the hotstick guide tube 13 using the set screw 5a which is screwed into the collar 5 and into a hole in the hotstick guide tube 13.

With the hotstick 10 and the hotstick driver assembly 9 fully engaged inside the hotstick guide tube 13, the STR unit 1 can be lifted by the lineman with the hotstick 10 onto the conductor C while maintaining the STR unit 1 securely attached to the hotstick 10.

Figures 5, 5A:
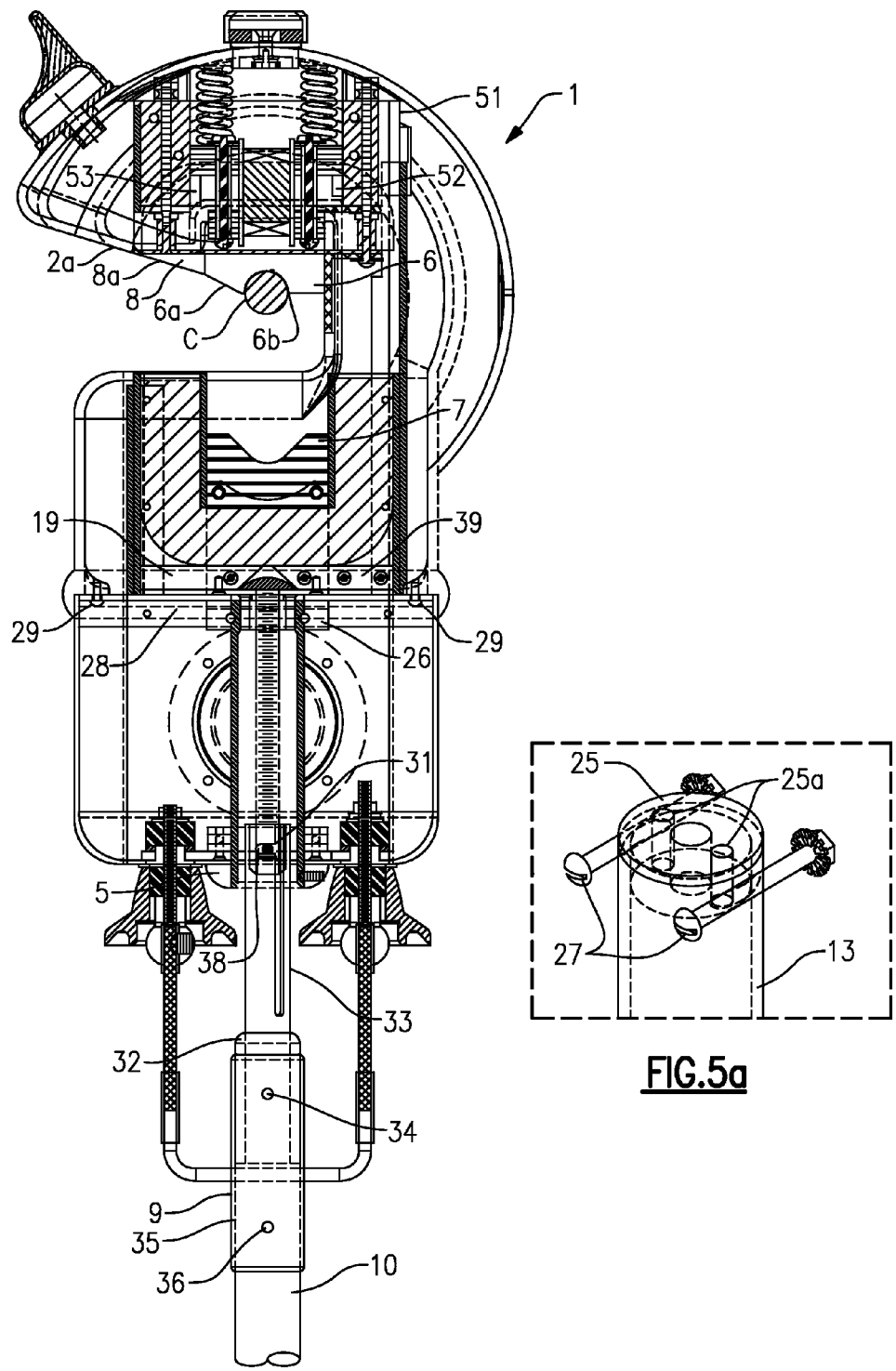
FIG. 5 illustrates another cross-sectional view taken along line A-A of FIG. 2 with the example hotstick.
FIG. 5a illustrates an enlarged view of a keyhole slot.
Figure 14:
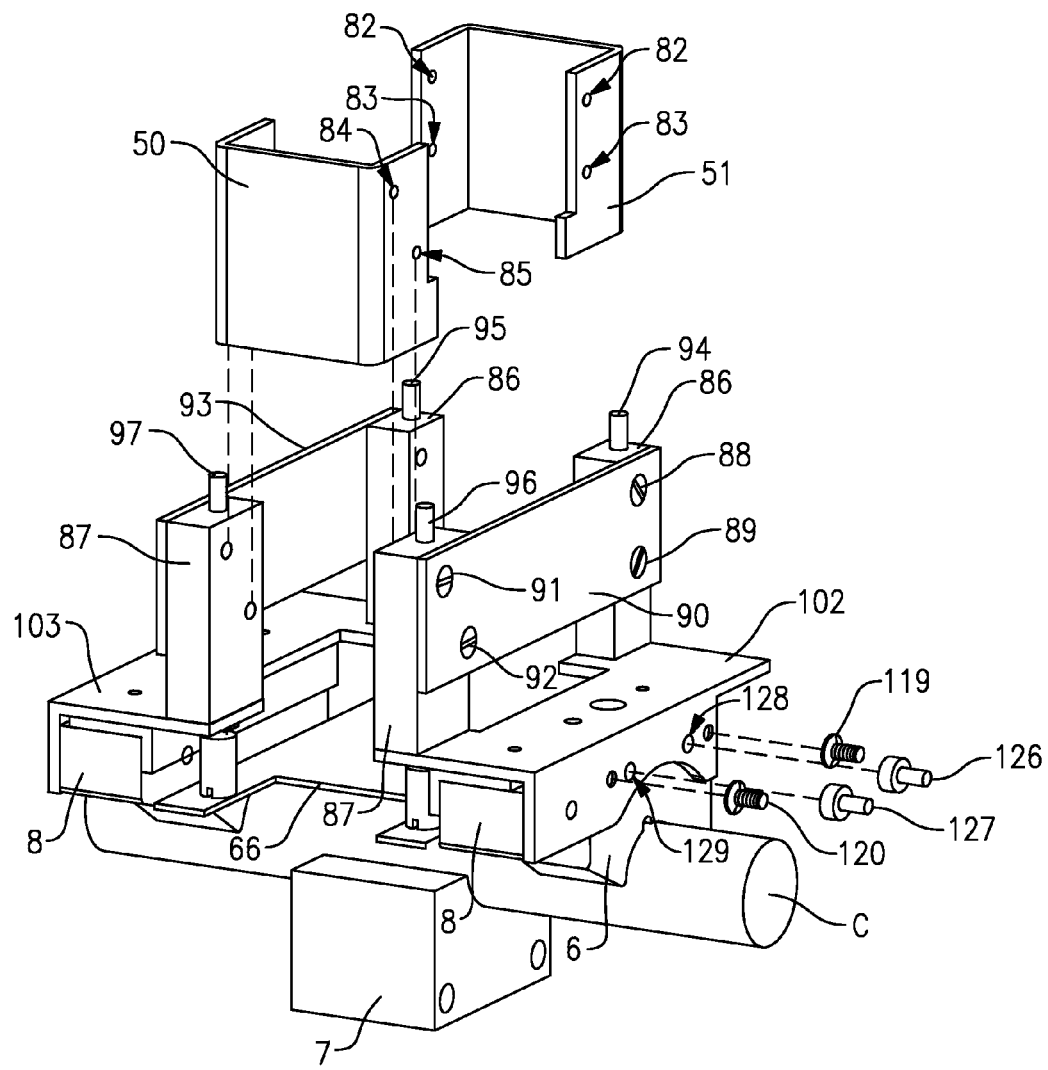
FIG. 14 illustrates an exploded view of example support blocks mounting the upper magnetic core subassembly and example upper and lower jaws.

The upper housing 2 includes two jaw inserts 8, shown in FIGS. 5 and 14, located adjacent the throat T and the upper jaws 6. The two jaw inserts 8 include inclined surfaces 8a and the upper jaws 6 include inclined surfaces 6a. The angle of incline of the inclined surfaces 8a matches the angle of the incline of an inclined surface 2a on the upper housing 2.

The angle of the inclined surfaces 6a is steeper than the angle of the inclined surfaces 8a and the inclined surface 2a to aid in installing the STR Unit 1 on the conductor C. As the conductor C slides across the inclined surfaces 2a and 8a and reaches the steeper incline of the inclined surface 6a, the STR unit 1 will bounce slightly upward and land in a circular notch 6b of the upper jaws 6 (See FIG. 4). This allows a conductor temperature sensor to be mounted vertically and in the middle inside the upper jaws 6 and initially extends slightly below the circular notch 6b for the upper portion of the conductor C. The two different inclined surfaces 6a and 8a of the jaw inserts 8 and upper jaws 6 prevent the conductor temperature sensor S, shown in FIGS. 3 and 4, from becoming damaged since the conductor C firmly lands vertically in the circular notch 6b of the upper jaws 6 and pushes the conductor temperature sensor S up to the inside surface of the circular notch 6b.

In FIG. 3, the lower jaw 7 is located in a pocket P between two legs of a lower magnetic core 14. The lower jaw 7 is held in place with two spring pins 132 and 133 (FIG. 15) located in the lower jaw 7 that snap into two holes 15 in a lower jaw holder 16 (FIGS. 10 and 11) which is attached to a bottom block 19 using two screws 20 (FIG. 3). The bottom block 19 is located adjacent the base of the upper housing 2.

Two identical electrically conductive lower core covers 17 partially surround the two legs of the lower magnetic core 14. The lower core covers 17 are attached to the bottom block 19 on each side of the lower jaw holder 16 using screws 18 of FIG. 3 on the front right side and one set of the screws 18 on the back left side (not shown). The front and back lower jaw holders 16 are both held in place by the four screws 20, two in the front and two in the back. The two legs of the lower magnetic core 14 are totally encased by the two lower core covers 17 and the front and back lower jaw holders 16. Therefore, the lower magnetic core 14 is not exposed to any moisture, such as from rain, snow, and ice that could enter through the throat T of the upper housing 2 (FIG. 3).

The bottom block 19 contains a conical hole 21 in the center which provides a very low friction bearing surface for the semi-circular top of a lead screw 22 (FIG. 3). The lead screw 22 is held in the conical hole 21 with a retainer plate 23 which has a hole in the middle the size of the lead screw 22 diameter and is fastened to the bottom block 19. The lead screw 22 is threaded into the center of a threaded bushing 25. The threaded bushing 25 has a reduced diameter cylindrical lower portion which fits inside the hotstick guide tube 13 and a larger diameter cylindrical top portion of the threaded bushing 25 is supported on the upper end of the hotstick guide tube 13. Both the threaded bushing 25 and the hotstick guide tube 13 are attached to a hotstick guide support 26 using two large through bolts 27 and nuts which are placed through the holes in a bottom support 28.

Referring to FIG. 2, the upper jaws 6 include two spaced apart jaws and the lower jaw 7 includes a single jaw aligned between the two spaced apart upper jaws 6. When lower jaw 7 is clamped onto the conductor C, the conductor C is bent slightly upward as the lower jaw 7 extends upward between the upper jaws 6 creating a bending moment in the conductor C. The bending moment in the conductor C prevents the STR unit 1 from sliding down the conductor C, especially when the STR unit 1 is mounted at the point of attachment adjacent a utility pole or tower where the slope of the conductor C is at its maximum value. Preventing the upper jaws 6 and the lower jaw 7 from sliding down the conductor C at the point of attachment is necessary when the STR unit is being used to measure sag of the power line conductor.

Referring to FIGS. 5 and 5a, the bottom support 28 includes an upside down "U" shaped cross member and is fastened at each end to the upper housing with two large threaded screws 29 on each side. The threaded bushing 25 has two small vertical holes 25a drilled through the threaded bushing 25 on each side of the threaded hole in the middle for the lead screw 22. The vertical holes 25a are countersunk on the top and provide drainage paths for fluid, such as rain water, that can accumulate underneath the bottom block 19 and on top of the bottom support 28 (FIG. 5a). The water then drains through the two vertical holes 25a in the threaded bushing 25 and drops on the inside of the hotstick guide tube 13 and out the bottom of the STR unit 1. Therefore, water will not leak into the lower housing 3.

Figure 6:
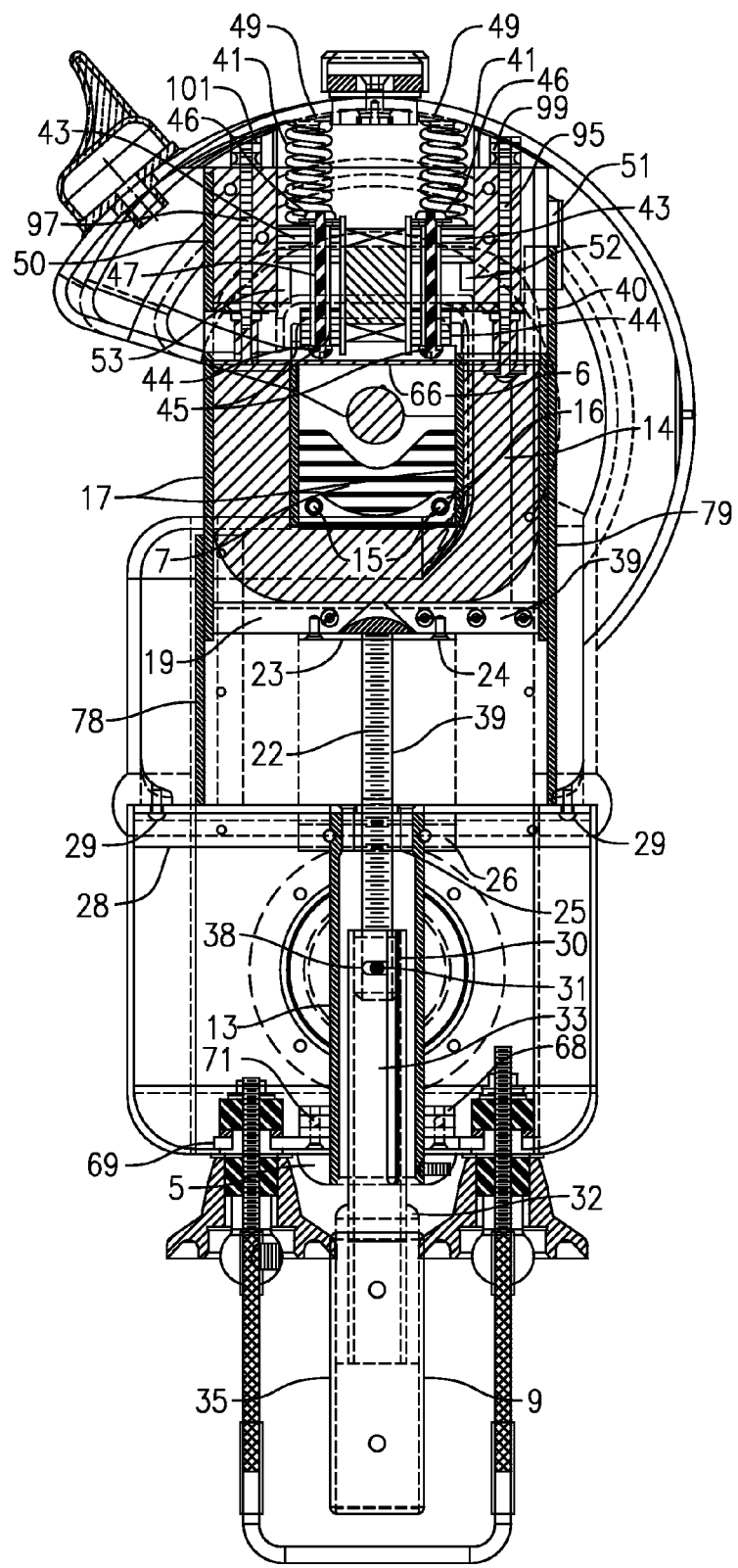
FIG. 6 illustrates another cross-sectional view taken along line A-A of FIG. 2 engaging a conductor.

Referring to FIG. 6, the lead screw 22 has a small diameter hotstick guide 30 which is threaded on the inside and is screwed on the bottom of the lead screw 22. A pin 31 keeps the hotstick guide 30 from turning on the lead screw 22. The hotstick guide 30 prevents the inside of a hotstick lead screw driver 33 from coming into contact with the threads on the lead screw 22 and damaging the internal bore of the lead screw driver 33. It also guides the lead screw driver 33 onto the lead screw 22. When the pin 31 engages the lead screw driver 33 the STR unit 1 is ready for installation on the conductor C.

The hotstick driver assembly 9 includes the lead screw driver 33, a hotstick driver coupling 32, a rivet 34, a hotstick sleeve 35, the pin 36, and the hotstick 10. The hotstick 10 of FIG. 4 rests on the rounded portion of the hotstick driver coupling 32 and the rounded inside bottom of the hotstick guide tube 13. This prevents the lead screw driver 33 from applying pressure to the threaded bushing 25 upon installation of the STR unit 1 on the conductor C. The lead screw driver 33 and the hotstick driver coupling 32 are each fastened to the hotstick sleeve 35 by the rivet 34 and the hotstick sleeve 35 is attached to the hotstick 10 with the pin 36. A long narrow vertical slot in the lead screw driver 33 allows the pin 31 of the lead screw 22 to be engaged with the lead screw driver 33 and is free to slide up or down in the vertical slot 37 as the lead screw is turned to tighten the lower jaw 7 on the conductor C or to loosen the lower jaw 7 from the conductor C to remove the STR unit 1.

When the hotstick driver assembly 9 is engaged with the lead screw 22 as shown in in FIG. 4, the STR unit 1 is raised to position "A" relative to the height of the conductor C. The STR unit 1 is then moved toward the conductor C so that the conductor C passes through the throat T of the upper housing 2 and into position "B" as shown in FIG. 5. Once the STR unit 1 is fully supported by the conductor C in position "B", the hotstick driver assembly 9 is turned clockwise by the installer with the hotstick 10 and allowed to drop down from its position in FIG. 4 to a lower position as in FIG. 5. A horizontal keyhole slot 38 of the lead screw driver 33 is now engaged with the pin 31 of the lead screw 22. With the pin 31 in the horizontal keyhole slot 38, the hotstick driver assembly 9 and the hotstick 10 are secured to the STR unit 1.

In this example, an opening and closing mechanism 39 of FIG. 6 extends the lower jaw 7 upward to secure the STR unit 1 on the conductor C. Additionally, the opening and closing mechanism 39 can also retract the lower jaw 7 to remove the STR unit 1 from the conductor C. The opening and closing mechanism 39 includes the lower magnetic core 14, the lower core covers 17, the lower jaw holders 16, the lower jaw 7, spring pins 132 and 133, the bottom block 19, the retainer plate 23, two fasteners 24, the lead screw 22, the hotstick guide 30, and the pin 31.

FIG. 6 illustrates the keyhole slot 38 on the lead screw driver 33 engaged with the pin 31 on the lead screw 22. As the lead screw 22 is turned clockwise, the opening and closing mechanism 39 moves the lower magnetic core 14 toward an upper magnetic core 40. The upper magnetic core 40 has two large compression springs 41 to bias the upper magnetic core 40 downward. The compression springs 44 provide pressure to hold both the upper magnetic core 40 and the lower magnetic core 14 together to reduce the magnetic reluctance caused by air gaps 54 (FIG. 8) between the upper magnetic core 40 and the lower magnetic core 14.

The hotstick driver assembly 9 can continue to be turned clockwise even after the lower magnetic core 14 begins to mate with the upper magnetic core 40 because the compression springs 41 compress at the top of the upper magnetic core 40. The clockwise motion of the hotstick driver assembly 9 can be achieved either manually or with a battery powered drill or another rotating device, until the lower jaw 7 is tightened onto the conductor C. After the STR unit 1 is mounted on the conductor C, the hotstick 10 is turned slightly to the left, or counterclockwise, and the pin 31 will become disengaged from the horizontal portion of the keyhole slot 38. The hotstick 10 is then free to be removed when the pin 31 aligns with the vertical slot 37.

Figure 7:
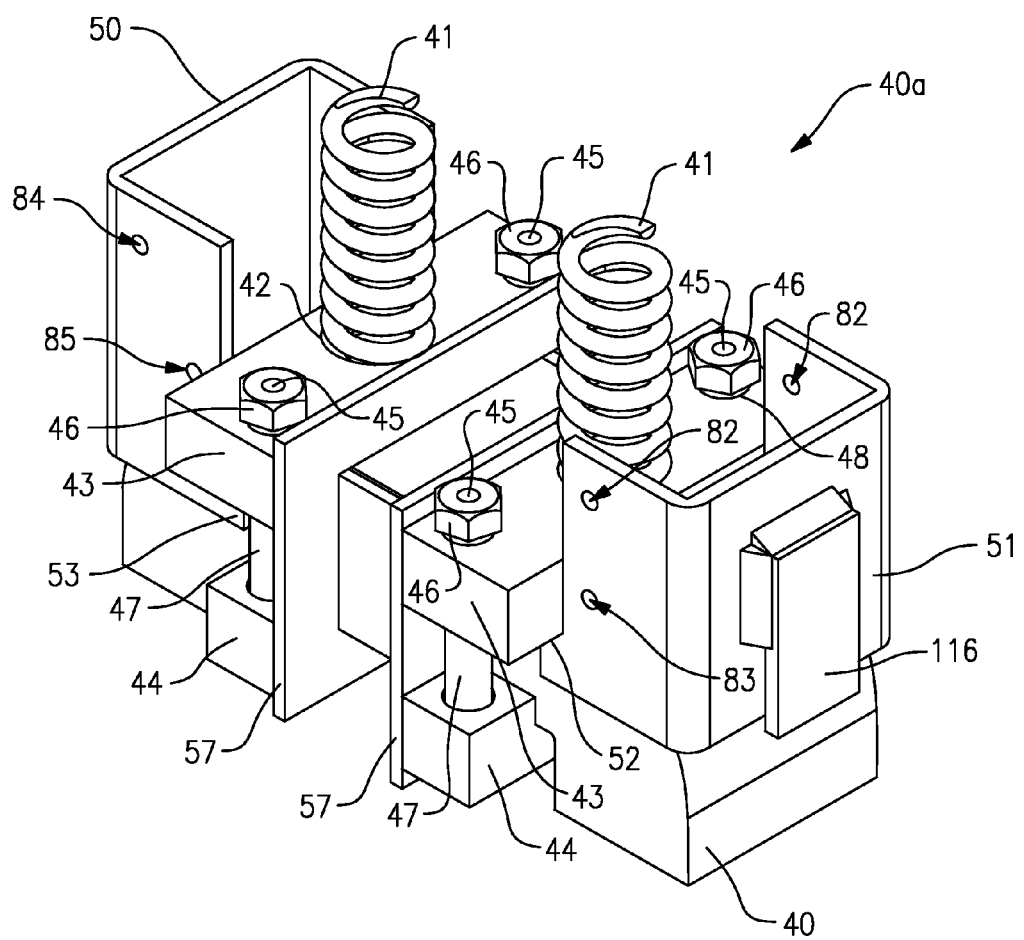
FIG. 7 illustrates an example upper magnetic core subassembly.
Figure 8:
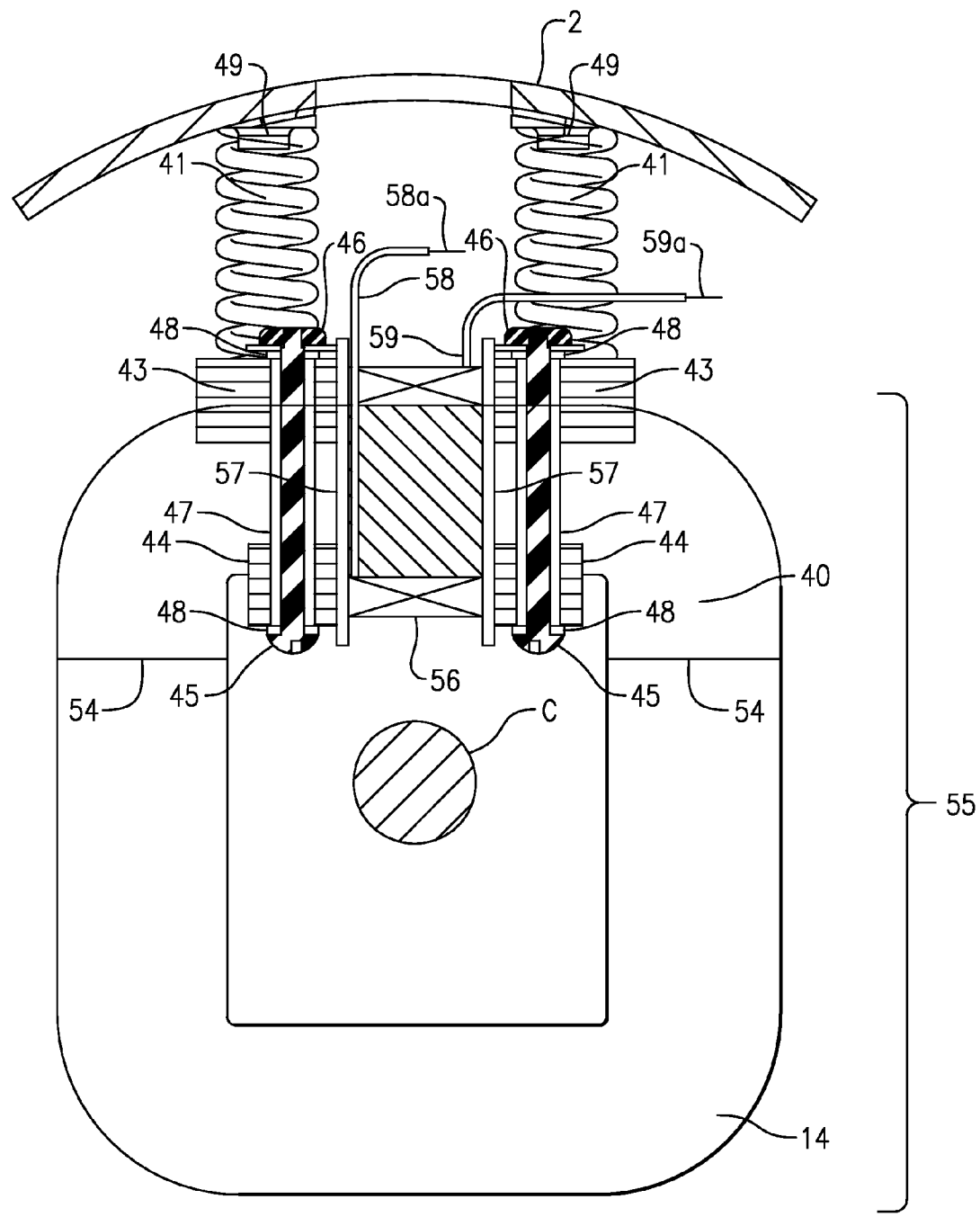
FIG. 8 illustrates an expanded view of an example upper magnetic core and an example lower magnetic core surrounding the conductor and an example power supply transformer.

FIGS. 7 and 8 illustrate the bottom of the compression springs 41 are held in alignment in two cylindrical pockets 42 of two identical horizontal upper core blocks 43 which are each used to clamp the upper magnetic core 40 to two identical magnetic horizontal lower core blocks 44. The top of the compression springs 41 are held in place with two projections 49 extending downward on the inside of the upper housing 2. The compression springs 41 are totally enclosed by the upper housing 2 and are protected from the adverse weather which can cause corrosion. The air gaps 54 between the upper and lower magnetic cores 40 and 14 are totally enclosed by the upper housing 2 which prevents the air gaps 54 from becoming corroded due to moisture from the environment. The horizontal upper core blocks 43 and the horizontal lower core blocks 44 are clamped around the upper magnetic core 40 on each side using two through bolts 45 and two nuts 46 in the front and two through bolts 45 and two nuts 46 located in the back of the upper horizontal core blocks 43 and horizontal lower core blocks 44.

When the two large compression springs 41 push the upper core blocks 43 down, the upper magnetic core 40 is prevented from falling out of a left core shoe 50 and a right core shoe 51, by a step 52 located at the bottom of the right core shoe 51 and a step 53 located at the bottom of the left core shoe 50.

When the lower magnetic core 14 mates with the upper magnetic core 40, the lead screw 22 can be turned further clockwise to move the two upper core blocks 43 away from the steps 52 and 53 and further compress the compression springs 41. The lead screw 22 can continue to be turned clockwise and compress the compression springs 41 until the lower jaw 7 and the upper jaws 6 are tight on the conductor C.

Electrical insulating spools 47 are inserted over each of the through bolts 45 and electrical insulating washers 48 are inserted under the head of each through bolt 45 and under each nut 46. The insulating spools 47 and the insulating washers 48 on each of the through bolts 45 prevent shorted electrically conductive paths around the upper magnetic core 40 which is comprised of the four through bolts 45, four nuts 46, the two electrically conductive upper core blocks 43 and the two lower core blocks 44.

When the upper jaws 6 and the lower jaw 7 are firmly tightened on the conductor C, the compression springs 41 are compressed to their maximum distance, and thus the maximum compressive force is also applied to the lower magnetic core 14 and the upper magnetic core 40. This decreases the size of the air gaps 54 between the lower magnetic core 14 and the upper magnetic core 40 and the magnetic reluctance between the lower magnetic core 14 and the upper magnetic core 40. Depending on the size of the conductor C, varying amounts torque can be applied to the hotstick driver assembly 9 to tighten the opening and closing mechanism 39 on the conductor C.

The physical size and shape of the upper jaws 6 and the lower jaw 7 are designed such that approximately the same compressive force is applied to the upper magnetic core 40 and the lower magnetic core 14. In one example, there are five different sets of upper and lower jaws 6 and 7 that can fit different conductor sizes and types ranging from 0.162 inches in diameter and up to 1.17 inches in diameter. The opening and closing mechanism 39 allows the STR unit 1 to be installed on a wide range of conductor diameters without changing the upper jaws 6 and the lower jaws 7 while maintaining sufficient contact between the upper magnetic core 40 and the lower magnetic core 14 to complete the magnetic circuit of the power supply transformer 55 of the STR unit 1 which derives its power from the current flowing through the conductor C to power a power supply module 60 of FIG. 9. Because the STR unit 1 derives power from the conductor C, batteries or solar cells are not required to power the STR unit 1. The STR unit 1 is powered at all times when current is flowing in the conductor C, even at current levels as low as 6.8 amperes and still process data and transmit data at 1 watt power levels because of the low threshold of the power supply module 60.

Maintaining a minimum magnetic reluctance insures that a power supply transformer 55 (FIGS. 8 and 9) will provide the needed secondary voltage $V_2$ and secondary current $I_2$ to operate the power supply transformer 55, sensor electronics module 63, and transmitter/receiver 64. The power supply transformer 55 includes the upper magnetic core 40, the lower magnetic core 14, and a coil winding 56. The upper magnetic core and the lower magnetic core form a window W for accepting the conductor C.

Figure 12:
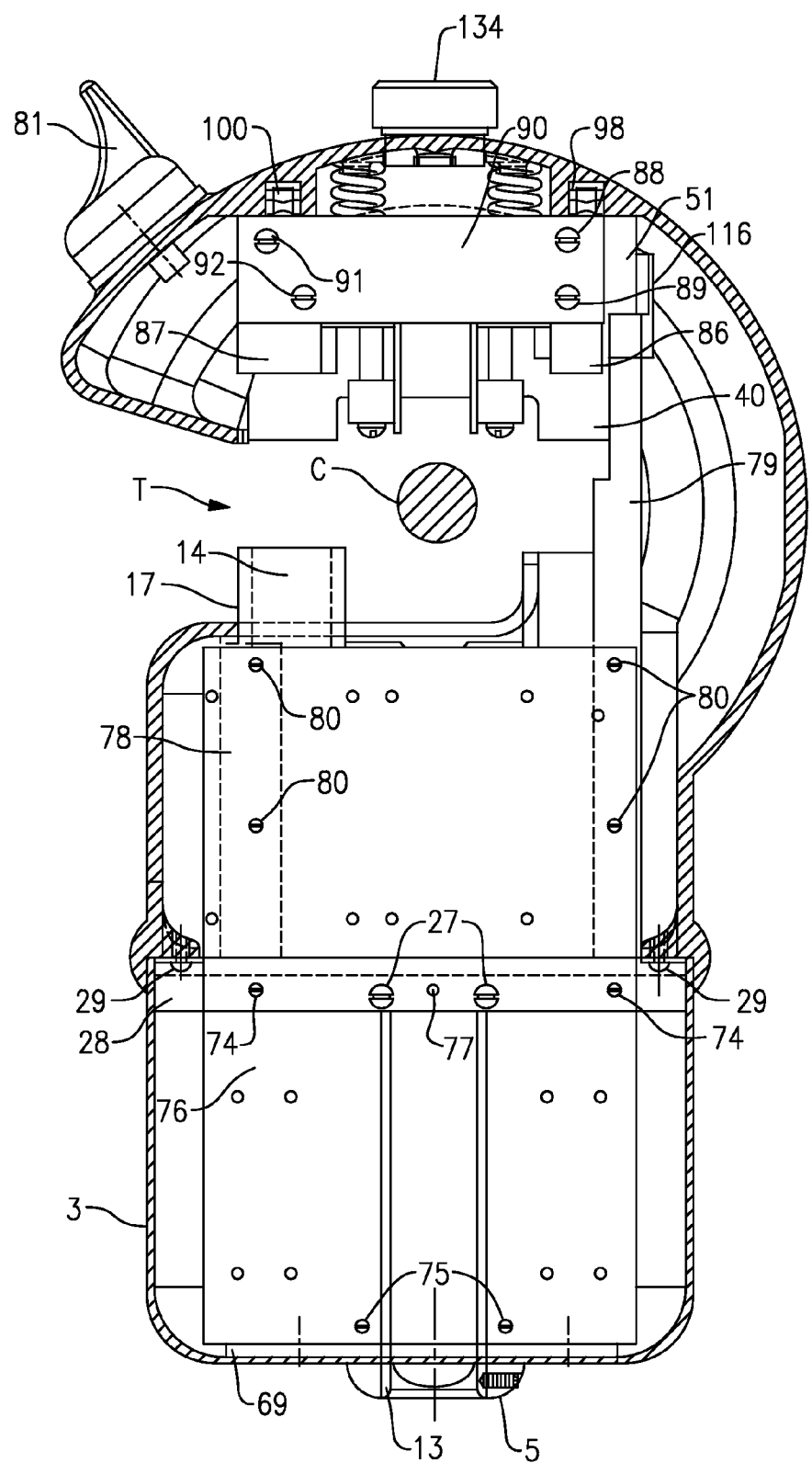
FIG. 12 illustrates a cross-sectional view taken along line B-B of FIG. 2.

The number of secondary turns $N_2$ of wire on the coil winding 56 are optimized to produce the required secondary voltage $V_2$ and secondary current $I_2$ with a minimum of current $I_1$ in the conductor C. The coil winding 56 is held in place by two coil bobbins 57 which are supported laterally by the two upper core blocks 43 and the two lower core blocks 44. Secondary leads 58a and 59a of coil windings 58 and 59, respectively, are connected to the power supply module 60 which maintains the same level of secondary voltage across leads 61 and 62 for the sensor electronics module 63 and the transmitter/receiver 64 even though the primary current may range from 34 amperes up to 1000 amperes. Lower primary currents of 6.8 amperes are achievable with the low threshold current power supply module 60. The power supply module 60 contains an energy storage device 256 (FIG. 13) which can power the transmitter/receiver 64 when the conductor C current ceases to flow. A transmitting and receiving antenna 81 for the on-board transmitter/receiver 64 is mounted on the upper housing 2 (FIG. 12).

Locating the coil winding 56, 58, and 59 on the upper magnetic core 40 allows the heat from the coil winding 56, 58, and 59 to escape through a vent 65 (FIG. 1) in the upper housing 2. When the conductor sensor S located within the STR unit 1 measures the temperature of the conductor C, it is important that the heat from the coil windings 56, 58, and 59 does not affect the temperature of the conductor C or the conductor temperature sensor S, which is in electrical communication with the sensor electronics module 63. As shown in FIG. 6, a thermally insulating barrier 66 located below the coil windings 56, 58, and 59, allows for a more accurate temperature reading of the conductor temperature by blocking heat from the coil windings 56, 58, and 59.

FIGS. 10-12 and 13 illustrate the lower magnetic core 14 with the lower core covers 17, the lead screw 22, the hotstick guide tube 13, and other related parts in both exploded and collapsed views. The hotstick guide tube 13 is anchored at the top with the through bolts 27 that extend through the bottom support 28 and the hotstick guide support 26. A round cylindrical milled slot 67 is located along opposing sides of the top of the hotstick guide tube 13 to accept the through bolts 27 that support the hotstick guide tube 13.

A central hole 70 extends through a base plate support 68 and a base plate 69 for accepting a bottom portion of the hotstick guide tube 13. The base plate support 68 and the base plate 69 are connected to each other with four identical threaded screws 71. The hotstick guide tube 13 is attached to the base plate support 68 and the base plate 69 with set screws 72 and 73. Left and right side panels 76 of FIG. 12 are attached to the base plate support 68 and the bottom support 28 for the lower core 14 with the use of two identical screws 74 extending through the bottom support 28 and the side panel 76 and at the bottom with two identical screws 75 extending through the side panel 76 and the base plate support 68.

The threaded bushing 25 rests on top of the hotstick guide tube 13 and is prevented from turning relative to the hotstick guide tube 13 using a set screw 77. The left and right side panels 76 not only provide added strength, but also provide the physical space to mount the power supply module 60, the transmitter/receiver 64, the sensor electronics 63, and support left and right lower core guides 78 and 79.

The left lower core guide 78 and a right lower core guide 79 are "U" shaped and guide the opening and closing mechanism 39 such that the lower magnetic core 14 is aligned with the upper magnetic core 40. Each of the left and right lower core guides 78 and 79 are attached to the left and right side panels 76 with four threaded screws 80. The lower housing 3 is placed over the hotstick guide tube 13 at the bottom and fitted up to the base plate 69 and held in place with the collar 5. This means that once the collar 5 is removed, the lower housing 3 can be removed thus allowing access to the power supply module 60, sensor electronics module 63, and the transmitter/receiver 64 of FIG. 9 mounted inside and on the left and right side panels 76 for easy maintenance and repair.

FIGS. 7 and 12-15 illustrate an upper magnetic core subassembly 40a mounted to the upper housing 2. The left and right core shoes 50 and 51 support the upper magnetic core 40 such that the upper magnetic core 40 can move freely up and down inside the left and right shoes 50 and 51. The left and right core shoes 50 and 51 are attached to the upper housing 2 using four support blocks 86 and 87 of FIG. 14, right and left upper core guides 90 and 93, and four vertical through bolts 94, 95, 96, and 97.

The upper magnetic core subassembly 40a can be inserted through the throat T and fastened to the inside of the upper housing 2 of FIGS. 12-15. A top portion of the upper housing 2 is "C" shaped which provides a surface on the inside for mounting a "C" loop coil 156 for measuring the power line frequency current (60 Hz or 50 Hz) and a "C" loop coil 157 for measuring lightning stroke current (see FIGS. 13, 42, and 43).

The right core shoe 51 has two identical threaded holes 82 and 83 on the front and back for a total of four, and left core shoe 50 has two identical threaded holes 84 and 85 on the front and back for a total of four as shown in FIGS. 7 and 14. As shown in FIG. 14, two identical support blocks 86 on the right side are placed on the front and back of the right core shoe 51 and two identical support blocks 87 are placed on the front and back of the left core shoe 50.

To align the two right side support blocks 86 with the two sets of threaded holes 82 and 83 on the right side of the right core shoe 51, threaded screws 88 and 89 are first inserted into the upper and lower holes in the right side upper core guide 90 and then through the two holes in the right support block 86 and screwed into the accommodating threaded holes 82 and 83 of the right core shoe 51. The two left side support blocks 87 are held in alignment with the left core shoe 50 by first inserting two threaded screws 91 and 92 through the other end of the right side upper core guide 90 and then through the holes in the left side support block 87 and screwed into the threaded holes 84 and 85 of the left core shoe 50. The same process is repeated on the back side by connecting support blocks 86 and 87 to the left upper core guide 93 with the backside of the right core shoe 51 and the back side of the left core shoe 50.

The purpose of the upper core guides 90 and 93 is to insure the two long vertical through bolts 94 and 95 placed through the vertical holes in the two right side support blocks 86 and two long vertical through bolts 96 and 97 placed through the vertical holes in the two left side support blocks 87 line up with the four threaded holes in four threaded inserts 98, 99, 100, and 101, which are embedded in the casting of the upper housing 2. The two right side support blocks 86 are prevented from falling down by inserting the back of a right side upper jaw holder 102 and the back of the left side upper jaw holder 103 over the vertical through bolts 94 and 95 and threading nuts 104 and 105 onto the two vertical through bolts 94 and 95 and tightening them down, respectively. The two left side support blocks 87 are held in place by inserting the vertical through bolts 96 and 97 through the front hole in the right side upper jaw holder 102 and the front hole in the left side upper jaw holder 103 and threading two nuts 106 and 107 on the vertical through bolts 96 and 97 and tightening them down, respectively.

Four threaded through standoffs 108, 109, 110, and 111 are screwed onto the four vertical through bolts 94, 95, 96, and 97, respectively. The thermal barrier 66 is placed over the four bottom holes of the standoffs 108, 109, 110, and 111 and screwed to the standoffs 110 and 111 on the front left side with two flat head screws 112 as shown in FIG. 15.

Figure 15:
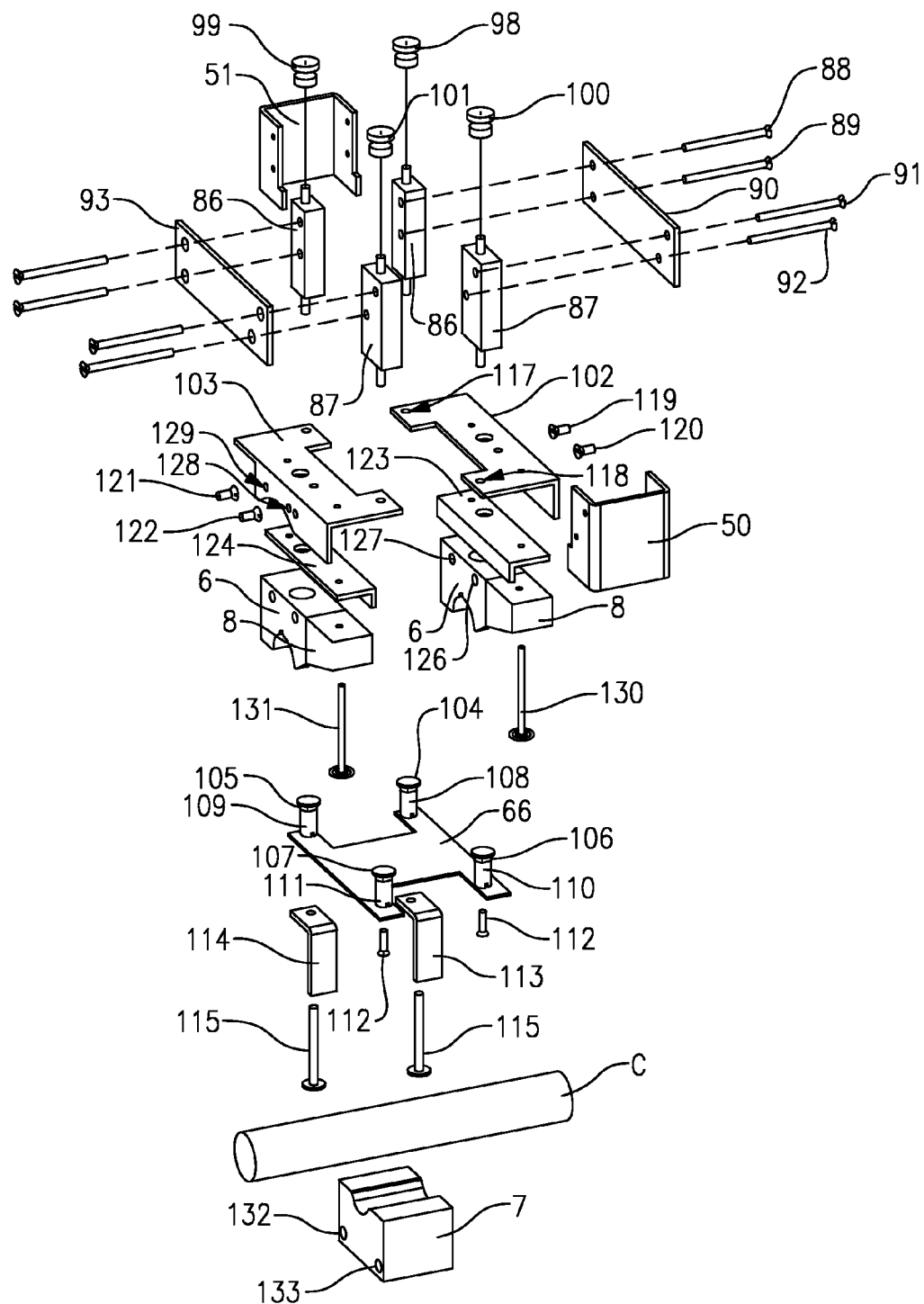
FIG. 15 illustrates an exploded view of an upper magnetic core mount and the upper and lower jaws.

FIGS. 2 and 15 illustrate casting fillers 113 and 114 located on the back left and back right sides of the STR unit 1 and secured with round head screws 115 which are first inserted through holes in the casting fillers 113 and 114 and then through the two back holes on the right and left side of the thermal barrier 66 and into the standoffs 108 and 109, respectively.

After the upper magnetic core subassembly 40a is mounted, the left and right lower core guides 78 and 79 including the opening and closing mechanism subassembly 39 and the left and right side panels 76 are inserted through the bottom of the upper housing 2 (See FIG. 12). Four screws 29 are inserted through the two holes on the left and the two holes on the right of the bottom support 28 and screwed into the threaded holes of the upper housing 2. It should be noted that during the insertion process, the right lower core guide 79, shown in FIG. 12, slides around the outside surface of the right core shoe 51 and underneath a tab 116 at the top as a weldment on the right upper side of the right core shoe 51.

As shown in FIG. 12, the tab 116 insures that the right lower core guide 79 fits precisely around the outside of the right core shoe 51 to provide a near perfect alignment of the lower magnetic core 14 with the upper magnetic core 40. The precise alignment between the upper magnetic core 40 and the lower magnetic core 14 reduces magnetic reluctance by decreasing the air gaps 54. This results in a decrease in the threshold current for the operation of the power supply module 60.

Referring to FIGS. 14 and 15, the right side upper jaw holder 102 and the left side upper jaw holder 103 support the two upper jaws 6 and the jaw inserts 8. The long vertical through bolts 96 and 97 which are screwed into the threaded inserts 100 and 101 at the top and on the inside of the upper housing 2 fit through top holes 117 and 118 on the back and front of the right side upper jaw holder 102 on the right side. Also, flush mount screws 119 and 120 are inserted on the back and through corresponding holes in the right side upper jaw holder 102 and are screwed into the upper housing. The flush mount screws 119 and 120 are installed before the upper jaws 6 and inserts 8 are mounted to the right side upper jaw holder 102. The same arrangement for mounting the left side upper jaw holder 103 is followed using screws 121 and 122.

Right and left upper jaw keepers 123 and 124 prevent the upper jaws 6 from dropping down on the inside, because spring pins 126 and 127 are located on the outside and when depressed snap into the holes 128 and 129 of the right side upper jaw holder 102. The same procedure is followed with the left upper jaw keeper 124.

The jaw inserts 8 on the right and left sides of the STR unit 1 and in front of the upper jaws 6 are held in place by inserting threaded bolts 130 and 131 into each insert 8 and through the right and left keepers 123 and 124 and screwing into the upper jaw holders 102 and 103. The spring pins 132 and 133 are included in the lower jaw 7 which when depressed snap into the two holes 15 in the lower jaw holder 16.

Figure 9:
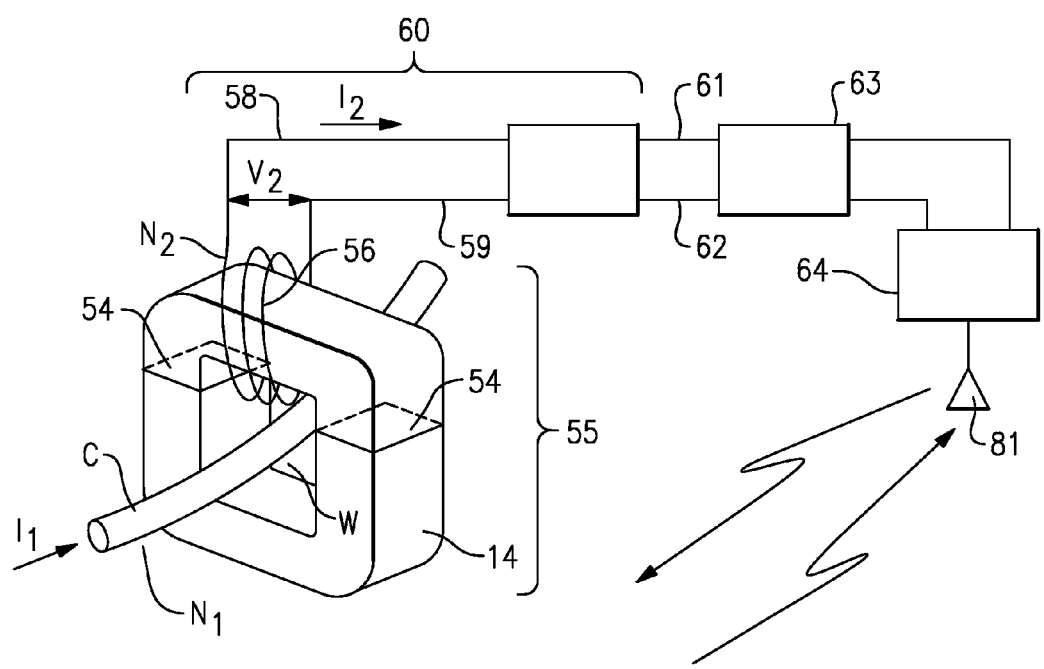
FIG. 9 illustrates a schematic view of the line mounted power supply, electronics and transmitter-receiver of the STR unit.
Figure 13:
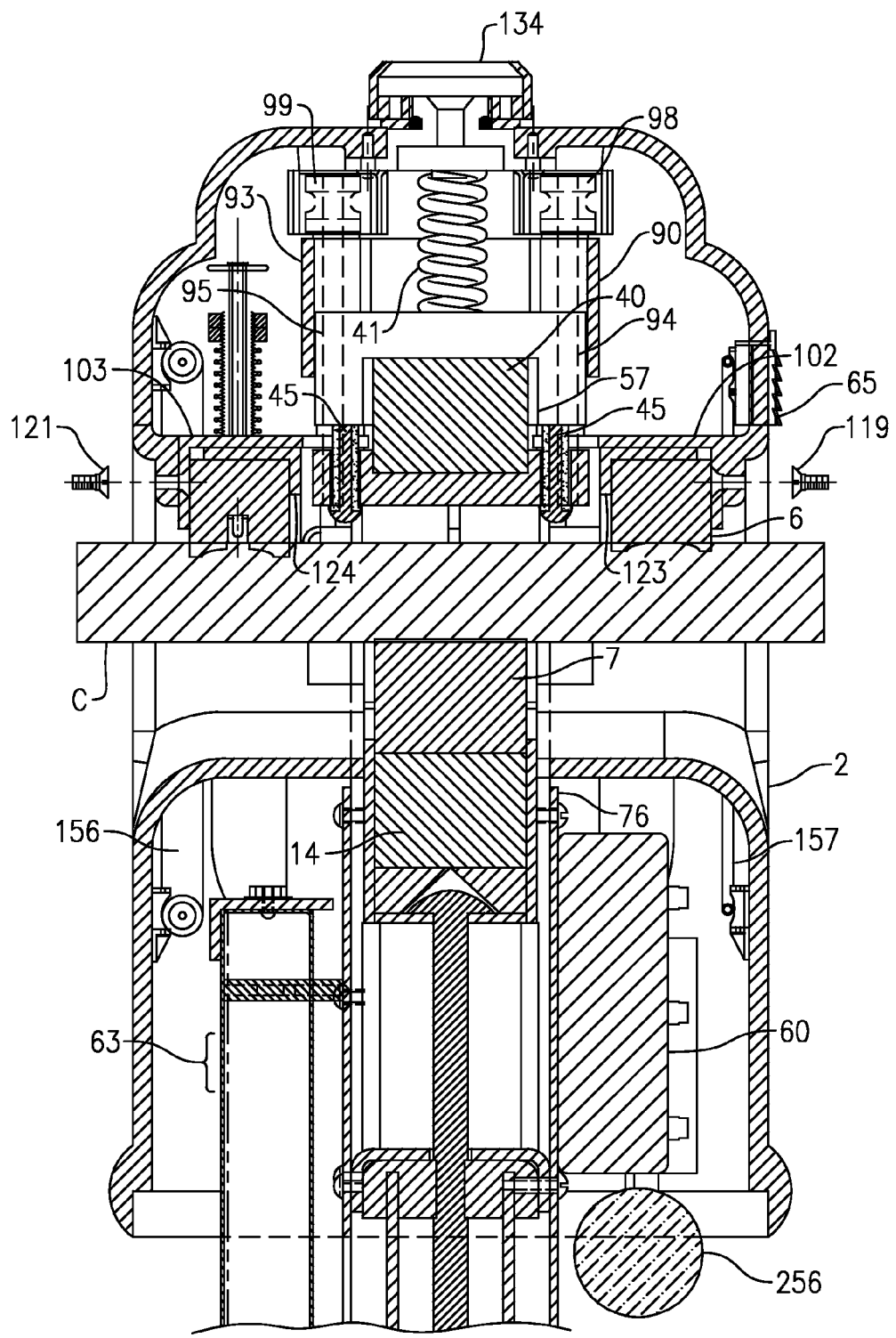
FIG. 13 illustrates a cross-sectional view taken along line C-C of FIG. 1.

The transmitting and receiving antenna 81 for the on-board transmitter and receiver 64 shown in FIG. 9 is mounted on the housing 2. The antenna 81 is displayed in FIGS. 1 and 2 and is installed on the top left side in FIG. 1. The solar sensor assembly 134 is located at the top of this housing and on its vertical centerline (FIG. 13). The small hole 140 located directly to the right of the conductor C allows access and adjustment of the electric power line sag sensor 140 (FIG. 1).

Electric power systems are either delta connected or wye connected three phase or single phase systems. In one example, the STR unit 1 will be used to measure the voltage of a single phase line to line voltage of a delta connected system as shown in FIGS. 16, 17, and 18.

Figure 16:
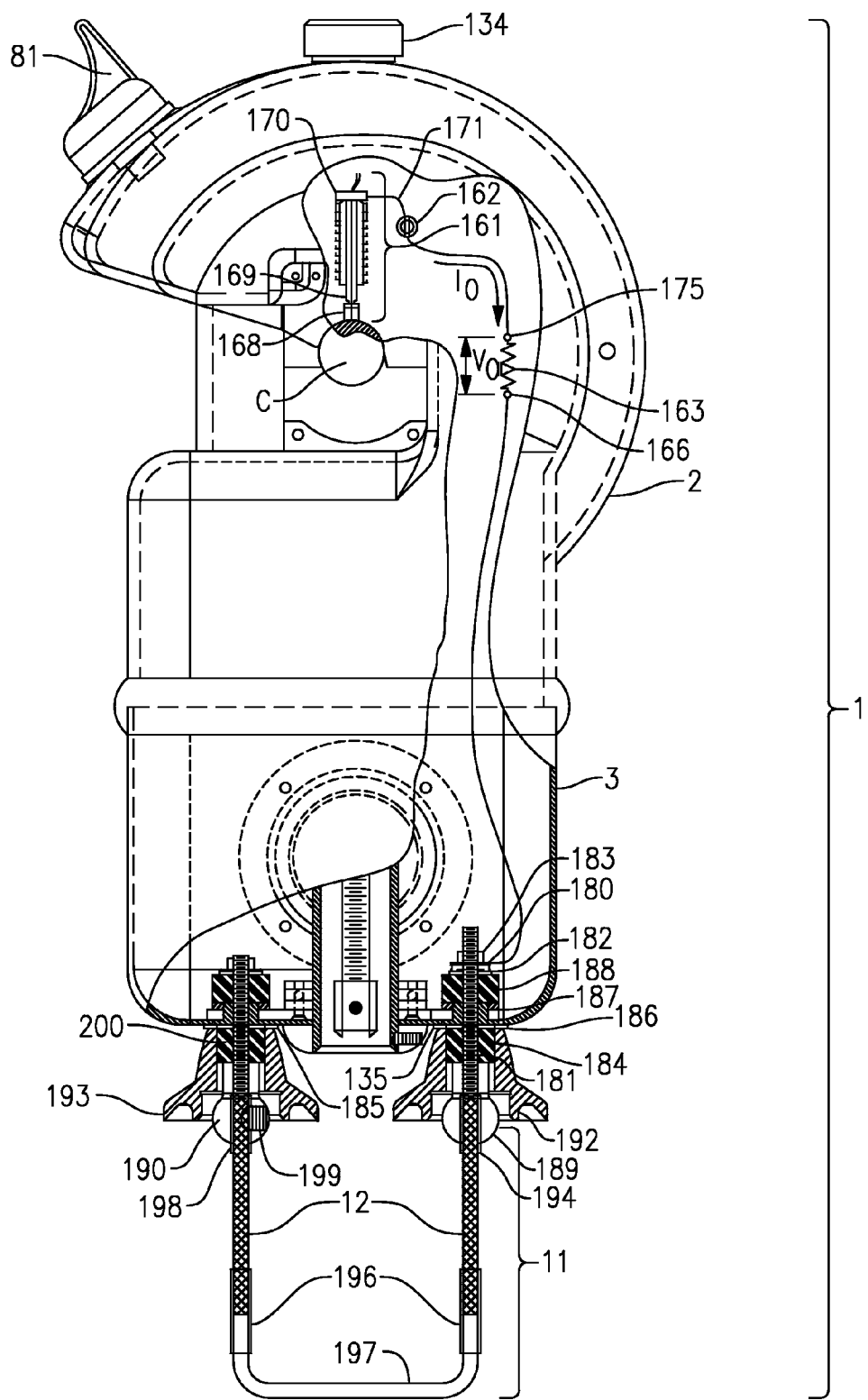
FIG. 16 illustrates a cutaway view of FIG. 1 showing a portion of voltage measuring components.
Figure 17:
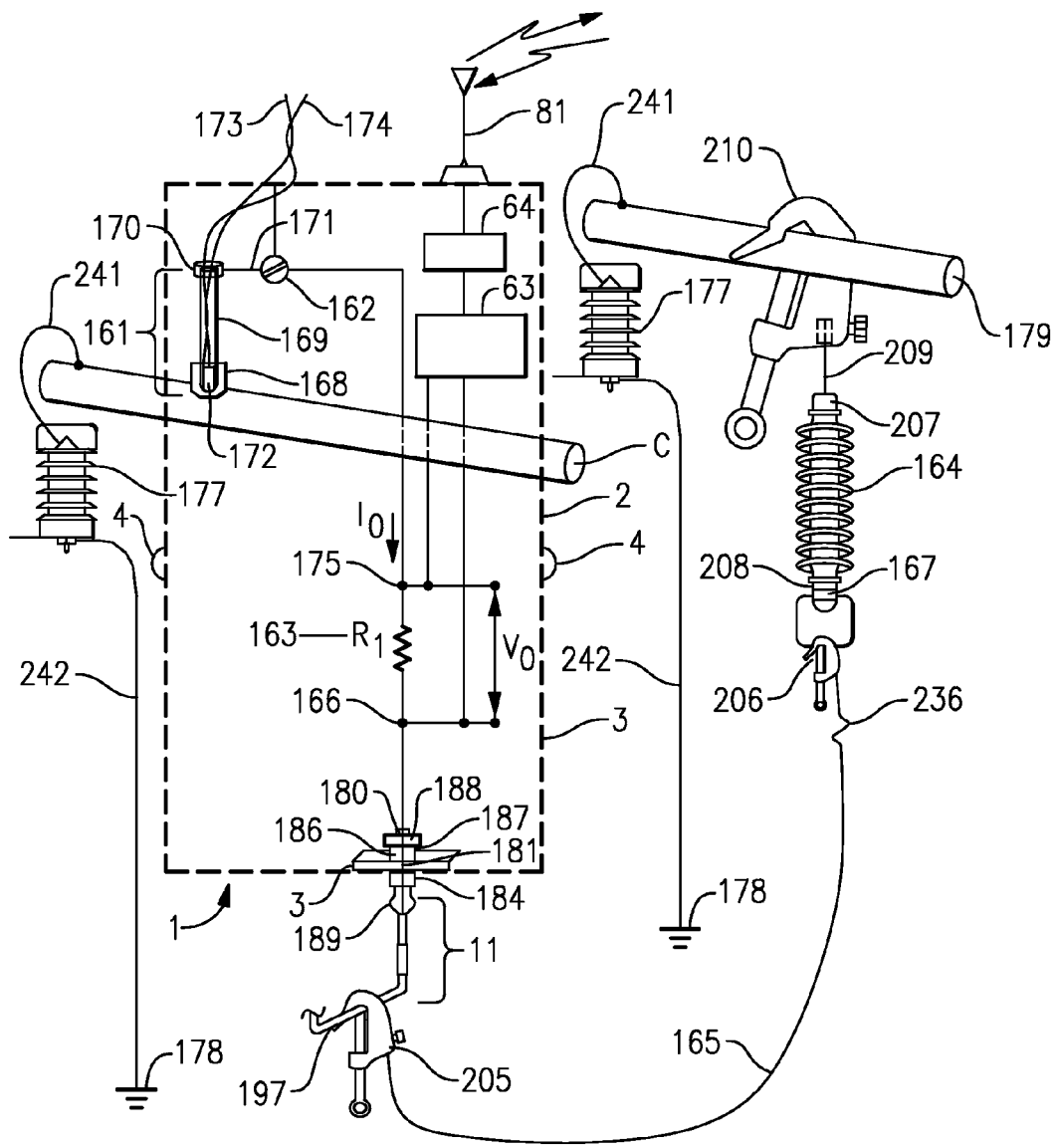
FIG. 17 illustrates a schematic view of a single phase line to line voltage sensing circuit for a delta connected ungrounded power system.
Figure 18:
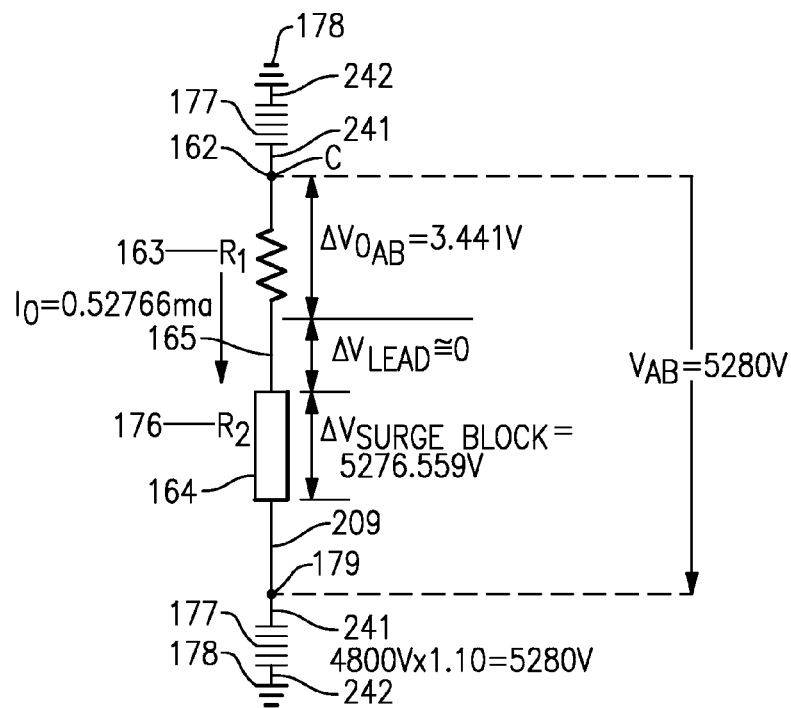
FIG. 18 illustrates a schematic view of a single phase line to line voltage, phase A to phase B delta connected ungrounded power system.

The STR unit 1 includes the following elements as shown in FIGS. 16 and 17 to aid in creating a low cost and highly accurate voltage measuring system: (1) a virtual grounding device 161 which grounds the STR unit 1 to the phase A conductor C with the use of a case ground 162 which is connected to the upper housing 2 and the lower housing 3; (2) a measuring resistor 163 generally accurate within 0.1%; (3) a surge block 164; and (4) an electrically conductive jumper 165 including hot line clamps 205 and 206 at each end, which connects a bottom terminal 166 of the measuring resistor 163 to the base of the surge block 164 at a bottom end cover 167. The surge block 164 has a hot line clamp 210 attached to the top of the surge block 164 for connecting to a phase B conductor 179.

FIG. 17 illustrates a schematic view of an example single phase line to line voltage sensing circuit for a delta connected ungrounded power system. In this example, the STR unit 1 measures the phase A conductor C to the phase B conductor 179 voltage. The virtual grounding device 161, which is in electrical contact with the phase A conductor C, has an electrically conductive shoe 168, which is attached to an electrically conductive protection tube 169. The electrically conductive protection tube 169 is connected to a ring connector 170 at the top. The ring connector 170 is electrically connected to the electrically conductive protective tube 169 and has a wire lead 171 which is connected to the case ground 162. Inside and at the bottom of the electrically conductor protective tube 169 is a conductor temperature sensor 172 with signal output leads 173 and 174. (See FIG. 17). With the virtual grounding device 161 connected to the phase A conductor C and to the case ground 162, the entire upper housing 2 and the lower housing 3 of the STR unit 1 are at the same voltage potential as the phase A conductor C. This creates a "bird-on-the-wire" condition, where there is no potential difference between the bird and the live wire. The bird in this case is the STR unit 1 upper and lower housings 2 and 3. Therefore, the phase A conductor C voltage increases with respect to earth ground during lightning strokes, switching surges or other transient voltages. The STR unit 1 upper and lower housings 2 and 3 follow the increased voltage eliminating a voltage difference between the STR unit 1 upper and lower housings 2 and 3 and the conductor C.

The measuring resistor 163 is connected in series to case ground 162 at an upper terminal 175 and the surge block 164 with the use of the jumper 165. Turning to FIG. 17, it should be noted that the output current $I_O$ which will flow from the case ground 162 through the voltage measuring resistor 163 is defined as the line to line voltage ($V_{AB}$ in this case) divided by the sum of $R_1$ and $R_2$ where $R_1$ is the resistance of the measuring resistor 163 and $R_2$ is the resistance of the surge block 164, which is connected to the phase B conductor 179.

In the illustrated example shown in FIGS. 17 and 18, the phase to phase voltage $V_{AB}$ is 10 percent higher than the nominal phase to phase voltage of 4800 volts or 5280 volts rms (root mean square), the rms current $I_O$ is 0.52766 milliamperes, and the rms voltage drop $\Delta V_{OAB}$ across the measuring resistor is 3.441 volts. This voltage drop of 3.441 volts is directly proportional to the phase to phase voltage of 5280 volts and there is no phase shift. For accurate phase to phase voltage measurements, the resistances $R_1$ of the measuring resistor 163 and $R_2$ of the surge block 164 should have an accuracy of approximately 0.1 to 1.0 percent and have neither a capacitive nor an inductive component. The high accuracy measuring resistor 163 can be purchased commercially with non-inductive and non-capacitive components. This will eliminate phase shift between the actual phase to phase voltage being measured and the measured output voltage $\Delta V_{OAB}$.

However, very high rms voltages are applied across the surge block 164, and in this case 5276.559V is applied as a voltage drop across the surge block 164. The sum of the measured voltage and the voltage drop across the surge block 164 must be equal to the phase to phase voltage being measured, which is $V_{AB}$=5280 volts rms. Therefore, there can be no capacitive and inductive components in the resistance $R_2$, or 176 of FIG. 18 of the surge block 164. The surge block 164 shown in FIG. 17 contains an internal proprietary voltage dropping element (VDE) which is a non-capacitive and non-inductive element that is not affected by the operating temperature range that the STR unit 1 will experience and is nearly non-dissipative. As a result, the measured output voltages have an accuracy of 0.1 percent in this case. The measured normal steady state output voltage $V_O$ sinusoidal 60 Hz or 50 Hz waveforms are then fed into the sensor electronics module 63 of FIG. 17 that contains signal conditioning and a microprocessor where data can be integrated and transmitted with transmitter-receiver unit 64 via the antenna 81. The data is transmitted to a remote site for data processing and for operating and controlling the distribution circuit.

Figure 19:
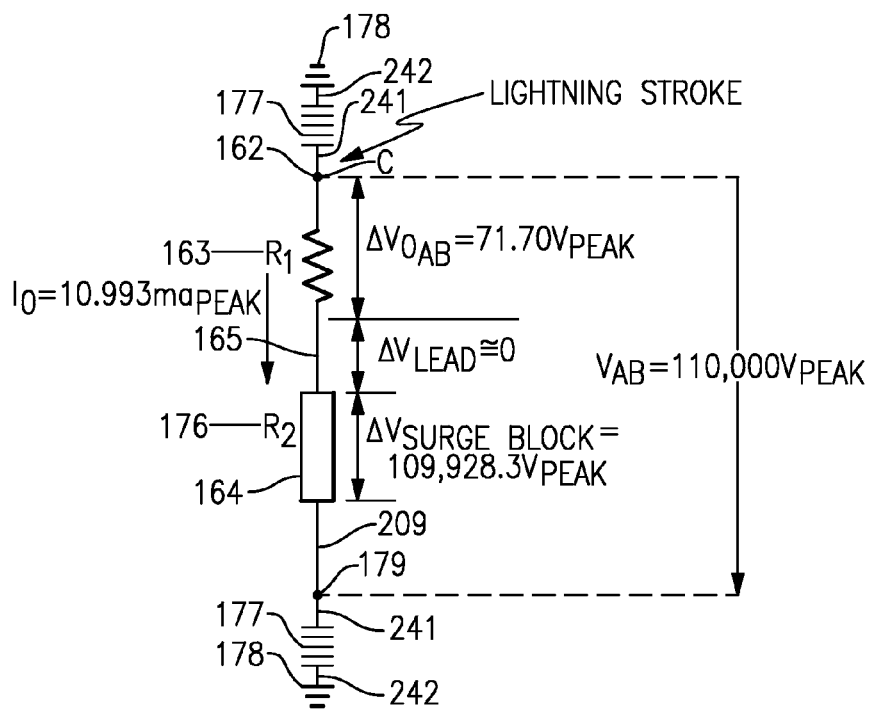
FIG. 19 illustrates a single phase line to line voltage, phase A to phase B delta connected ungrounded power system with lightning stroke of +110,000 volts peak applied to phase A.

During lightning strokes as illustrated in FIG. 19, the power system may see considerably higher voltages than during normal steady state operation. The typical basic impulse insulation level (BIL) for distribution transformers and other equipment insulation is 95,000 volts peak. In this case, the example shown for the delta connected system of FIG. 19 is a lightning stroke of +110,000 volts peak. The resultant peak voltage drop across the measuring resistor 163 is only 71.70 volts peak, the $I_O$ current is 10.993 milliamperes peak and the voltage drop across the surge block 164 is 109,928.3 volts peak. The much higher peak voltage drop across the surge block 164 is not a problem because it is rated for a BIL of 113,000 volts peak for distribution line voltage applications. Much higher values of BIL are used for transmission line voltage applications.

However, the voltage sensing apparatus design shown in FIG. 17 provides, as an option, an additional margin of safety against even higher lightning stroke magnitudes by installing lightning arresters 177 on the phase A conductor C and the phase B conductor 179 and connecting them to an earth ground 178. The normal practice is to apply arresters 177 so they have an rms voltage rating at least five percent above the maximum rms line to neutral voltage for any normal or fault condition. The BIL for the STR unit 1 surge block 164 must be higher than the maximum discharge voltage across the arrester 177. If a 9 kV rms arrester rating is applied, which is very conservative, then a 200,000 ampere maximum peak lightning stroke would be expected to cause a maximum discharge voltage of the arrester 177 of only 53 kV. The selection of 200,000 ampere peak stroke current represents 99.9987% of all strokes. In other words, very few strokes with peak stroke currents are higher than 200,000 amperes occur in nature. Since the maximum discharge voltage of this 9 kV arrester 177 rating of 53 kV is well below the 113 kV BIL rating of the surge block 164, then the probability of insulation failure for the surge block 164 and the STR unit 1 is very low.

Returning to FIGS. 16, 17, and 20, the measuring resistor 163 includes the bottom terminal 166 which is connected to a ring connector 180 and is attached to an electrically conductive threaded hinge post stud 181 with backup washers 182 and nut 183. The hinge post stud 181 is electrically insulated from the upper housing 2 and the lower housing 3, because the voltage is less than the virtual ground voltage of 5280 volts on the upper and lower housings 2 and 3 in the example of FIG. 18 by the voltage drop $\Delta V_{OAB}$=3.441 volts.

To electrically insulate the hinge post stud 181 there are three electrical insulators that are slipped over the hinge post studs 181 and 200. Hinge post insulators and 191 are installed first followed by the hinge post rubber washers 185 and 202 and then standoff insulators 186 and 201 are pushed from the bottom through the baseplate holes 135 and 136 of FIG. 20. Then insulating washers 187 and 203 are placed over the standoff insulators 186 and 201 and insulating spacers 188 and 204 are placed on top, followed by the backup washers 182 and the nut 183. An electrically conductive right hinge post 189 is screwed onto the bottom of the hinge post stud 181 and the nut 183 is tightened down on the ring connector 180. The lower housing 3, as soon as the left side is assembled on an electrically conductive left hinge post 190, may now be pushed up over the hinge post insulators 184 and 191 and the collar 5 may now be installed over the hotstick guide tube 13 and the set screw 14 tightened to hold the lower housing 3 into the bead 4.

To prevent the snow or ice accumulation on the lower housing 3 from shorting out the hinge posts 189 and 190, which are at a lower voltage than the housing 3 at the line voltage, flexible rubber insulating weather sheds 192 and 193 are stretched tightly over the hinge post insulators 184 and 191.

Figure 20:
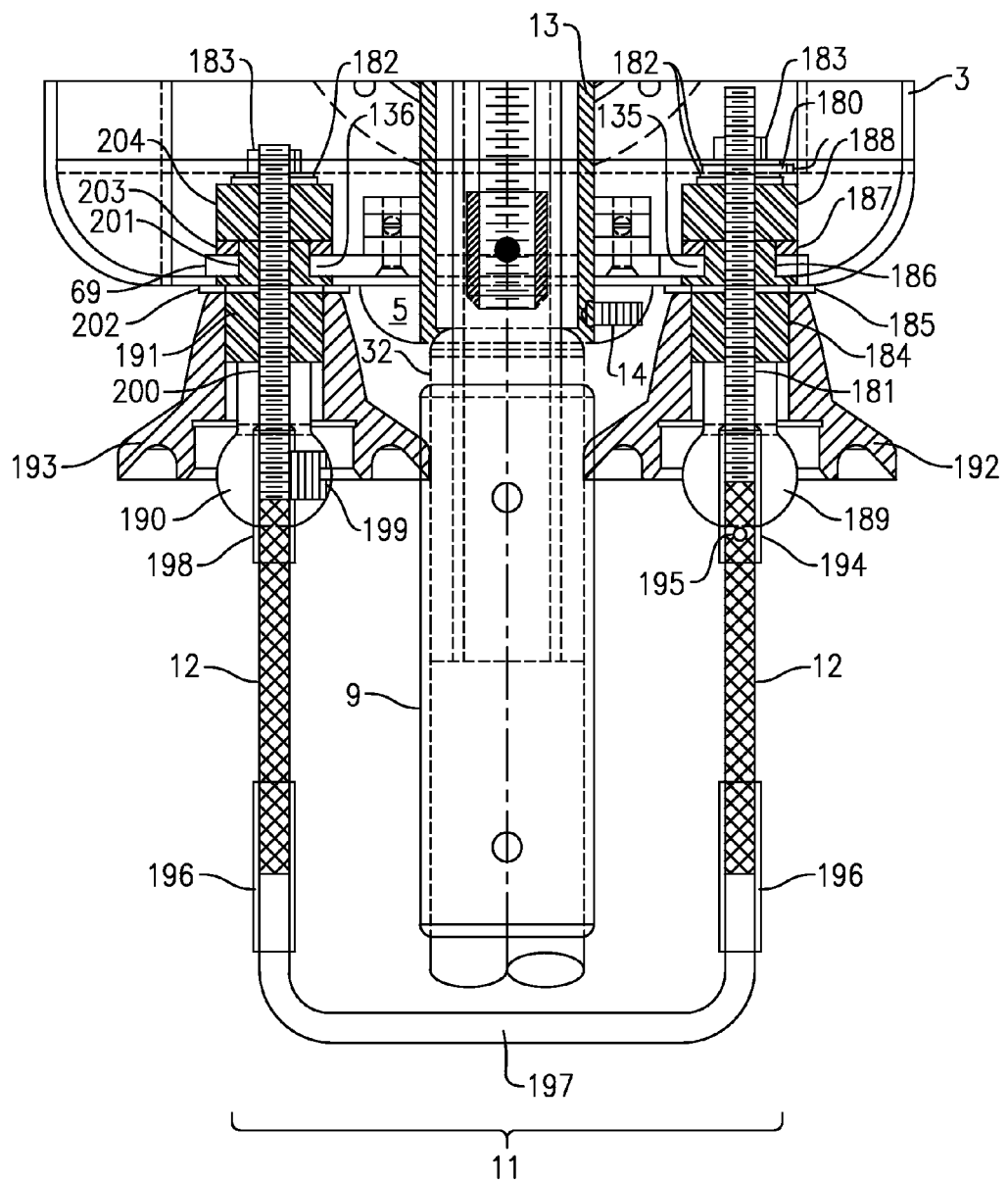
FIG. 20 illustrates a hinge post insulator and weather shed assembly.

At this point the stirrup assembly 11 of FIGS. 3, 4, and 20 is attached first to the hinge post stud 181 on the right side. The stirrup assembly 11 has a right side threaded sleeve 194 which is placed inside the right hinge post 189 and threaded onto the hinge post stud 181. A hole 195 in the lower portion of the right side threaded sleeve 194 is used to mechanically tighten the right side threaded sleeve 194 onto the hinge post stud 181.

The braided flexible electrically conductive strap 12 is welded to the bottom of the right side threaded sleeve 194 and is compressed inside the top of a sleeve 196. A stirrup 197 is also compressed to the bottom of the sleeve 196. There is one continuous non-interrupted electrically conductive path from the stirrup 197 through to the bottom terminal 166 of the measuring resistor 163 of FIG. 17. Also, note that on the left side of the stirrup assembly 11 of FIG. 20 is a similar sleeve 198 which is installed inside the left hinge post 190 with a set screw 199.

The electrically conductive left hinge post 190 is screwed onto a threaded stud 200. The threaded stud 200 is inserted inside the hole of the left hinge post insulator 191. A rubber seal 202 followed by a standoff insulator 201 is pushed up through the hole 136 in the base plate 69 shown in FIG. 20. A hinge post insulating washer 203 is placed over the standoff insulator 201 and on top of the base plate 69. Finally a hinge post insulator spacer 204 is inserted over the stud and tightened down with the nut 183 and the backup washer 182.

By removing the set screw 199, the sleeve 198 is free to drop down allowing the lower housing 3 to be removed once the weather sheds 192 and 193 are pulled off and the collar 5 is removed. Because the weather sheds 192 and 193 are made of a flexible electrically insulating material, the hotstick assembly 10 of FIG. 4 easily passes by the weather sheds 192 and 193 and into the interior hole of the hotstick guide tube 13. The stirrup assembly 11 could also be constructed in the form of a ring and only attached to the right hinge post 189. It is desirable to have a continuous electrical path from the bottom terminal 166 of the measuring resistor 163 shown in FIG. 17, which is at a slightly lower voltage than the top of the measuring resistor 163 at the upper terminal 175 (due to the voltage drop through the measuring resistor 163) and onto the bottom end cover 167 of the surge block 164.

However, the electrical path from the bottom terminal 166 to the bottom end cover 167 of the surge block 164 must be electrically insulated from the upper and lower housings 2 and 3, because the virtual grounding device 161, which is at the voltage of the conductor C, is grounded to the case ground 162 which is the same voltage as the upper and lower housings 2 and 3. As a result, the electrical path from the bottom terminal 166 and bottom end cover 167 is electrically insulated from the upper and lower housings 2 and 3 using the hinge post insulator 184, the standoff insulator 186, the insulating washer 187, and the insulating spacer 188 as shown in FIG. 17.

Figure 21:
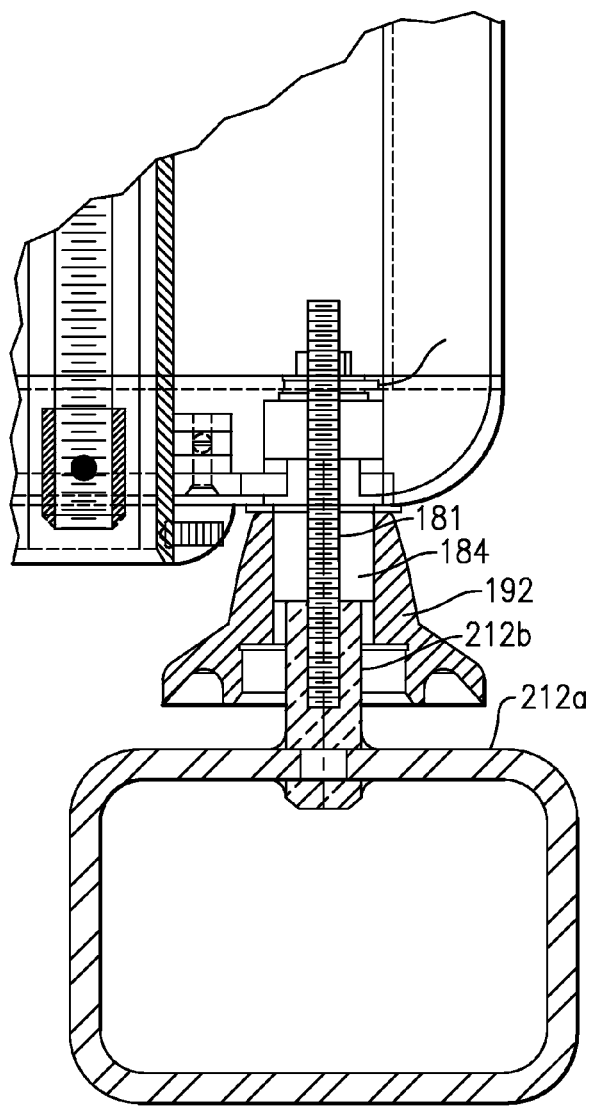
FIG. 21 illustrates a cutaway view of FIG. 16 showing a ring connector in place of a stirrup assembly.
Figure 22:
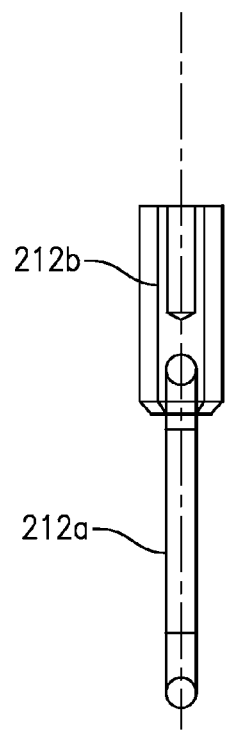
FIG. 22 is an end view of FIG. 21.

In another embodiment, an electrically conductive ring assembly can replace the stirrup assembly 11 of FIG. 16 as shown in FIGS. 21 and 22. An electrically conductive connector 212b replaces the right hinge post 189 and includes a ring 212a which is attached to the bottom of the electrically conductive connector 212b. The electrically conductive connector 212b is screwed on the bottom of the threaded hinge post stud 181.

Figure 23:
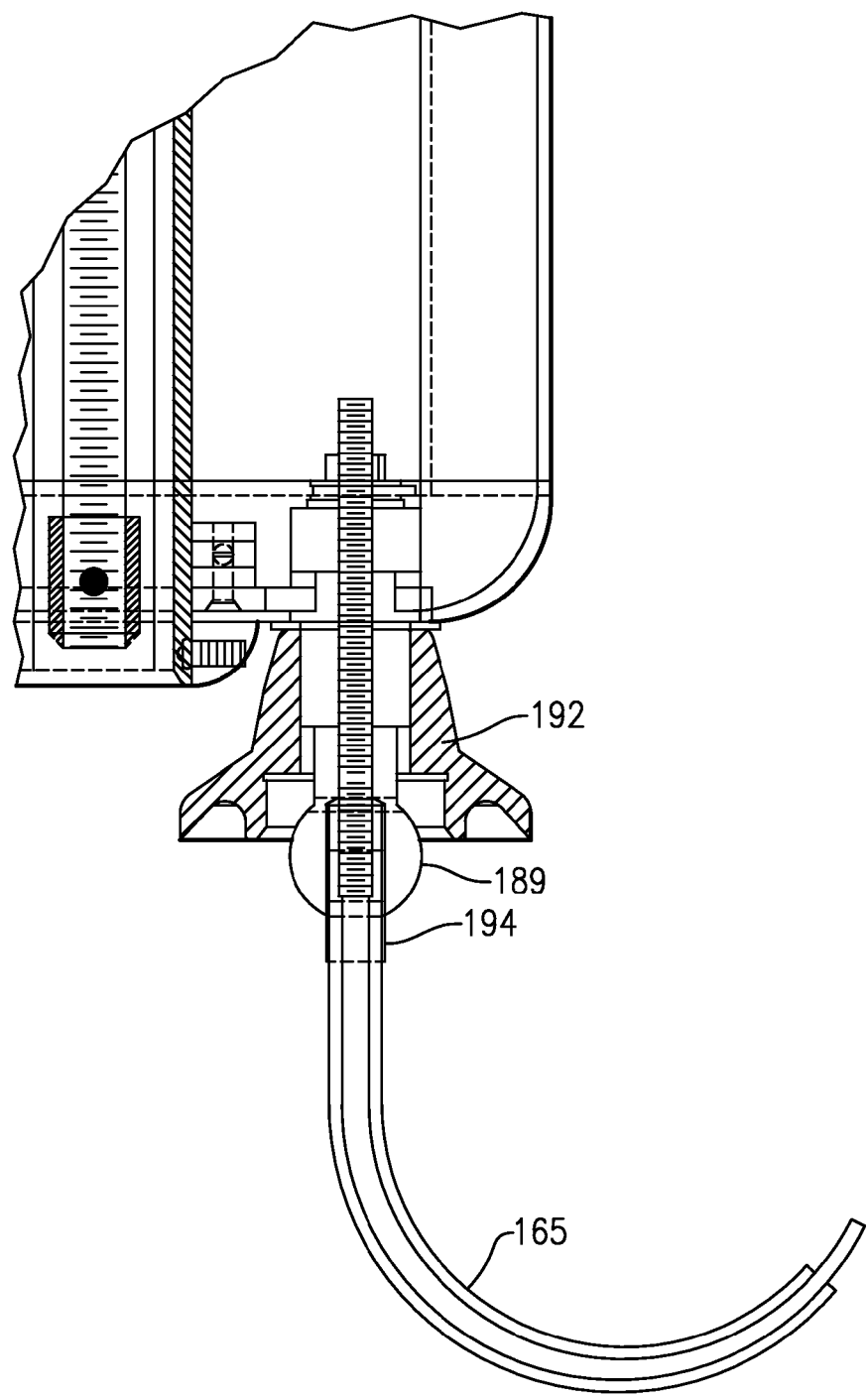
FIG. 23 is a cutaway view of FIG. 16 showing a single jumper in place of the stirrup assembly.

In yet another example, the stirrup assembly 11 is replaced with the jumper 165 of FIG. 17 which is directly connected inside the right side threaded sleeve 194 as shown in FIG. 23. The jumper 165 is an electrically insulated covered wire. Although the latter two embodiments may be simpler in design than the stirrup assembly 11, they may create an unbalanced torque on the bottom of the STR unit 1 when the hot line clamp 205 of FIG. 17 is attached to the ring 212a of FIG. 21, or the hot line clamp 206 of the jumper 165 of FIG. 23 is mechanically attached to the bottom end cover 167 of FIG. 17. If an unbalanced torque does occur, then the STR unit 1 will not hang vertically on the conductor C. This condition is not that relevant unless the STR unit 1 is also measuring the solar radiation using the sensor 134 of FIG. 16. To provide accurate solar radiation measurements, the sensor 134 should remain horizontal and will only remain in this position when the STR unit 1 hangs vertically on the conductor C.

The only reference to electrical insulating elements has been to the hinge post insulator 184, the standoff insulator 186, the insulating washer 187, and the insulating spacer 188 of FIG. 16. This is because of the very small voltage difference applied across the hinge post insulator 184, the standoff insulator 186, the insulating washer 187, and the insulating spacer 188 of 3.441 volts from the bottom terminal 166 to the upper and lower housings 2 and 3, as shown in FIGS. 17 and 18 for the single phase delta connected system example of the 4800 volt system of 5280 volts phase to phase. Even during lightning strokes of +110,000 volts peak the peak voltage applied across the hinge post insulator 184, the standoff insulator 186, the insulating washer 187, and the insulating spacer 188 is very small being only 71.70 volts peak. This is less than the normal steady state rms voltage of 120 volts applied to typical household lamp cords. By comparison, the typical insulation level for traditional voltage transformers is either 95 kV or 110 kV BIL. This allows for a reduction in the cost of the STR unit 1 compared to other voltage measuring units, because the electrical insulation is negligible compared to traditional voltage transformers in use today.

Figure 26:
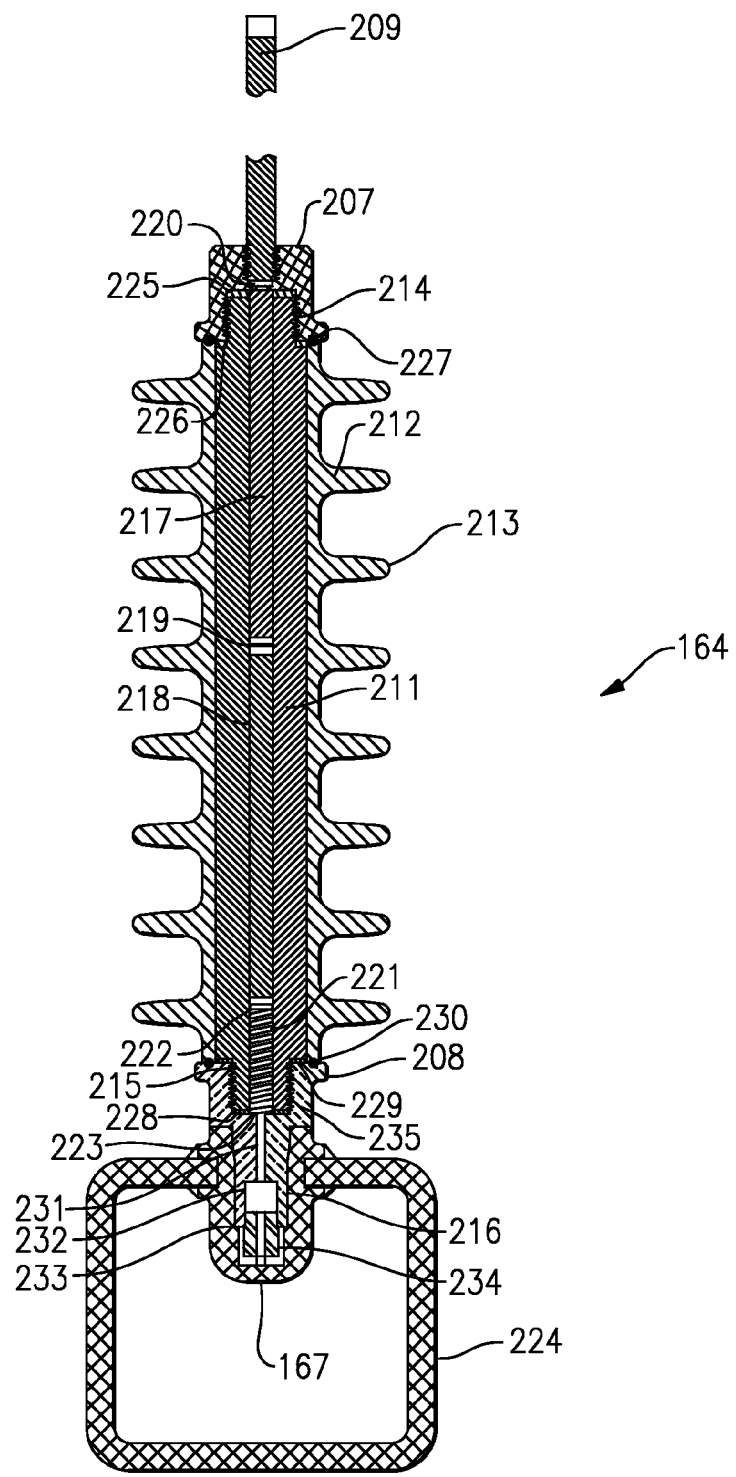
FIG. 26 illustrates a cross-sectional view of the surge block of FIG. 24 taken along line H-H.

As shown in FIG. 17, the electrically conductive jumper 165 includes the hot line clamp 205 and the hot line clamp 206 attached to each end. The hot line clamp 205 is mechanically tightened onto the stirrup 197 of the STR unit 1 and the hot line clamp 206 is mechanically tightened onto the bottom end cover 167 at the base of the surge block 164. At the top of the surge block 164 is an electrically conductive top end cap 207 which is threaded on an electrically insulated tube 211 of the surge block 164 as shown in FIG. 26. At the bottom of this electrically insulated tube 211 is an electrically conductive bottom end cap 208 which is also threaded onto the electrically insulated tube 211 of the surge block 164. An electrically conductive connector 209 is screwed into the top of the top end cap 207 and is inserted into a hole in the hot line clamp 210 of FIG. 17. The hot line clamp 210 is fastened to the phase B conductor 179.

The hot line clamps 205, 206, and 210 are commercially available parts which are used to make electrical connections to energized conductors using an electrically insulated hotstick that has a hook on the end of which a lineman places through the hole in the ring of the lead screw of the clamps and securely attaches the clamp to live parts of the stirrup assembly 11, to the bottom end cover of 167, and to the phase B conductor 179 by turning the lead screw clockwise.

Figure 24:
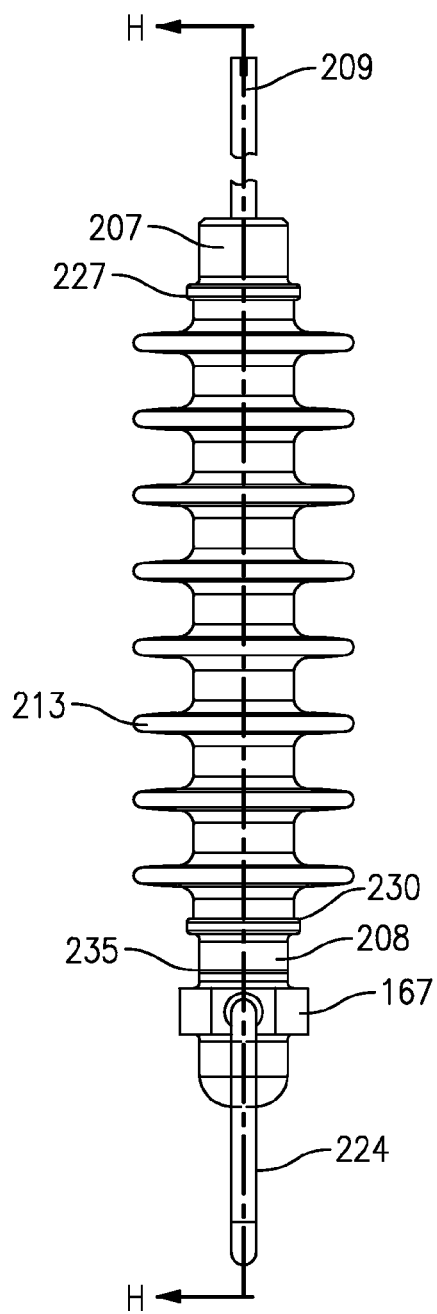
FIG. 24 illustrates a side view of a surge block.

As shown in FIGS. 24 and 26, the surge block 164 includes the electrically insulated tube 211 which possesses a high mechanical tensile strength. On the surface of the electrically insulated tube 211, there is a long molded electrical insulator 212 which has a number of skirts 213 (in this example there are 8) which increases the outside leakage distance from the electrically conductive top end cap 207 to the electrically conductive bottom end cap 208. The long leakage distance due to the shape of the skirts 213 prevents an electrical flashover from the phase B conductor 179 along the outside surface of the skirts 213 to the bottom end cap 208. The leakage distance must become greater as the voltage between the phase B conductor 179 and the phase A conductor C becomes higher.

As shown in FIG. 18 the example single phase delta connected system voltage across the surge block 164 is 5276.559 volts when the operating voltage of 5280 volts is 10 percent higher than the normal voltage of 4800 volts. The electrically insulated tube 211 has external threads 214 and 215 on each end which allows the top end cap's internal threads to be screwed onto the top of the electrically insulated tube 211 and the bottom end cap's internal threads to be screwed onto the bottom of the electrically insulated tube 211. The bottom end cap 208 has at the bottom a set of external threads 216 onto which the bottom end cover 167 is screwed, as shown in FIG. 26.

Inside the electrically insulated tube 211 are installed proprietary voltage dropping elements (VDE) 217 and 218 (in this example two VDEs are shown) which connect at an electrical contact 219 near the center of the electrically insulated tube 211 as shown in FIG. 26. The top end of the VDE 217 is electrically connected with the top end cap 207 at an electrical contact 220 and the bottom of the VDE 218 is electrically connected with the top of an electrically conductive spring 221 at an electrical contact 222. The bottom end of the electrically conductive spring 221 is electrically connected with the bottom end cap 208 at an electrical contact 223. The purpose of the electrically conductive spring 221 is to maintain a constant pressure on the VDEs 217 and 218 and provide excellent conductivity between all the electrical contacts 219, 220, 222 and 223. The bottom end cover 167, containing internal threads, is screwed on the external threads at the bottom of the bottom end cap 208.

Because an electrically conductive stirrup 224 of the bottom end cover 167 is welded to the bottom end cover 167, there is an internal continuous electrical path from the stirrup 224 through the bottom end cover 167, the bottom end cap 208, the electrically conductive spring 221, the electrical contact 222, the VDE 218, the electrical contact 219, the VDE 217, the electrical contact 220, and the electrically conductive top end cap 207 to the connector 209. The purpose of the VDEs 217 and 218 of the surge block 164 is to provide the majority of the very accurate voltage drop from the virtual ground 162 of the phase A conductor C to the phase B conductor 179, so that a very accurate voltage drop measurement of 3.441 volts is made across the $R_1$ resistor of the measuring resistor 163 shown in FIG. 18. The VDEs 217 and 218, to a major extent and to a very minor extent the measuring resistor 163 control the current flow $I_o$ of FIG. 18 to a very low rms value of only 0.52766 milliamperes during normal steady state voltage operation of 10 percent over the nominal voltage of 4800V, then the voltage drop across the jumper 165 $\Delta V_{lead}$ is nearly zero. (See FIG. 18). Even during abnormal operating conditions of +110,000 volts being applied to phase A, the peak $I_O$ current is only 0.010993 amperes as shown in FIG. 19.

Figure 25:
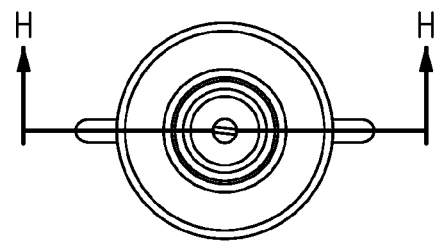
FIG. 25 illustrates a top view of the surge block of FIG. 24.

As shown in FIGS. 24, 25, and 26, it should be noted that the VDEs 217 and 218 are sealed off from being exposed to any high moisture external environments. The reason for this is to prevent any moisture accumulation appearing inside the electrically insulated tube 211 and causing a small leakage current to flow from the top end cap 207 along the internal bore between the outside wall of the VDEs 217 and 218, the inside bore of the electrically insulated tube 211, and to the bottom end cap 208 and the bottom end cover 167.

To prevent this from occurring, a triple seal has been instituted in the design of the surge block 164. First at the top and inside of the electrically conductive top end cap 207 there is a flat washer 225 which is compressed between the end of the electrically insulated tube 211 and the inside of the electrically conductive top end cap 207 by screwing the electrically conductive top end cap 207 tightly onto the threads 214. Second, there is another flat washer 226 which fits over the base of the threads 214 and is crushed by again screwing down the electrically conductive top end cap 207. Third, there is an "O" ring 227 which fits into a groove at the base of the electrically conductive top end cap 207 and prevents moisture from entering between the base of the electrically conductive top end cap 207 and the top of the long molded electrical insulator 212.

The same triple seal is applied at the bottom end cap 208. There is a flat washer 228, a flat washer 229, and an "O" ring 230 that are installed in a similar fashion to prevent moisture egress from the bottom. Now, there is a small hole 231 drilled through the center of the bottom end cap 208, of which one end of this hole leads into the inner bore of the electrically insulated tube 211 at the base of the electrically conductive spring 221 and the other end of the small hole 231 leads into a small chamber 232. At the bottom of the small chamber 232 are internal threads of which a Schraeder valve 233 is threaded into. The Schraeder valve 233 is similar to a tire tube valve which has a threaded cap 234. The purpose of the small hole 231 and the Schraeder valve 233 is to allow a vacuum pump to be attached to the threads of the valve during assembly and to vacuum air out of the inner bore of the electrically insulated tube 211 containing the VDEs. Once the air is removed, typically nitrogen gas or other suitable gas may be introduced into this inner bore and the cap 234 is installed. In addition, to prevent any leakage of the nitrogen gas or other suitable gas through the valve seat of the Schraeder valve 233 and through the cap 234, especially during very cold weather, a flat washer 235 is placed between the bottom end cap 208 and the bottom end cover 167; and the threads 216 are sealed followed by screwing the bottom end cover 167 on the threads 216 and crushing the flat washer 228 between the bottom end cover 167 and the bottom end cap 208. The other purpose of the bottom end cover 167 is to protect the Schraeder valve 233 from becoming damaged when the hot line clamp 206 of FIG. 17 is being installed by a lineman using a hotstick on the stirrup 224. It should be noted that the lightning arresters 177 shown in FIG. 17, although are not mandatory, are highly recommended to provide a higher safety margin to prevent failure during high magnitude lightning strokes.

Figure 27:
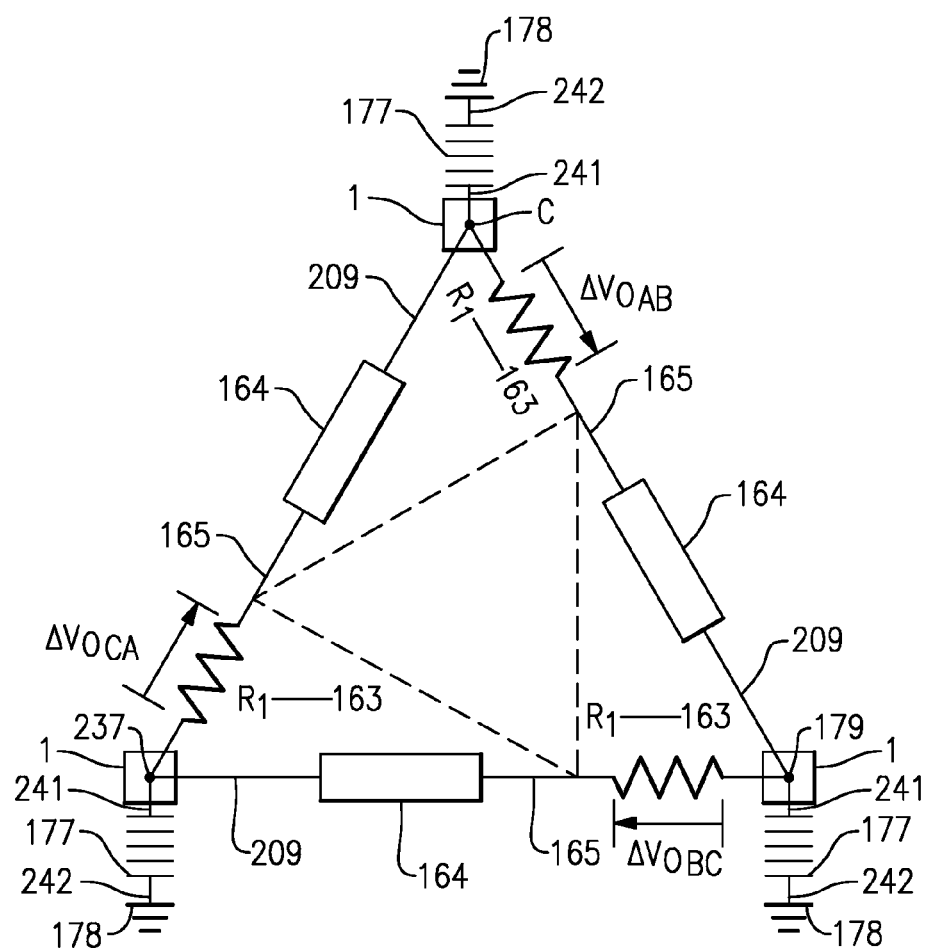
FIG. 27 illustrates a three phase delta connected ungrounded power system, with ABC phase rotation.

FIG. 27 illustrates a diagram with three STR units 1 used to measure all three phase to phase voltages of a three phase ungrounded delta connected power system. The virtual ground 161, the measuring resistor 163, the surge block 164 and the jumper 165 can be used with a three phase delta connected power system schematic as shown in FIG. 27. In a delta connected electric power system, it is necessary to monitor two of the phase to phase voltages, two line currents and the phase angles between these phasor voltages and phasor currents to determine the three phase real power.

Figure 28:
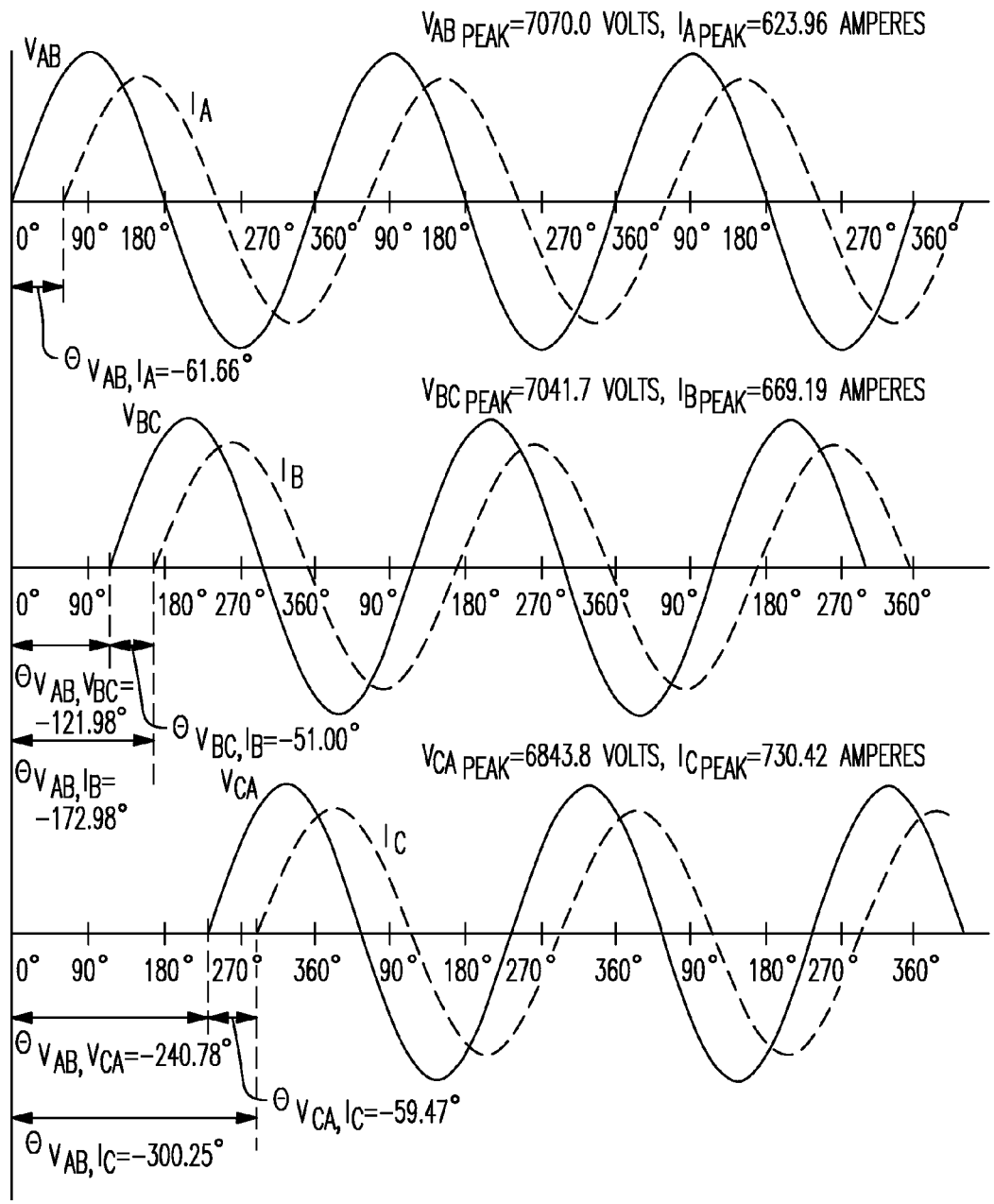
FIG. 28 illustrates phase to phase voltages ($V_{AB}$, $V_{BC}$, and $V_{CA}$) and line current ($I_A$, $I_B$, and $I_c$) waveforms for a three wire delta connected ungrounded system with $V_{AB}$ as reference.

The delta connected system of FIG. 27 is for a phase rotation of ABC. Of course STR units 1 can also be applied to a phase rotation of ACB. This means that the voltage waveforms of each phase to phase voltage will appear in the time phase relationship as shown in FIG. 28. The phase to phase voltage $V_{AB}$ is chosen as reference with its waveform magnitude being zero at zero degrees and at time equal to zero. In the example of FIG. 28, the next phase to phase voltage $V_{BC}$ lags behind $V_{AB}$ by $-121.98°$, and the phase to phase voltage $V_{CA}$ lags behind $V_{AB}$ by $-240.78°$. For this example, the first STR unit 1 is installed on phase A conductor C, as already described in FIGS. 17 and 18 for the single phase line to line voltage measurement $V_{AB}$ and the "C" loop coil 156 (see FIG. 13) of the STR unit 1 measures the phase A line current $I_A$. The second STR unit 1 as shown in FIG. 27 is installed on the phase B conductor 179, and the jumper 165, the surge block 164, the connector 209, and the hot line clamp 210 are connected to a phase C conductor 237. The second STR unit 1 installed on phase B measures the phase to phase voltage $V_{BC}$ and its "C" loop coil 156 measures the phase B line current $I_B$. The third STR unit 1 installed on the phase C conductor 237 and its jumper 165, surge block 164, connector 209, and hot line clamp 210 is connected to phase A conductor C. The third STR unit 1 measures the phase to phase voltage $V_{CA}$ and its "C" loop coil 156 measures the phase C line current $I_C$. Using this connection arrangement, the three STR units 1 measure the voltage waveforms $V_{AB}$, $V_{BC}$, and $V_{CA}$, and their corresponding line currents $I_A$, $I_B$, and $I_c$, as shown in FIG. 28. In this example, the line currents $I_A$, $I_B$, and $I_c$ lag behind their respective phase to phase voltages $V_{AB}$, $V_{BC}$, and $V_{CA}$ which means the load is both resistive and inductive. For resistive and capacitive loads these line currents would then lead their respective phase to phase voltages. The software of sensor electronics module 63 shown in FIGS. 9 and 17 in each of the STR units 1 of FIG. 27 measures on a continuous basis the angle θ between the voltage waveform and the current waveform at their respective cross-overs on the time x-axis. This angle θ which is the angle between the measured phase to phase voltage and line current for the delta connected system is not the power factor angle θ. The power factor angle θ in a delta connected system is the angle between the phase to phase voltage and its phase current. The values of θ, for the example in FIG. 28, are −61.66° for the angle between the phase A to phase B voltage $V_{AB}$ and the line current $I_A$, −51.00° for the angle between $V_{BC}$ and $I_B$, and −59.47° for the angle between $V_{CA}$ and $I_c$.

The example of FIG. 28 and the corresponding connection diagram of FIG. 27 use three STR units 1 to measure the three phase to phase voltages and the three line currents. But, as stated earlier, only two phase to phase voltages and two line currents are used to measure three phase real power in a delta connected system.

FIGS. 18 and 27 illustrate diagrammatically how the STR units 1 are connected to measure single phase line to line voltages in a delta connected system and measure all three phase to phase voltages in a three phase delta connected system. An example installation for overhead electric power lines is shown in FIG. 29 for the single phase delta connected system and FIGS. 30 and 31 for a three phase delta connected system.

Figure 29:
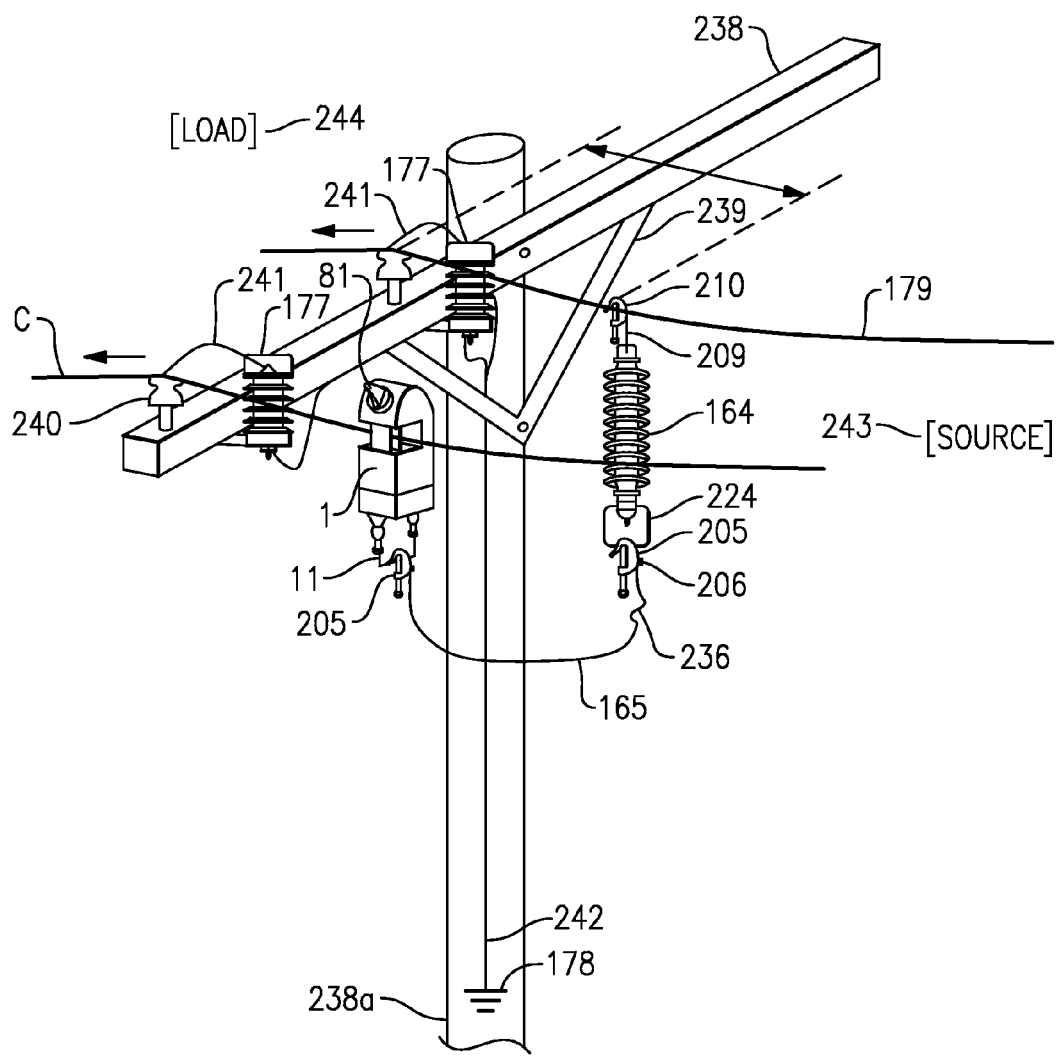
FIG. 29 illustrates single phase delta ungrounded system with the surge block and STR unit connected to phase A and phase B.

Referring to FIG. 29, the typical overhead electric power line consists of wooden poles 238a, x-arms 238, braces 239, spaced part insulators 240 mounted on top of the x-arms 238, and for the single phase case phase A conductor C, and the phase B conductor 179 are attached to the top of the spaced apart insulators 240. For lightning protection, arresters 177 may be placed various distances apart along and connected to the conductor C and the phase B conductor 179 with arrester lead wires 241 and arrester ground leads 242 trained down and attached to the pole 238a. The arrester ground leads 242 are connected to the earth ground 178 at the base of the pole 238a using a ground rod. Lightning arresters 177 are also used to protect equipment such as distribution transformers connected to the conductors C and 179. In one example, the arresters 177 are recommended to be used as shown in FIG. 29 where the STR units 1 are to be installed to increase the margin of safety. In this example, the distance between the surge block 164 connection to hot line clamp 210 is approximately two feet from the top lead 241 of the arrester 177. This short distance reduces the exposure to high inductive voltages created by high magnitude lightning strokes. Also, note that an inline fuse and holder 236 which physically holds the jumper 165 to the hot line clamp 206 isolates the jumper 165 from the surge block 164, if the voltage dropping elements (VDEs) 217 and 218 should fail and short out the surge block 164. Although this condition is highly unlikely, such a failure would cause a phase to phase fault between phases A, or conductor C and B or conductor 179.

Figure 30:
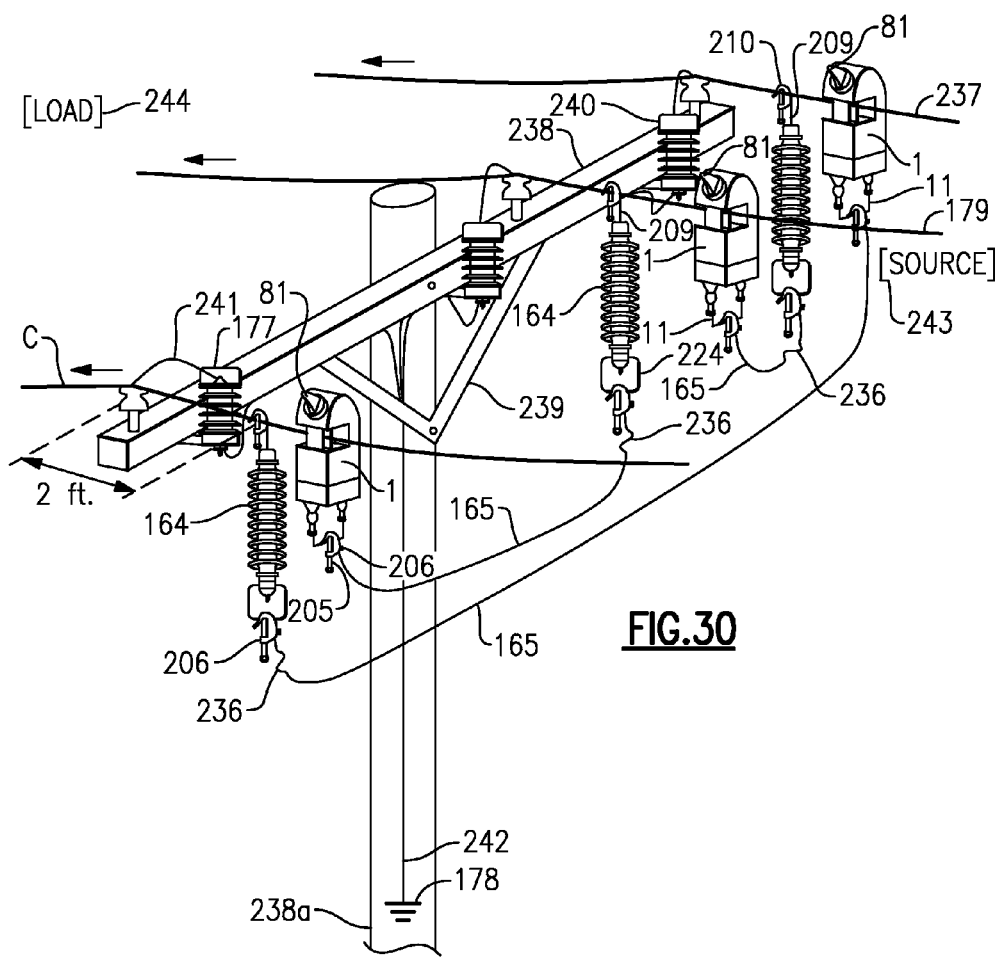
FIG. 30 illustrates a three phase delta ungrounded system with surge block and STR units attached to each phase.
Figure 31:
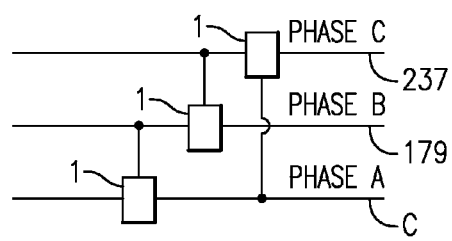
FIG. 31 is a schematic top view of FIG. 30.

FIGS. 30 and 31 illustrate the example three phase installation of STR units 1 for the delta connected system, which was shown diagrammatically in FIG. 27. The single phase delta installation shown in FIG. 29 and the three phase installation of FIGS. 30 and 31 have the SOURCE 243 of power designation located on the right side of FIGS. 29-31 and the phase currents flowing from right to left to the LOAD 244. It is very important to mount the STR units 1 with the right side as shown in FIG. 1 facing toward the SOURCE 243 of power. This insures the correct polarity for the 60 or 50 Hz current and lightning stroke current measurements made by the "C" loop coils 156 and 157, respectively. FIG. 1 has a louvered vent 65 located above the conductor C, which is white and indicates the polarity mark on the STR unit 1. It is common practice in the industry to mark all current transformers with such a white polarity mark to insure the SOURCE 243 of power is directed toward the polarity mark which will result in the correct output polarity and the correct calculation of power.

Figure 32:
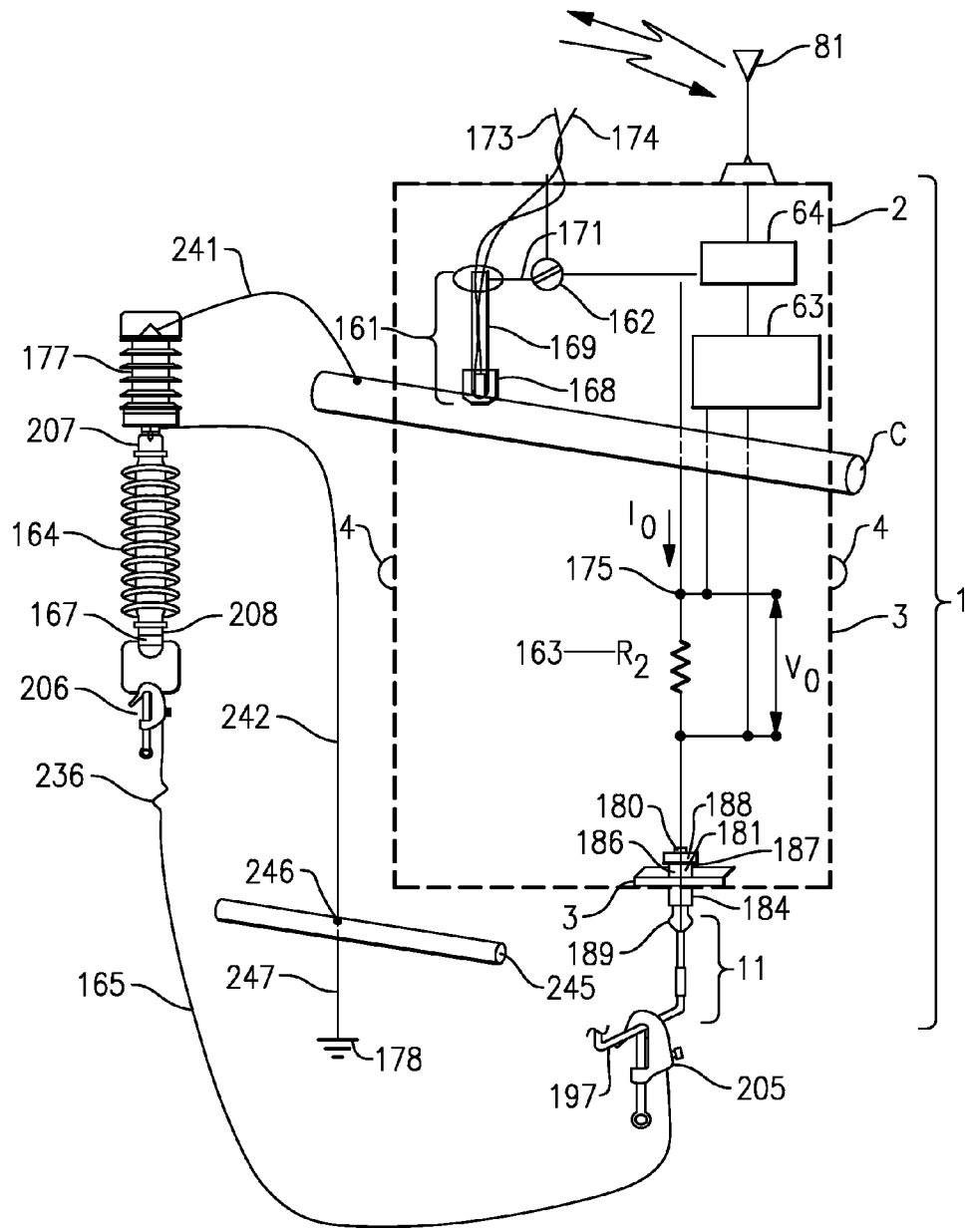
FIG. 32 is a schematic view of a single phase line to neutral voltage sensing circuit for a multi-grounded wye connected power system where the surge block is integrated with the lightning arrester.

The virtual grounding device 161, the measuring resistor 163, the surge block 164 and the jumper 165 used for measuring phase to phase voltages of the delta connected system will be used for measuring phase to neutral voltages for a wye multi-grounded connected system. The cut-away view of the STR unit 1 shown in FIG. 16 illustrates that the delta connected system applications remains the same for the wye multi-grounded connected system. Referring to FIGS. 16 and 32 the virtual grounding device 161 the measuring resistor 163, the surge block 164, and the jumper 165 include clamps at each end. The measuring resistor 163 resistance will change from $R_1$ to a different value $R_3$ when measuring a much higher line to neutral voltage. Although for this example, shown in the diagram of FIG. 33, the surge block resistance value 176 will remain the same as for the delta system example, it may change to a different value of $R_4$ for much higher voltage systems. However, the mechanical parts of the four essential components remain the same for measuring phase to phase or phase to neutral voltages from 4 kV up to 60 kV for electric power distribution system applications. Only the resistance values for the measuring resistor 163 and the surge block resistance value 176 may change.

Figure 33:
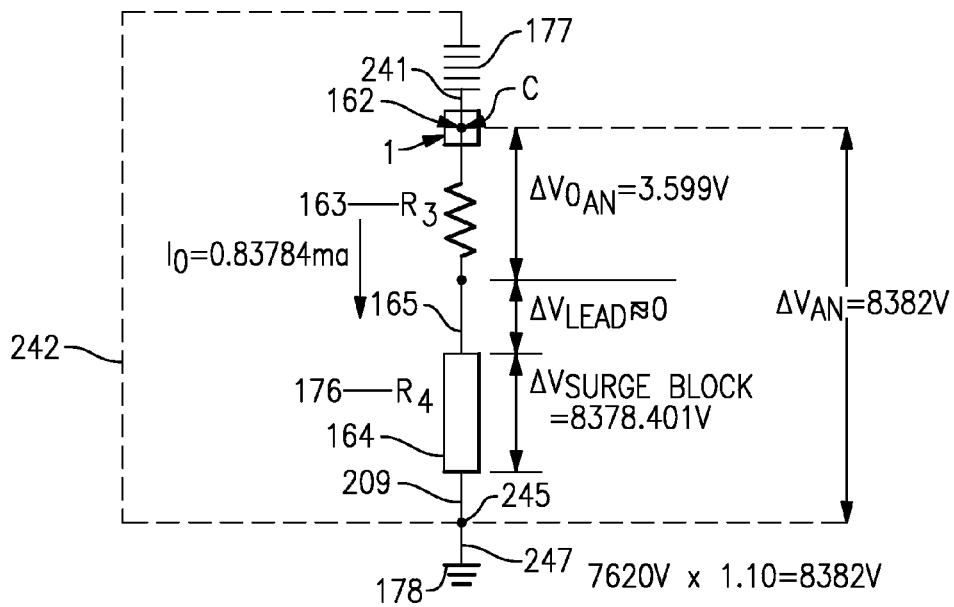
FIG. 33 illustrates a schematic view of a single phase line to line voltage, phase A to neutral multi-grounded wye connected power system.

For the multi-grounded wye connection of the single phase case shown in FIGS. 32 and 33 the only difference between the multi-grounded wye connection and the delta is the surge block 164 is connected to the neutral conductor 245 by either screwing the top of surge block 164 directly into the standard threaded stud at the base of the arrester 177 and avoiding the use of the hot line clamp 210 and connector 209 shown in FIG. 17, or using the connector 209 and hot line clamp 210 to connect to the neutral conductor 245. The top of the surge block 164 in the former case is now electrically routed via the arrester ground lead 242 to a connection point 246 of the neutral conductor 245. The arrester ground lead 242 then continues on to the earth ground 178 via a lead wire 247.

Figure 34:
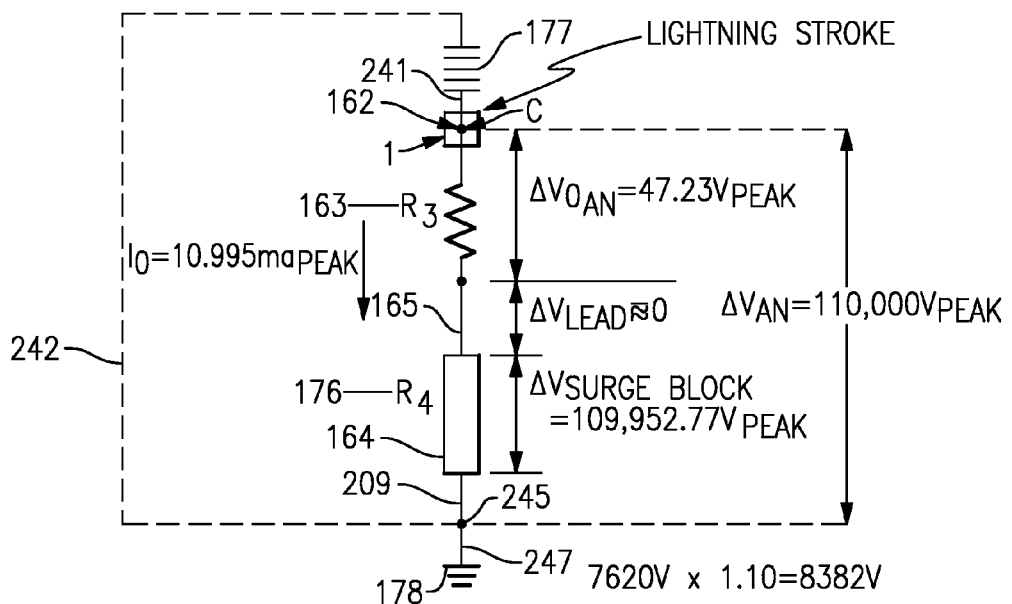
FIG. 34 illustrates a schematic view of a single phase line to neutral, phase A to neutral multi-grounded wye connected power system with lightning stroke of +110,000 volts peak applied to phase A.

The example given for the multi-grounded wye single phase line to neutral case is for the most commonly used distribution system voltage of 13.2 kV line to line or 7.620 kV line to neutral. For the normal operating measuring condition, the line to neutral voltage becomes 8382 volts, when the nominal value of 7.620 kV is increased 10 percent to account for regulated voltages above the nominal value. For this value of voltage the rms current $I_o$ of FIG. 33 flowing through the $R_3$ measuring resistor 163 is 0.83784 milliamperes which produces an rms output voltage $V_{OAN}$ equal to 3.599 volts when 8382 volts, or $V_{AN}$ is impressed across the phase A conductor C to the neutral conductor 245, and the connection point 246 of FIG. 32. The voltage drop across the surge block 164 is 8378.401 volts rms of which the sum of this drop and the measured voltage of 3.599 is equal to 8382 volts rms. This measured voltage drop of 3.599 volts is directly proportional to the phase A to neutral voltage of 8382 volts and there is no phase shift in this measured value. For the abnormal condition of a lightning stroke of +110 kV applied to the phase A conductor C, as shown in FIG. 34, the $I_O$ current peak value is 10.995 milliamperes and a peak voltage output $V_{OAN}$ of only 47.23 volts occurs. Here again lightning arresters, although not required, are recommended to provide an additional margin of safety over the 113 kV BIL of the surge block 164, which increase the margin 213 percent for a lightning stroke of +110 kV.

Figure 35:
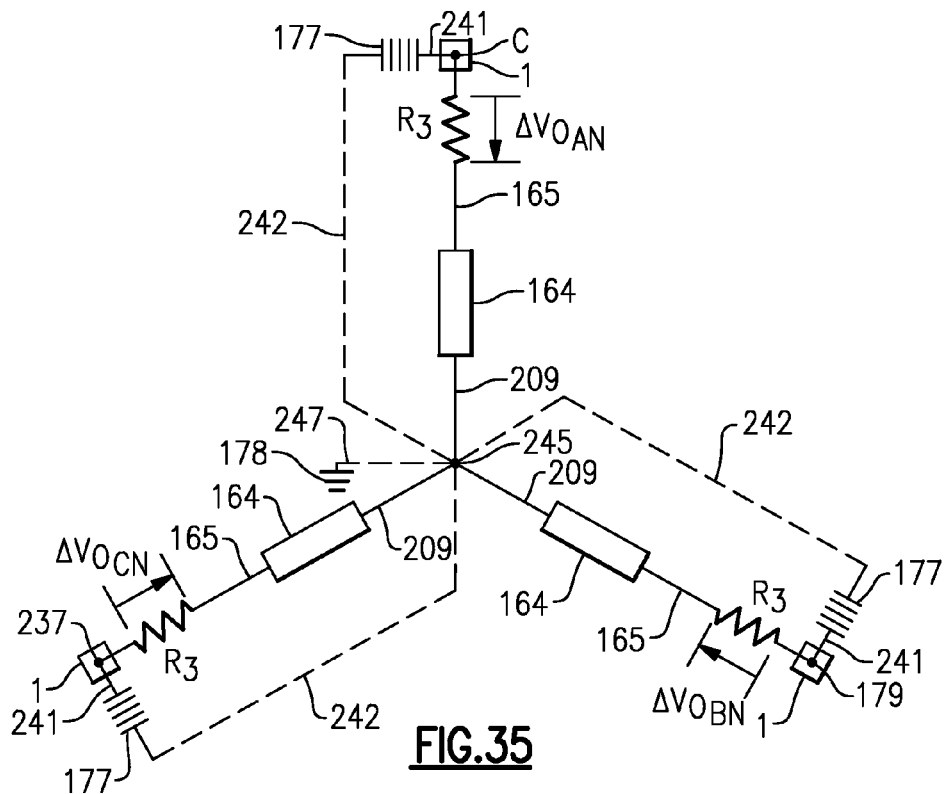
FIG. 35 illustrates a schematic view of a three phase multi-grounded wye connected power system, with ABC phase rotation.

The three phase multi-grounded wye system is shown diagrammatically in FIG. 35 with phase rotation ABC. Here the first STR unit 1 is installed on phase A conductor C with the top end of its surge block 164 connected to the neutral conductor 245. Similarly, the second STR unit 1 is installed on the phase B conductor 179, with the top end of its surge block 164 connected to the neutral conductor 245, and the third STR unit 1 is installed on phase C conductor 237 with the top of its surge block 164 connected to the neutral conductor 245. Although optional, each of the lightning arresters 177 are connected to the phase conductors C, 179, and 237 using the lead wires 241 and the arrester ground leads 242 which are each connected to the neutral conductor 245 and then to the earth ground 178 using the lead wire 247. Each of the three phase multi-grounded system phase to neutral voltages are measured using the three STR units 1.

For an ungrounded wye connected system the lead wire 247 is not used at all to connect to the earth ground 178, thus isolating the neutral conductor 245 from the earth ground 178. The lightning arrester ground leads 242 by-pass the neutral conductor 245 and go directly to the earth ground 178. Each of the three STR units 1 are just connected phase to the neutral conductor 245 and are not connected to the earth ground 178.

Figure 36:
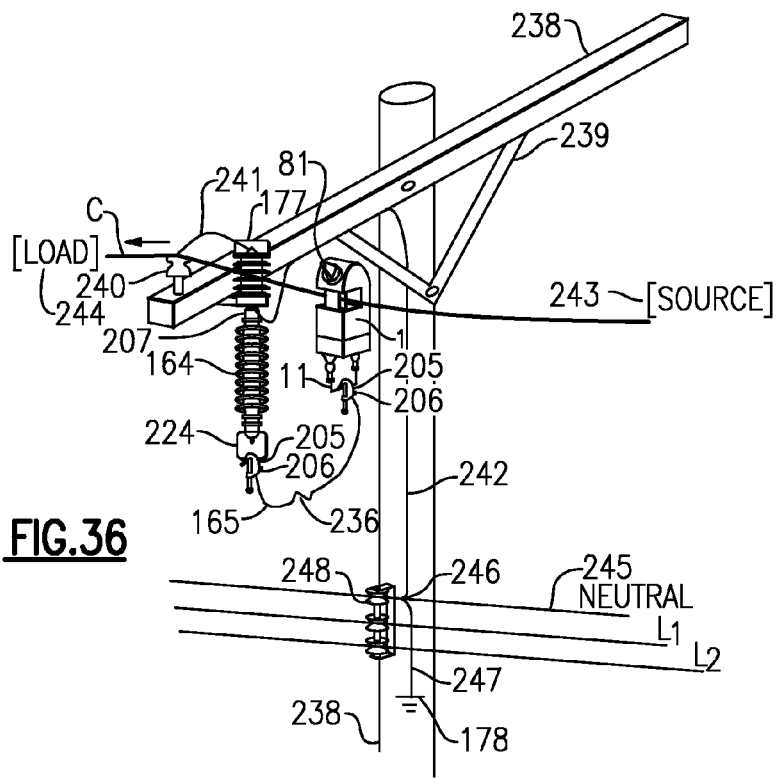
FIG. 36 illustrates a single phase multi-grounded wye connected system with secondary, and integrated lightning arrestor and surge block installed on phase A where the arrester ground is connected to surge block, neutral, and then earth ground.

Five different physical installations are shown in FIGS. 36 through 40 for the multi-grounded wye connected system. FIG. 36 illustrates a single phase multi-ground wye connected system with the neutral conductor 245 located lower on the pole 238*a* at the secondary level. The neutral conductor 245 is installed on one insulator spool 248 of the three spool rack is not only the system neutral, but the neutral for the 120 volt secondary voltages $L_1$ and $L_2$. The installation of FIG. 36 represents the case where the surge block 164 is integrated with the lightning arrester 177. The surge block top end cap 207 is screwed onto the standard threaded ground stud at the bottom of the arresters 177. This eliminates the need for the connector 209 shown in FIG. 39, which will be discussed later. The STR unit 1 measures the line current $I_A$ in phase A conductor C with "C" loop coil 156 and measures the phase A conductor C to neutral voltage $\Delta V_{OAN}$ as seen in the diagram of FIG. 33. Again, the right side of the STR unit 1 faces the SOURCE 243.

Figure 37:
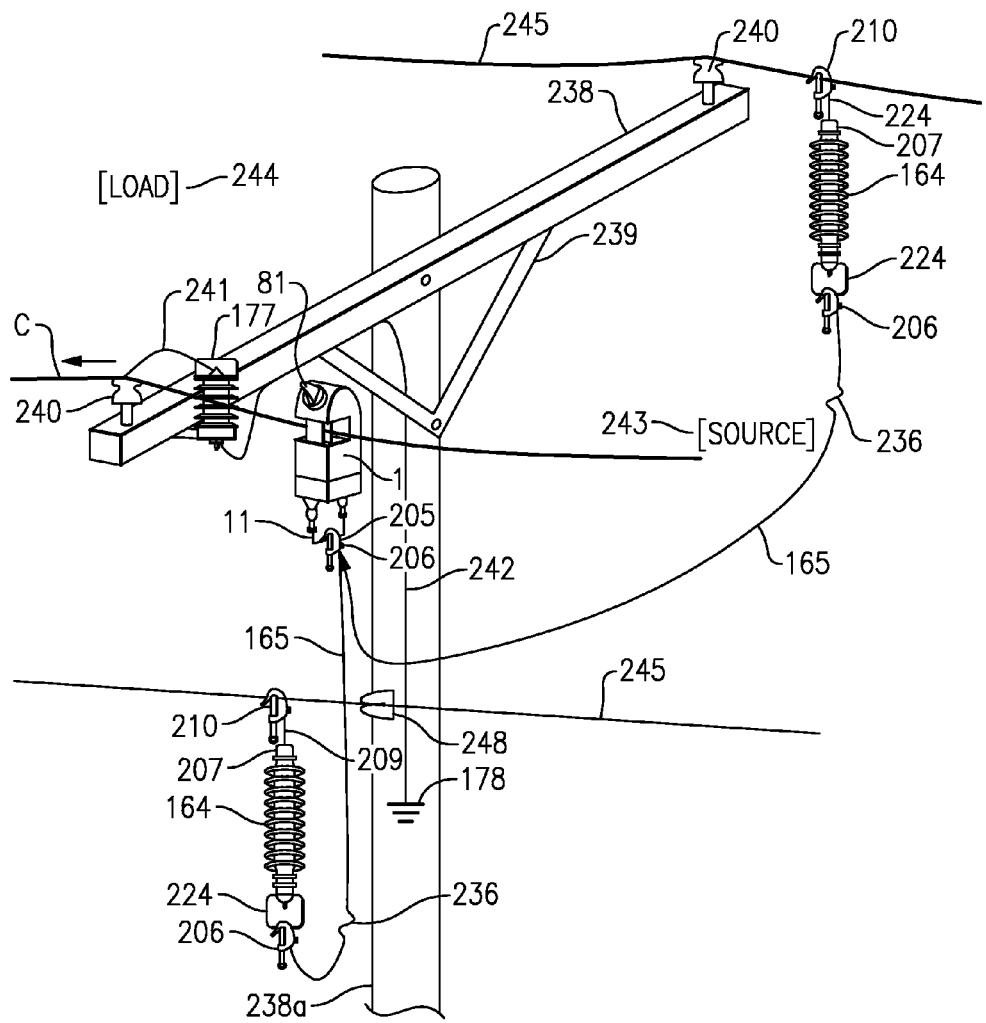
FIG. 37 illustrates a single phase ungrounded wye connected system with lightning arrester on one phase and surge block connected to an ungrounded neutral conductor on x-arm insulator or surge block connected to ungrounded neutral at secondary level.

FIG. 37 is an example of a single phase ungrounded wye connected system where the phase A lightning arrester ground lead 242 is routed directly to the earth ground 178 and does not connect to the neutral conductor 245 which is isolated from the earth ground 178. In this case the bottom of the connector 209 is screwed into the top of the surge block's top end cap 207 and the top of 209 is connected to the hot line clamp 210.

It should be noted that two different installation methods are shown for the single phase ungrounded wye system of FIG. 37 as to how the surge block 164 is connected to the ungrounded neutral. One method is where the surge block hot line clamp 210 is connected to the neutral conductor 245 which is located on the spaced apart insulator 240 of the x-arm 238. Since the neutral conductor 245 is located on the x-arm 238 like the phase A conductor C is located on the x-arm 238, then it has in most instances the same equal chance as the Phase A conductor C of being struck by lightning. Therefore, when the neutral conductor 245 is in this position it is recommended that a lightning arrester 177 be installed near the neutral conductor on the x-arm 238 with the lead wire 241 connected to the neutral conductor 245 and arrester ground leads 242 which in turn is directly connected to the earth ground 178.

Another example voltage measuring device is shown in FIG. 37. The hot line clamp 210 of the surge block 164 is connected to the neutral conductor 245 which is mounted down below the x-arm 238 on the insulator spool 248 attached to the pole 238*a* at the secondary level. Notice the arrester ground lead 242 is not connected to the neutral conductor 245, but instead is directly connected to the earth ground 178. Also note in this case, the lightning arrester 177 is not mounted on the pole 238*a* with the arrester lead wires 241 connected to the neutral conductor 245. However, this does not mean that a lightning arrester 177 cannot be installed on the pole 238*a* at the secondary level near the neutral conductor 245 and have the arrester lead wires 241 connected to the neutral conductor 245 and the arrester ground lead 242 connected to the earth ground 178. But, mounting the neutral conductor 245 at the secondary level on the insulator spool 248 places it below the phase conductors C and 179 on the x-arm 238 and as such the phase conductors partially shield the neutral conductor 245 from lightning strokes.

Figure 38:
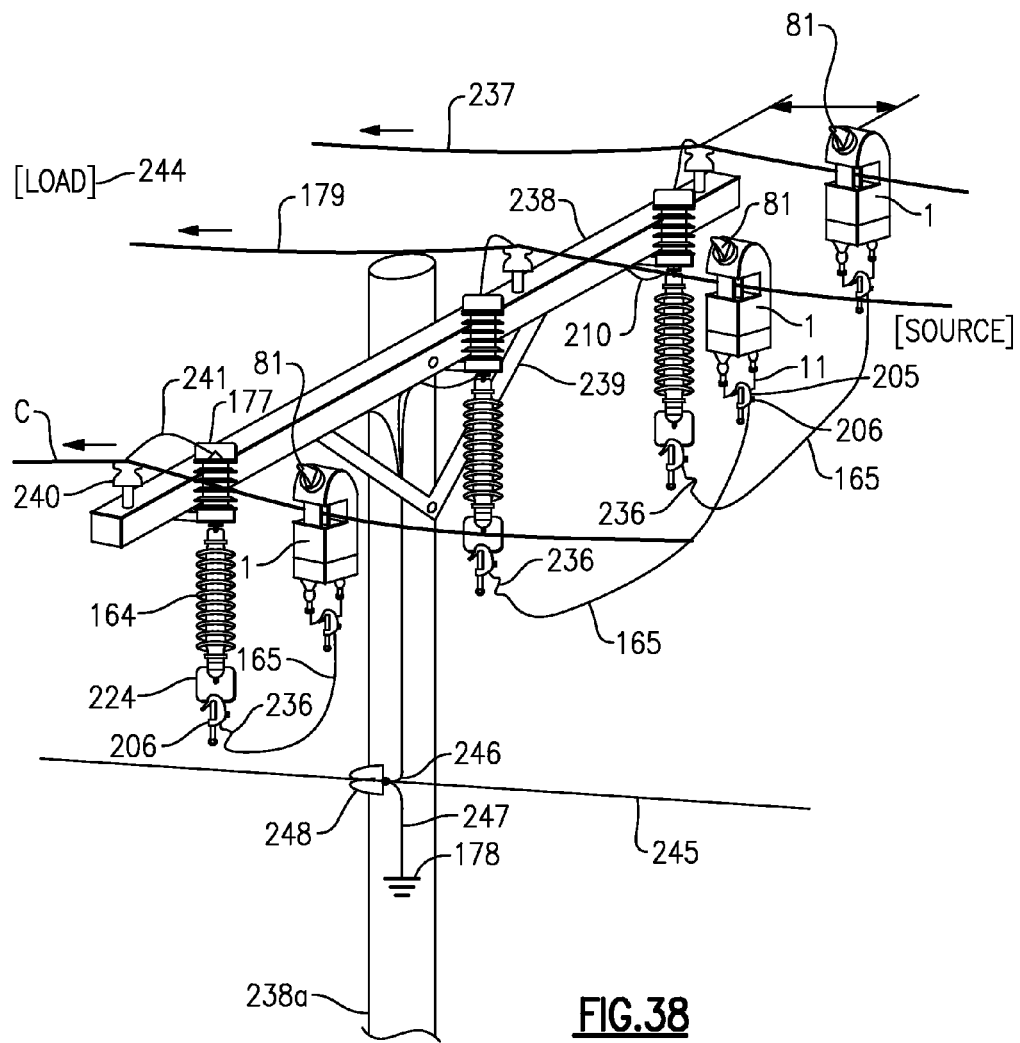
FIG. 38 illustrates a three phase multi-grounded wye system with an integrated lightning arrester and surge block installed on each phase where the arrester ground is connected to surge block, neutral, and then earth ground.

FIG. 38 illustrates a three phase multi-grounded wye installation employing the integrated lightning arrester 177 and the surge block method of screwing the top end cap 207 of the surge block 164 into the threaded ground stud at the base of the standard lightning arrester 177. Since the arrester ground lead 242 is connected to the neutral conductor 245 at the connection point 246, the need for the connector 209 and the hot line clamp 210 is eliminated.

As shown in the diagram of FIG. 35, one STR unit 1 is installed on phase A or conductor C and measures the phase A to neutral voltage $\Delta V_{OAN}$, and its "C" loop coil 156 measures the phase current $I_A$. A second STR unit 1 is installed on phase B or conductor 179 and measures the phase B to neutral voltage $\Delta V_{OBN}$ and its "C" loop coil 156 measures the phase current $I_B$. A third Unit 1 is installed on phase C or conductor 237 and measures the phase C to neutral voltage $\Delta V_{OCN}$ and its "C" loop coil 156 measures the phase current $I_c$.

From these voltage and current measurements of each of the three STR units 1 waveforms, then the power factor angle θ between each phase to neutral voltage and its corresponding phase current can be found in the same manner as described in FIG. 28 for the delta connected system. Once the rms values of voltage and current are determined for each phase and their respective power factors, then the real power, reactive power and apparent power can be found. The single phase real power for a wye connected system is simply the product of the measured rms value of the line to neutral voltage and the measured rms value of its phase current times the cosine of the measured power factor angle θ between the line to neutral voltage and its phase current. The product of the rms values of the line to neutral voltage and the phase current times the sine of the measured power factor angle determines the reactive component and the vector sum of these real and reactive components produces the apparent power. For a three phase wye connected system the three individual single phase components of real power, reactive power, or apparent power, as determined above, are added together.

Figure 39:
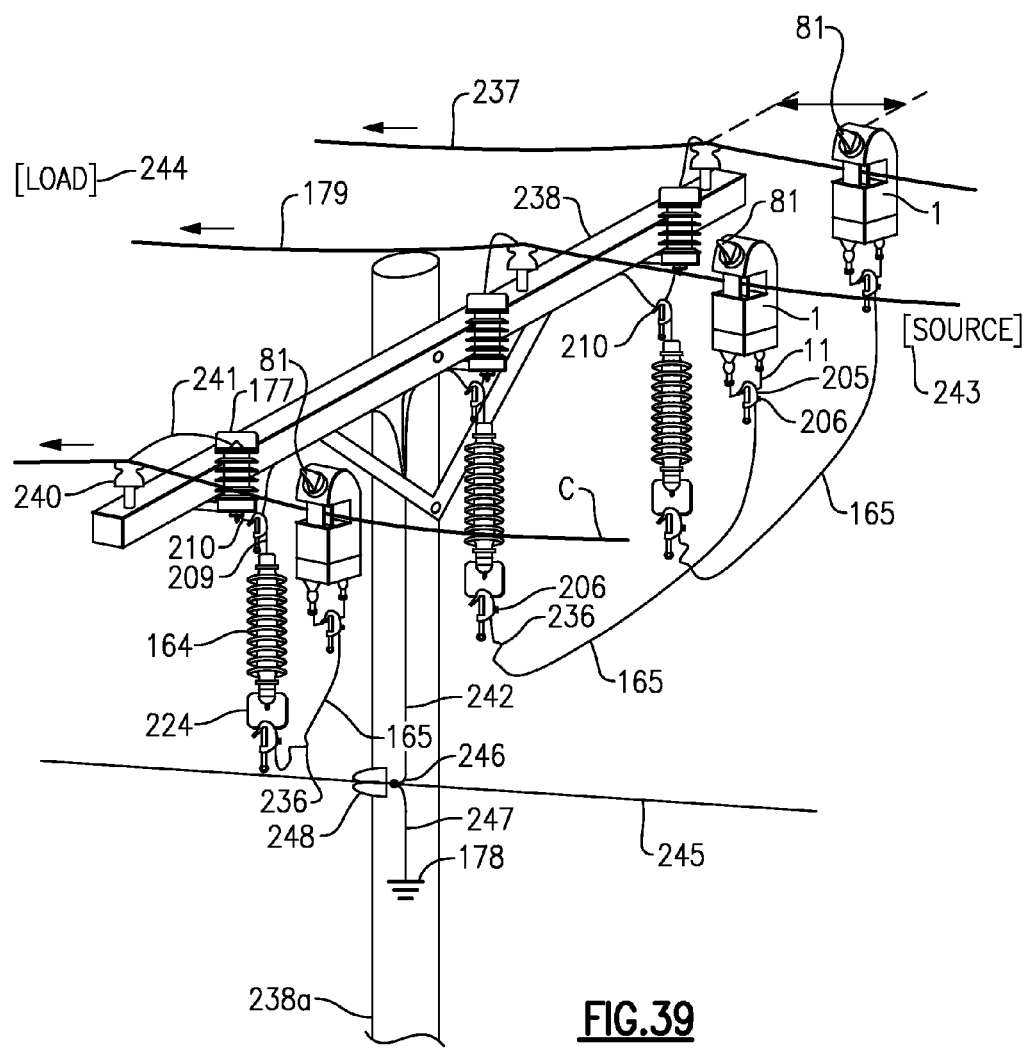
FIG. 39 illustrates a three phase multi-grounded wye connected system with lightning arresters on each phase and surge blocks connected to their respective arrester grounds.

A variation of the three phase multi-grounded wye connected system of FIG. 38 is shown in FIG. 39. In FIG. 39, the top end cap 207 has the connector 209 screwed into the threads in the top end cap 207 as was shown in FIGS. 17, 24, and 25, and the top of the connector 209 is installed in the hot line clamp 210 as shown in FIG. 17. An advantage of the installation is that the surge block 164 can be installed with the hot line clamp 210 on the arrester ground lead 242 with the hotstick 10, whereas with the integrated arrester and surge block method of installation, the surge block is screwed onto the arrester ground stud at the base of the arrester. Except as discussed above or shown in FIG. 39, the installation of FIG. 39 is the same as installation shown in FIG. 38.

For the methods of installation of FIGS. 36, 37, 38, and 39, it is assumed that each lightning arrester 177 already pre-exists and has been mounted on the bottom of the x-arm 238 near each of the phase conductors C, 179, and 237. Also, each lead wire 241 has been attached to each of the phase conductors C, 179, and 237 and each arrester ground lead 242 has either been attached directly to the earth ground 178 in the case of the ungrounded wye, or has been attached to the neutral conductor 245 at the connection point 246 and then to the earth ground 178 via the lead wire 247 for the multi-grounded wye connected system.

Figure 40:
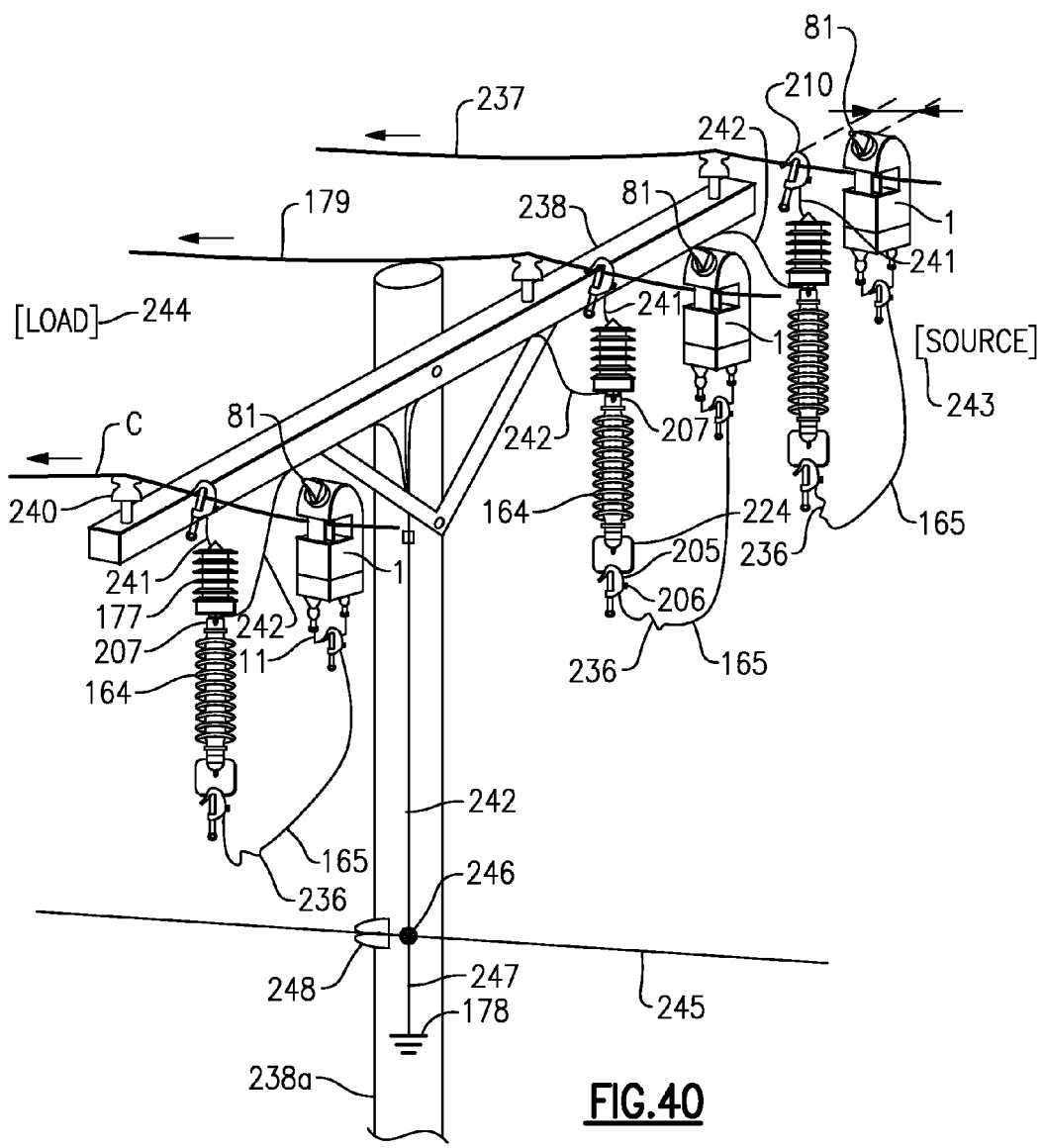
FIG. 40 illustrates three phase multi-grounded wye system with an integrated lightning arrester and surge block installed on each phase where no lightning arresters preexist.

The variation shown for the three phase multi-grounded wye system in FIG. 40 with the lightning arrester 177 does not pre-exist, but it is still an option to have an arrester 177 mounted on each phase. The integrated lightning arrester 177 and surge block 164 are pre-assembled as a unit with the arrester lead wires 241 connected to the hot line clamp 210. This assembly is installed with the hotstick 10 placed through the ring in the clamp of 210 and placed on the phase conductors C, 179, and 237 as shown in FIG. 40. Since each arrester ground lead 242 is not energized and can be pre-assembled on the pole 238a, even though the phase conductors C, 179, and 237 are energized, the arrester ground leads 242 are each attached to the ground stud at the base of each arrester 177 and then the top end cap 207 of each surge block 164 is tightened securely to their respective arrester ground lead 242. Finally, each STR unit 1 is installed on each of the phase conductors C, 179, and 237 using the hotstick 10 and the jumper 165 is first attached to the stirrup 224 using hot line clamp 206 and then to the stirrup 11 of each STR unit 1 using the hot line clamp 205. Even though there is no arrester 177 pre-existing on the x-arm 238, a three phase voltage and current measuring system can be installed without having to de-energize the phase conductors C, 179, and 237 and interrupt customer load. Of course, this same method can be used for the three phase ungrounded wye connected system, the single phase multi-grounded system of FIG. 36, and the single phase ungrounded wye connected system with no customer load interruptions.

Another approach can be implemented for the single phase delta ungrounded system of FIG. 29 and the three phase delta ungrounded system of FIG. 30. If lightning arresters 177 are not pre-existing and mounted on the bottom of the x-arm 238, the hot line clamp 210 having the arrester lead wire 241 attached at the bottom of this clamp while the arrester ground lead 242 is attached to the bottom of the arrester base threaded stud, can be installed directly on the phase conductors C, 179, and 237 using the hotstick 10 placed through the ring of the lead screw of the hot line clamp 210. This method of installing the arresters 177 can be performed without shutting down or de-energizing the phase conductors C, 179, or 237 and thus no load is interrupted.

Figure 41:
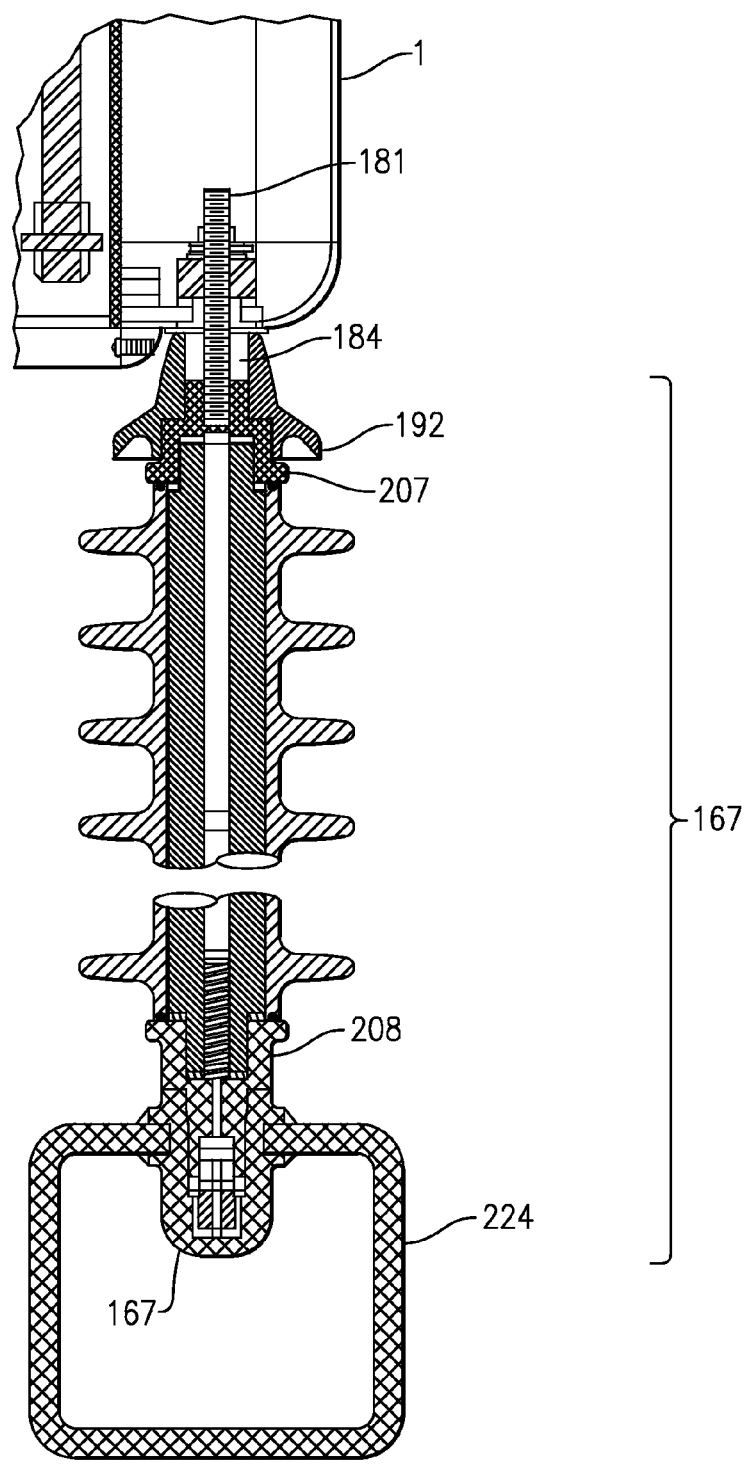
FIG. 41 illustrates a cutaway view of an integrated surge block and STR unit.

FIG. 41 illustrates the STR unit 1 mounted on the one phase conductor C, just as in FIGS. 17 and 32, but the right hinge post 189, the right side threaded sleeve 194, and the jumper 165 have been removed and the top end cap 207 of the surge block 164 has been threaded directly on the threaded hinge post stud 181. The hotline clamp 205 is attached to the stirrup post 224 of FIG. 41 and the jumper 165 including its hot line clamp 206 is directly connected to the other phase conductor 179 or the neutral conductor 245. In this method the jumper 165 still incorporates the fuse and holder 236 as shown in FIGS. 17 and 32. An advantage of this integrated surge block and STR unit 1 is the elimination of four parts, the electrically conductive right hinge post 189, right side threaded sleeve 194, the electrically conductive connector 209, and the hot line clamp 210, as shown in FIGS. 17 and 20.

When the stirrup assembly 11 is not used and the methods shown in FIGS. 21 and 23 are used which only have one weather shed 192, then the STR unit 1 may not hang vertical on the phase conductor C. This introduces error in the solar radiation measurement and the line sag measurement because the STR unit 1 should remain vertical to insure the accuracy of the measurements. However, this method can be employed for the installation of STR units 1 on rigid bus bar indoor or outdoor conductors which remain in a fixed position. With the physical installation methods, the STR unit 1 and the surge block 164 can be installed without de-energizing any phase conductor C, 179, or 237 and interrupting load for both delta connected and wye connected systems. This is not the case for installing traditional voltage and current transformers. Traditional devices require the phase conductors C, 179, and 237 to be shut down and current transformers have to have the phase conductors C, 179, or 237 inserted through the center of the open window in the transformer, which requires the phase conductors C, 179, and 237 to be opened and then reconnected resulting in an interruption of customer load.

The disclosed method of measuring phase to phase or phase to neutral voltages of delta connected or wye connected power systems not only produces more accurate measurements, typically less than one percent measurement error and even down to 0.1 percent, but also does not introduce any measurable phase shift in the voltages to be measured. This is not the case for traditional voltage transformers which typically have measurement errors of two percent or more Eliminating phase shift in the measured voltage waveforms is very important for applications where synchrophaser measurement instruments are installed typically at substations on three phase power systems to be used as a tool to determine the maximum power flow between power system networks. This maximum power flow is a function of the angle (normally referred to as the Greek letter δ) between the sending end voltage of one power system network and the sending end voltage of another network. The larger the angle δ, the greater the power flow.

Figure 42:
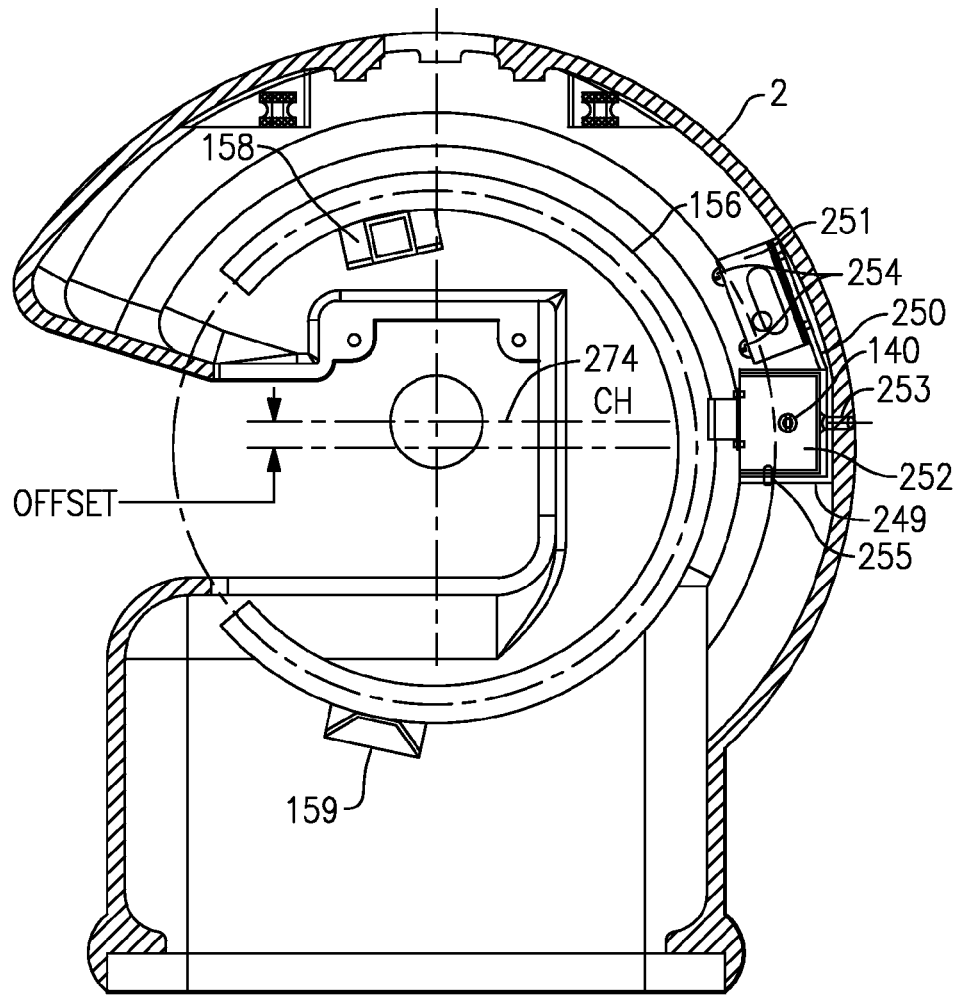
FIG. 42 illustrates a section view E-E of upper housing showing "C" loop coil, GPS and sag sensor.
Figure 43:
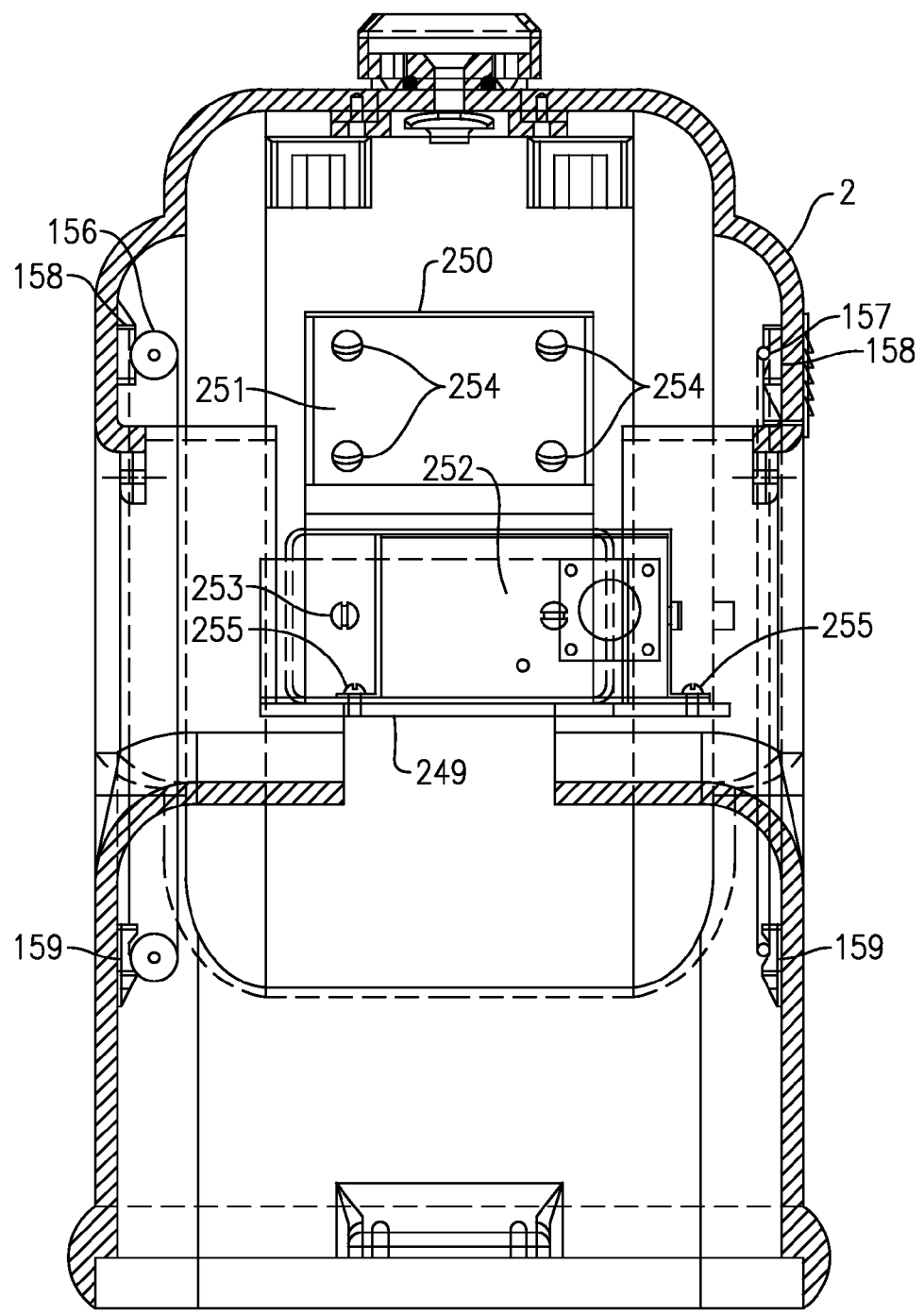
FIG. 43 illustrates a section view F-F of upper housing showing "C" loop coils for line current and lightning stroke current.

Each of the STR units 1 have on board a very accurate time clock that measures time with an accuracy of $1 \times 10^{-9}$ seconds and global position system (GPS) 251 so that the STR units 1 can be installed at different locations on various power system networks and the angle δ can be found between the measured reference voltage waveforms in one system and those measured reference waveforms in another system, all in real time. Since the measured voltage waveforms are time synchronized with an accuracy of $1 \times 10^{-9}$ seconds then very accurate values of the angle δ can be found. The GPS and time clock 251 are shown in FIGS. 42 and 43. An "L" bracket 249 is mounted to the back wall of the upper housing 2 and an angle bracket 250 is attached to the "L" bracket 249 and then the upper housing 2 using two screws 253. The GPS and time clock 251 is mounted on the angle bracket 250 using four screws 254. The sag sensor 252 is mounted to the base of the "L" bracket 249 with two screws 255.

Also, this new voltage measuring method can be used to measure high magnitude and high frequency lightning stroke voltages with very low energy measurement losses. Furthermore, the cost is about 7.5 percent of the cost of traditional voltage transformers for distribution system voltage levels, and the weight of this new voltage measuring apparatus is only about five pounds, or at least an order of magnitude less than the weight of traditional voltage transformers for distribution electric power systems.

Another condition associated with the high magnitude fault current is the phase angle $\theta_f$ between its phase voltage and its fault current is much greater, typically 70 to 80 degrees, than the power factor angle $\theta$ of the load current which is much less, typically 26 to 37 degrees for corresponding power factors of 0.90 (i.e. cos 26°=0.90) to 0.80 (i.e. cos 37°=0.80). This large difference between the fault phase angle $\theta_f$ and the load current phase angle $\theta$ during steady state operation in conjunction with the change to higher current magnitudes during faults are detected using the same technique as was outlined in the example of FIG. 28. The sensor electronics module 63 of FIG. 17 measures on a continuous basis this angle—between the voltage waveform and the current waveform at their respective cross-overs on the time x-axis and the magnitude of the current. But, when the software of the sensor electronics module 63 detects this abrupt change in $\theta$ and current magnitude, then either a fault or a large motor start causing similar changes in $\theta$ and the magnitude in current has occurred. In addition, the magnitude of the voltage waveform(s) are depressed for faults and motor starts which are also measured by the STR unit's 1 voltage measuring apparatus and detected by the sensor electronics module 63. This data, in addition to the fault location and fault direction, is sent by the transmitter/receiver unit 64 via the antenna 81 to a remote location where this data can be used to provide fast analysis and assessment; and fast restoration of the power system. The fault current direction is detected by the sensor electronics module 63. If the fault current changes polarity, then the fault current is in the opposite direction to the pre-fault load current. If the fault current does not change polarity, then the fault current is in the same direction as the pre-fault load current.

Since the STR units 1 measure the current and voltage wave forms on a real time basis using the "C" loop coils 156 and the voltage measuring apparatus described earlier, then the measurements can be used to calculate the power quantities of watts, vars and power factor. Also this same data can be used to calculate the percent unbalance for current and voltage. In the example of FIG. 28, the unbalance voltage of 2.031% is calculated from the measured negative sequence voltage divided by the measured positive sequence voltage knowing the magnitudes of the measured voltage phasors and the angles between them, since the positive and negative sequence voltages can be determined. Furthermore, from this example, the percent unbalance current of 9.945% is calculated from the measured negative sequence current divided by the measured positive sequence current. Again, since the voltage and current waveforms are available from this measured data, the total harmonic distortion for current and voltage can be calculated as measures of the power quality of the delivered power.

Finally, the installation methods for this new measurement apparatus can be done while the lines are energized using the specially designed hotstick 10 in considerably less time than for traditional voltage and current transformers. A three phase installation can be completed in about 20 to 30 minutes compared to 4 hours or more for normal construction times using conventional voltage and current transformers.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

What is claimed is:

1. A device for measuring a voltage of an electric power line conductor of a power system comprising:
   a first electrically conductive housing configured to be installed on a first power line conductor;
   a first virtual grounding member configured to electrically ground a first housing to a first power line conductor voltage;
   a first measuring resistor electrically connected between the first virtual grounding member and an electrically isolated lead wire, the electrically isolated lead wire electrically connected to a first voltage dropping device, the first voltage dropping device configured to be electrically connected to a second power line conductor; and
   a sensor electronics module configured to measure a voltage drop across the first measuring resistor, the voltage drop being directly proportional to the voltage between the first power line conductor and the second power line conductor.

2. The device of claim 1, including a power supply electronics module configured to provide power to the sensor electronics module, the sensor electronics module is configured to process voltage data representing a voltage drop output across the first measuring resistor and transmit the voltage data to a remote location with a transmitter and receiver unit.

3. The device of claim 2 wherein the power supply electronics module includes a magnetic core configured to surround the first power line conductor including a secondary winding configured to deliver power to the power supply electronics module.

4. The device of claim 3 wherein the magnetic core includes a first magnetic core and a second magnetic core configured to surround the first power line conductor.

5. The device of claim 1 including an electrical circuit interrupting device configured to isolate the first voltage dropping device from the first measuring resistor when the voltage dropping device fails.

6. The device of claim 1 wherein the first measuring resistor is non-inductive and non-capacitive and the first voltage dropping device includes at least one non-inductive and non-capacitive component.

7. The device of claim 1 wherein the voltage dropping device includes a surge block configured to limit current flow.

8. The device of claim 1 wherein the voltage dropping device includes electrically conductive fittings for attaching an electrically conductive jumper between the electrically isolated lead wire and the voltage dropping device.

9. The device of claim 1 including a clamp connected to a fitting on the one end of the voltage dropping device to facilitate installation on the second power line conductor and a stirrup connected to the other end fitting of the first voltage dropping device to facilitate installing an electrically conductive jumper with the clamp to the electrically isolated lead wire.

10. The device of claim 1 wherein the voltage dropping device includes an electrically conductive fitting attached directly to the electrically isolated lead wire which is electrically insulated from the first housing on a first end and a second end of the said voltage dropping device includes an electrically conductive fitting attached to an overcurrent protective device, the overcurrent protective device is connected via an electrically conductive jumper to at least one of the second power line conductor, a neutral conductor, or an earth ground conductor.

11. The device of claim 10 wherein the electrically conductive fitting includes a sealed electrical insulator and a valve configured to create a negative pressure within the sealed electrical insulator.

12. The device of claim 1 wherein the electrically isolated lead wire is connected to the first measuring resistor on a first end to an electrically conductive stud on a second end, the electrically conductive stud is electrically isolated from the first housing, and an electrically conductive hinge post is threaded onto the stud to support a first side of a flexible electrically conductive stirrup assembly, and a second electrically conductive stud electrically isolated from the first housing and a second electrically conductive hinge post support a second side of the stirrup assembly.

13. The device of claim 12, wherein the stud, the second stud, the hinge post, and the second hinge post are electrically isolated from the first housing with a plurality of electrical insulators.

14. The device of claim 12, including a clamp connecting one end of an electrically conductive jumper to the stirrup assembly.

15. The device of claim 14, wherein the jumper includes an electrically conductive internal wire and an electrically insulating cover, a first hotline clamp is attached on a first end of the jumper and a second hotline clamp attached on a second end of the jumper, the first hotline clamp is attached to the flexible stirrup assembly and the second hotline clamp is attached to a stirrup on the first voltage dropping device.

16. The device of claim 15 including an electrical interrupting device configured to isolate the voltage dropping device from the measuring resistor when an excessive current flows through the first voltage dropping device and the first measuring resistor to prevent a phase to phase, phase to neutral, or phase to earth ground fault on the power system.

17. The device of claim 1 wherein the electrically isolated lead wire is electrically isolated from said first housing and connected to the measuring resistor on a first end and connected to an electrically conductive stud on a second end, the electrically conductive stud is electrically isolated from the housing and includes an electrically conductive ring connector threaded on the electrically conductive stud for attachment of a hotline clamp to the electrically conductive ring connector.

18. The device of claim 1 wherein the electrically isolated lead wire is isolated from the housing and connected to the first measuring resistor on a first end and to an electrically conductive stud on a second end, the electrically conductive stud is electrically isolated from the housing and an electrically conductive hinge post threaded onto the stud, a jumper attached to the hinge post.

19. The device of claim 1 including a "C" loop coil configured to measure a current waveform and a measured angle between a measured line current phasor and a measured voltage phasor.

20. The system of claim 1 wherein the power system is a single phase delta connected ungrounded system.

21. The system of claim 20 includes:
a first lightning arrester configured to be installed near the first housing, a first arrester lead wire configured to be connected to the first power line conductor, and a first arrester ground lead configured to be connected to an earth grounded conductor; and
a second lightning arrester including a second lightning arrester lead wire configured to be connected to the second power line conductor and a second arrester ground lead is configured to be connected to an earth grounded conductor.

22. The system of claim 20, wherein the first housing includes:
a "C" loop coil configured to measure a line current in the first power line conductor.

23. The system of claim 20 wherein a lightning stroke voltage is measured between the first power line conductor and the second power line conductor.

24. The system of claim 1 wherein the electric power system is a three phase delta connected ungrounded system and includes:
a second housing having a second housing configured to be installed on the second power line conductor and a second voltage dropping device configured to be installed on a third power line conductor; and
a third housing having a third housing configured to be installed on a third power line conductor and a third voltage dropping device connected to the first power line conductor for measuring three phase to phase voltages.

25. The system of claim 24 wherein a lightning stroke voltage is measured between the first power line conductor, the second power line conductor, and the third power line conductor.

26. The system of claim 24 wherein the first housing includes a first lightning arrester configured to be attached near the first housing with a first arrester lead wire configured to be connected to the first power line conductor and a first arrester ground lead configured to be connected to an earth ground conductor, the second housing includes a second lightning arrester configured to be attached near the second housing with a second arrester lead wire configured to be connected to the second power line conductor and a second arrester ground lead configured to be connected to an earth ground conductor, and a third lightning arrester configured to be attached near the third housing with a third arrester lead wire configured to be connected to the third power line conductor and a third arrester ground lead configured to be connected to the earth ground conductor for measuring the three phase to phase voltages.

27. The system of claim 24 wherein the first housing includes a first "C" loop coil for measuring a first line current in the first power line conductor and the second housing includes a second "C" loop coil for measuring a second line current in the second power line conductor, and the third housing includes a third "C" loop coil for measuring a third line current in the third power line conductor.

28. A device for measuring the voltage of an electric power line conductor for a power system comprising:
a first electrically conductive housing configured to be installed on a first power line conductor;
a first virtual grounding member configured to electrically ground the first housing to a first power line conductor voltage;
a first measuring resistor electrically connected between the first virtual ground member and an electrically isolated lead wire, the electrically isolated lead wire electrically connected to a first voltage dropping device, the first voltage dropping device configured to be electrically connected to an earth grounded neutral conductor; and a sensor electronics module configured to measure a voltage drop across the first measuring resistor, the voltage drop being directly proportional to a voltage between the first power line conductor and the earth grounded neutral conductor.

29. The system of claim 28, wherein the power system is a single phase multi-grounded wye connected system and the first housing includes:
a first lightning arrester configured to be installed near the first housing having a first arrestor lead wire configured to be connected to the first power line conductor, the first voltage dropping device attached to a grounding stud of the first lightning arrester, a first ground lead of the first lightning arrester is configured to be connected to the earth grounded neutral conductor for measuring the voltage between the first power line conductor and the earth grounded neutral conductor.

30. The system of claim 28, wherein the first voltage dropping device is configured to be connected to the earth grounded neutral conductor and to the measuring resistor of the first housing for measuring the voltage between the first power line conductor and the earth grounded neutral conductor.

31. The system of claim 28, wherein the power system is a single phase multi-grounded wye connected system and wherein the first voltage dropping device is configured to be connected to the earth grounded neutral conductor and the first measuring resistor for measuring the voltage between the first power line conductor and the earth grounded neutral conductor and the first housing includes a first "C" loop coil for measuring a phase current in the first power line conductor.

32. The system of claim 30 wherein a lightning stroke voltage is measured between the first power line conductor and the earth grounded neutral conductor.

33. The system of claim 28 wherein the power system is a three phase multi-grounded wye connected system and the first housing is configured to be mounted on the first power line conductor having the first voltage dropping device configured to be connected to the first measuring resistor for measuring the voltage between the first power line conductor and the earth grounded neutral conductor;
a second housing is configured to be mounted on the second power line conductor having a second voltage dropping device configured to be connected to a second measuring resistor for measuring a voltage between the second power line conductor and the earth grounded neutral conductor; and
a third housing is configured to be mounted on a third power line conductor having a third voltage dropping device configured to be connected to a third measuring resistor for measuring a voltage between the third power line conductor and the earth grounded neutral conductor.

34. The system of claim 33 including:
a first lightning arrester configured to be installed near the first housing having a first arrester lead wire configured to be connected to the first power line conductor and a first arrester ground lead connected to the first voltage dropping device and configured to be connected to the earth grounded neutral conductor and the first measuring resistor of the first housing for measuring the voltage between the first power line conductor and the earth grounded neutral conductor;
a second lightning arrester configured to be installed near the second housing having a second arrester lead wire configured to be connected to the second power line conductor and a second arrester ground lead connected to the second voltage dropping device and configured to be connected to the earth grounded neutral conductor and the second measuring resistor of the second housing for measuring the voltage between the second power line conductor and the earth grounded neutral conductor and
a third lightning arrester configured to be installed near the third housing with a third arrester lead wire configured to be connected to the third power line conductor and a third arrester ground lead connected to the third voltage dropping device and configured to be connected to the earth grounded neutral conductor and the third measuring resistor of the third housing for measuring the voltage between the third power line conductor and the earth grounded neutral conductor.

35. The system of claim 34 wherein the first housing includes a first "C" loop coil for measuring the phase current in the first power line conductor, the second housing includes a second "C" loop coil for measuring the phase current in the second power line conductor, and the third housing including a third "C" loop coil for measuring the phase current in the third power line conductor.

36. A device for measuring the voltage of an electric power line conductor for a power system comprising:
a first electrically conductive housing configured to be installed on a first power line conductor;
a first virtual grounding member configured to electrically ground the first housing to a first power line conductor voltage;
a first measuring resistor electrically connected between the first virtual ground member and an electrically isolated lead wire, the electrically isolated lead wire electrically connected to a first voltage dropping device, the first voltage dropping device configured to be electrically connected to an ungrounded neutral conductor; and
a sensor electronics module configured to measure a voltage drop across the first measuring resistor, the voltage drop being directly proportional to a voltage between the first power line conductor and the ungrounded neutral conductor.

37. The system of claim 36, wherein the power system is a single phase ungrounded wye connected system and the first housing includes:
a first lightning arrester configured to be installed near the first housing having a first arrester lead wire configured to be connected to the first power line conductor with an arrester ground lead connected to earth ground.

38. The system of claim 36 wherein the power system is a single phase ungrounded wye connected system and the first voltage dropping device is configured to be connected to the ungrounded neutral conductor for measuring the voltage between the first power line conductor and the ungrounded neutral conductor, and the first housing includes a first "C" loop coil for measuring a phase current in the first power line conductor.

39. The system of claim 38 wherein a lightning stroke voltage is measured between the first power line conductor and the ungrounded neutral conductor.

* * * * *